(12) United States Patent
Szabo et al.

(10) Patent No.: US 12,232,790 B2
(45) Date of Patent: *Feb. 25, 2025

(54) ADJUSTABLE ANGLE ORTHOPEDIC DISTRACTOR, COMPRESSOR, AND DISTRACTOR-COMPRESSOR

(71) Applicant: IvyTech Design LLC, Wilmington, DE (US)

(72) Inventors: Nicholas Szabo, Philadelphia, PA (US); Trevor Chan, Philadelphia, PA (US); Joshua Robert Vogel, Pembroke Pines, FL (US); Shelby Meckstroth, New Orleans, LA (US)

(73) Assignee: Ivytech Design LLC, Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/401,121

(22) Filed: Dec. 29, 2023

(65) Prior Publication Data

US 2024/0216031 A1 Jul. 4, 2024

Related U.S. Application Data

(60) Provisional application No. 63/436,387, filed on Dec. 30, 2022.

(51) Int. Cl.
*A61B 17/88* (2006.01)
*A61B 17/56* (2006.01)

(52) U.S. Cl.
CPC .... *A61B 17/8866* (2013.01); *A61B 2017/564* (2013.01)

(58) Field of Classification Search
CPC ............... A61B 17/8866; A61B 2017/564
See application file for complete search history.

(56) References Cited

U.S. PATENT DOCUMENTS

| | | |
|---|---|---|
| 4,475,544 A | 10/1984 | Reis |
| 4,944,739 A | 7/1990 | Torre |
| 6,315,780 B1 | 11/2001 | Lalonde |
| 6,716,218 B2 | 4/2004 | Holmes |
| 7,097,647 B2 | 8/2006 | Segler |
| 7,141,015 B2 | 11/2006 | Ruane |
| 8,951,258 B2 * | 2/2015 | Peultier .............. A61B 17/7077 606/279 |
| 8,979,850 B2 | 3/2015 | Johnstone |
| 9,339,319 B2 | 5/2016 | Schmuck |
| RE46,582 E | 10/2017 | Morgan |
| 9,795,399 B2 | 10/2017 | Metzger |
| 9,795,410 B2 | 10/2017 | Shenoy |
| 9,801,546 B2 | 10/2017 | Donner |
| 9,801,639 B2 | 10/2017 | O'Neil |
| 9,801,640 B2 | 10/2017 | O'Neil |
| 9,801,729 B2 | 10/2017 | DiMauro |
| 9,808,346 B2 | 11/2017 | Stark |
| 9,808,351 B2 | 11/2017 | Kelly |

(Continued)

*Primary Examiner* — Sameh R Boles
(74) *Attorney, Agent, or Firm* — Hoffberg & Associates; Steven M. Hoffberg

(57) ABSTRACT

An orthopedic instrument, comprising a pair of pivotally-connected arms, extending beyond a pivot axis of a first pivot; a pair of feet mounted to ends of the pair of pivotally-connected arms; and a quadrilateral linkage configured to maintain parallelism between the pair of feet over a range of angles and to selectively alter a distance between the pair of feet.

20 Claims, 60 Drawing Sheets

(56) References Cited

U.S. PATENT DOCUMENTS

| | | | |
|---|---|---|---|
| 9,814,499 | B2 | 11/2017 | Buscaglia |
| 9,814,590 | B2 | 11/2017 | Serhan |
| 9,827,108 | B2 | 11/2017 | de Villiers |
| 9,833,335 | B2 | 12/2017 | Weiland |
| 9,839,374 | B2 | 12/2017 | Roche |
| 9,844,335 | B2 | 12/2017 | Stein |
| 9,848,914 | B2 | 12/2017 | Pool |
| 9,848,995 | B2 | 12/2017 | Ullrich, Jr. |
| 9,855,075 | B2 | 1/2018 | Van Der Walt |
| 9,861,446 | B2 | 1/2018 | Lang |
| 9,872,709 | B2 | 1/2018 | Luhmann |
| 9,877,846 | B2 | 1/2018 | Dvorak |
| 9,888,928 | B2 | 2/2018 | Collazo |
| 9,889,020 | B2 | 2/2018 | Baynham |
| 9,913,734 | B2 | 3/2018 | White |
| 9,918,849 | B2 | 3/2018 | Morris |
| 9,925,060 | B2 | 3/2018 | DiMauro |
| 9,936,994 | B2 | 4/2018 | Smith |
| 9,937,062 | B2 | 4/2018 | Stein |
| 9,943,418 | B2 | 4/2018 | Davenport |
| 9,949,731 | B2 | 4/2018 | Erramilli |
| 9,956,003 | B2 | 5/2018 | Prevost |
| 9,956,010 | B2 | 5/2018 | Richelsoph |
| 9,962,204 | B2 | 5/2018 | Mirghasemi |
| 9,968,376 | B2 | 5/2018 | Metzger |
| 9,968,573 | B2 | 5/2018 | Hoffmann |
| 9,980,780 | B2 | 5/2018 | Lang |
| 9,981,071 | B2 | 5/2018 | McClain |
| 9,987,024 | B2 | 6/2018 | Frey |
| 9,999,416 | B2 | 6/2018 | Kelly |
| 9,999,519 | B2 | 6/2018 | Garcia-Bengochea |
| 10,004,449 | B2 | 6/2018 | Stein |
| 10,004,538 | B2 | 6/2018 | McNab |
| 10,016,221 | B2 | 7/2018 | Kiester |
| 10,016,226 | B2 | 7/2018 | Fening |
| 10,028,771 | B2 | 7/2018 | Artaki |
| 10,028,837 | B2 | 7/2018 | Wei |
| 10,034,767 | B2 | 7/2018 | Baynham |
| 10,034,769 | B2 | 7/2018 | Baynham |
| 10,039,570 | B2 | 8/2018 | Farzadfard |
| 10,039,661 | B2 | 8/2018 | Pool |
| 10,045,807 | B2 | 8/2018 | Santrock |
| 10,064,739 | B2 | 9/2018 | Duggal |
| 10,070,968 | B2 | 9/2018 | Greenhalgh |
| 10,070,973 | B2 | 9/2018 | Sherman |
| 10,080,559 | B2 | 9/2018 | Beale |
| 10,080,590 | B2 | 9/2018 | Abdou |
| 10,080,670 | B2 | 9/2018 | Sandstrom |
| 10,085,843 | B2 | 10/2018 | DiMauro |
| 10,085,855 | B2 | 10/2018 | Ty |
| 10,092,283 | B2 | 10/2018 | Cryder |
| 10,098,681 | B2 | 10/2018 | Wei |
| 10,105,167 | B2 | 10/2018 | Pool |
| 10,111,757 | B2 | 10/2018 | Abdou |
| 10,117,682 | B2 | 11/2018 | Wolters |
| 10,117,972 | B2 | 11/2018 | McClain |
| 10,149,673 | B2 | 12/2018 | McCormack |
| 10,149,674 | B2 | 12/2018 | Angus |
| 10,159,498 | B2 | 12/2018 | Uthgenannt |
| 10,159,530 | B2 | 12/2018 | Lang |
| 10,159,578 | B2 | 12/2018 | Zubok |
| 10,159,869 | B2 | 12/2018 | Bird |
| 10,159,870 | B2 | 12/2018 | Bird |
| 10,179,054 | B2 | 1/2019 | Kleiner |
| 10,188,529 | B2 | 1/2019 | Abdou |
| 10,188,772 | B2 | 1/2019 | McClain |
| 10,194,958 | B2 | 2/2019 | Bobbitt |
| 10,194,959 | B2 | 2/2019 | Gephart |
| 10,195,053 | B2 | 2/2019 | Kleiner |
| 10,201,891 | B2 | 2/2019 | Williams |
| 10,206,695 | B2 | 2/2019 | Meridew |
| 10,206,697 | B2 | 2/2019 | Metzger |
| 10,206,714 | B2 | 2/2019 | van der Walt |
| 10,206,792 | B2 | 2/2019 | Sherman |
| 10,213,322 | B2 | 2/2019 | Errico |
| 10,226,285 | B2 | 3/2019 | McCormack |
| 10,226,360 | B2 | 3/2019 | Baynham |
| 10,231,739 | B1 | 3/2019 | Bonutti |
| 10,231,849 | B2 | 3/2019 | Squires |
| 10,238,378 | B2 | 3/2019 | Bonutti |
| 10,238,499 | B2 | 3/2019 | Baynham |
| 10,238,508 | B2 | 3/2019 | Sack |
| 10,245,087 | B2 | 4/2019 | Donner |
| 10,245,154 | B2 | 4/2019 | Dudasik |
| 10,251,676 | B2 | 4/2019 | Brunner |
| 10,278,687 | B2 | 5/2019 | Cryder |
| 10,278,711 | B2 | 5/2019 | Meridew |
| 10,278,777 | B1 | 5/2019 | Lang |
| 10,285,683 | B2 | 5/2019 | Plaskos |
| 10,292,768 | B2 | 5/2019 | Lang |
| 10,293,147 | B2 | 5/2019 | Culbert |
| 10,299,934 | B2 | 5/2019 | Seifert |
| 10,307,263 | B2 | 6/2019 | Dzioba |
| 10,321,904 | B2 | 6/2019 | Plaskos |
| 10,321,918 | B2 | 6/2019 | Bonutti |
| 10,322,011 | B2 | 6/2019 | Baynham |
| 10,335,209 | B2 | 7/2019 | Hutton |
| 10,335,220 | B2 | 7/2019 | Smith |
| 10,349,982 | B2 | 7/2019 | Culbert |
| 10,349,995 | B2 | 7/2019 | Walker |
| 10,350,081 | B2 | 7/2019 | Seifert |
| 10,350,391 | B2 | 7/2019 | McClain |
| 10,363,073 | B2 | 7/2019 | Raina |
| 10,368,854 | B2 | 8/2019 | Pell |
| 10,368,947 | B2 | 8/2019 | Lang |
| 10,376,287 | B2 | 8/2019 | Torrie |
| 10,376,372 | B2 | 8/2019 | Serhan |
| 10,383,665 | B2 | 8/2019 | Stern |
| 10,390,845 | B2 | 8/2019 | Vanasse |
| 10,390,862 | B2 | 8/2019 | Bobbitt |
| 10,398,572 | B2 | 9/2019 | Zubok |
| 10,405,841 | B2 | 9/2019 | Gorek |
| 10,405,927 | B1 | 9/2019 | Lang |
| 10,405,986 | B2 | 9/2019 | Kelly |
| 10,405,989 | B2 | 9/2019 | O'Neil |
| 10,413,287 | B2 | 9/2019 | Heiges |
| 10,413,426 | B2 | 9/2019 | Parry |
| 10,420,593 | B2 | 9/2019 | Wall |
| 10,420,651 | B2 | 9/2019 | Serhan |
| 10,420,655 | B2 | 9/2019 | Foley |
| 10,426,453 | B2 | 10/2019 | Kaiser |
| 10,426,454 | B2 | 10/2019 | Ponmudi |
| 10,426,492 | B2 | 10/2019 | Metzger |
| 10,433,872 | B2 | 10/2019 | Starr |
| 10,433,880 | B2 | 10/2019 | Donner |
| 10,433,887 | B2 | 10/2019 | Noon |
| 10,433,971 | B2 | 10/2019 | DiMauro |
| 10,433,979 | B2 | 10/2019 | Morris |
| 10,441,318 | B2 | 10/2019 | Donner |
| 10,449,057 | B2 | 10/2019 | O'Neil |
| 10,456,175 | B2 | 10/2019 | McCormack |
| 10,463,402 | B2 | 11/2019 | Biester |
| 10,463,406 | B2 | 11/2019 | Chang |
| 10,470,780 | B2 | 11/2019 | Bonutti |
| 10,478,232 | B2 | 11/2019 | Pool |
| 10,478,364 | B2 | 11/2019 | Fossez |
| 10,485,530 | B2 | 11/2019 | Ruhling |
| 10,485,678 | B2 | 11/2019 | Garcia-Bengochea |
| 10,492,688 | B2 | 12/2019 | Donner |
| 10,492,918 | B2 | 12/2019 | DiMauro |
| 10,499,894 | B2 | 12/2019 | O'Brien |
| 10,507,120 | B2 | 12/2019 | Gharib |
| 10,512,470 | B1 | 12/2019 | Bays |
| 10,524,808 | B1 | 1/2020 | Hissong |
| 10,543,022 | B2 | 1/2020 | Italiaie |
| 10,543,024 | B2 | 1/2020 | Lee |
| 10,543,107 | B2 | 1/2020 | Abdou |
| 10,543,108 | B2 | 1/2020 | Dvorak |
| 10,548,739 | B2 | 2/2020 | de Villiers |
| 10,549,014 | B2 | 2/2020 | Kerr |
| 10,555,757 | B2 | 2/2020 | Dayton |
| 10,555,817 | B2 | 2/2020 | DiMauro |
| 10,561,426 | B1 | 2/2020 | Dayton |
| 10,568,666 | B2 | 2/2020 | McCormack |

(56) References Cited

U.S. PATENT DOCUMENTS

| | | |
|---|---|---|
| 10,568,667 B2 | 2/2020 | Biester |
| 10,575,862 B2 | 3/2020 | Bays |
| 10,575,959 B2 | 3/2020 | DiMauro |
| 10,582,936 B1 | 3/2020 | Hissong |
| 10,582,955 B2 | 3/2020 | Cummins |
| 10,583,013 B2 | 3/2020 | DiMauro |
| 10,588,672 B2 | 3/2020 | McCormack |
| 10,588,754 B2 | 3/2020 | O'Neil |
| 10,603,026 B2 | 3/2020 | Cryder |
| 10,603,046 B2 | 3/2020 | Dayton |
| 10,603,055 B2 | 3/2020 | Donner |
| 10,603,076 B2 | 3/2020 | Ross |
| 10,603,113 B2 | 3/2020 | Lang |
| 10,603,179 B2 | 3/2020 | Pierce |
| 10,610,377 B2 | 4/2020 | Baynham |
| 10,610,380 B2 | 4/2020 | Abdou |
| 10,617,453 B2 | 4/2020 | Beckett |
| 10,624,761 B2 | 4/2020 | Davenport |
| 10,631,900 B2 | 4/2020 | Thoren |
| 10,639,164 B2 | 5/2020 | DiMauro |
| 10,646,213 B2 | 5/2020 | Miller |
| 10,646,258 B2 | 5/2020 | Donner |
| 10,646,262 B2 | 5/2020 | Pool |
| 10,653,408 B2 | 5/2020 | Beale |
| 10,653,467 B2 | 5/2020 | Brumfield |
| 10,660,631 B1 | 5/2020 | Boesel |
| 10,660,675 B2 | 5/2020 | Payne |
| 10,682,130 B2 | 6/2020 | White |
| 10,682,160 B2 | 6/2020 | Shiner |
| 10,687,830 B2 | 6/2020 | Garcia-Bengochea |
| 10,687,867 B2 | 6/2020 | Artaki |
| 10,695,105 B2 | 6/2020 | Abdou |
| 10,695,112 B2 | 6/2020 | Noon |
| 10,722,310 B2 | 7/2020 | Luby |
| 10,729,470 B2 | 8/2020 | Pool |
| 10,729,819 B2 | 8/2020 | McClain |
| 10,736,666 B2 | 8/2020 | Prevost |
| 10,736,667 B2 | 8/2020 | Prevost |
| 10,743,794 B2 | 8/2020 | Pool |
| 10,743,937 B2 | 8/2020 | Uthgenannt |
| 10,743,939 B1 | 8/2020 | Lang |
| 10,751,094 B2 | 8/2020 | Green |
| 10,751,127 B2 | 8/2020 | Dace |
| 10,751,197 B2 | 8/2020 | Dzioba |
| 10,758,288 B2 | 9/2020 | Lomeli |
| 10,772,557 B2 | 9/2020 | Windolf |
| 10,772,640 B2 | 9/2020 | Trabish |
| 10,772,641 B2 | 9/2020 | Trabish |
| 10,779,959 B2 | 9/2020 | Ty |
| 10,786,361 B2 | 9/2020 | DiMauro |
| 10,786,362 B2 | 9/2020 | Duggal |
| 10,799,296 B2 | 10/2020 | Lang |
| 10,806,493 B2 | 10/2020 | Sadat |
| 10,806,593 B2 | 10/2020 | Lomeli |
| 10,828,070 B2 | 11/2020 | Ziemek |
| 10,835,290 B2 | 11/2020 | Cheng |
| 10,835,385 B2 | 11/2020 | Zubok |
| 10,835,389 B2 | 11/2020 | Errico |
| 10,849,609 B2 | 12/2020 | Plaskos |
| 10,849,631 B2 | 12/2020 | Hatch |
| 10,849,663 B2 | 12/2020 | Dayton |
| 10,849,670 B2 | 12/2020 | Santrock |
| 10,849,693 B2 | 12/2020 | Lang |
| 10,856,914 B2 | 12/2020 | Wolters |
| 10,857,004 B2 | 12/2020 | Abdou |
| 10,864,019 B2 | 12/2020 | van der Walt |
| 10,874,414 B2 | 12/2020 | Pepper |
| 10,874,438 B2 | 12/2020 | Biester |
| 10,874,446 B2 | 12/2020 | Smith |
| 10,888,335 B2 | 1/2021 | Dayton |
| 10,893,874 B2 | 1/2021 | DeMers |
| 10,893,876 B2 | 1/2021 | Uthgenannt |
| 10,893,879 B2 | 1/2021 | Metzger |
| 10,898,253 B2 | 1/2021 | Suddaby |
| 10,918,425 B2 | 2/2021 | Schwardt |
| 10,918,498 B2 | 2/2021 | Abdou |
| 10,932,826 B2 | 3/2021 | Hutton |
| 10,939,939 B1 | 3/2021 | Gil |
| 10,945,764 B2 | 3/2021 | Dayton |
| 10,945,773 B2 | 3/2021 | Medeiros |
| 10,945,861 B2 | 3/2021 | Abdou |
| 10,959,760 B2 | 3/2021 | Bobbitt |
| 10,966,736 B2 | 4/2021 | Lehman, Jr. |
| 10,966,839 B2 | 4/2021 | Beale |
| 10,973,529 B2 | 4/2021 | Lavallee |
| 10,980,528 B2 | 4/2021 | Cryder |
| 10,980,575 B2 | 4/2021 | Perrow |
| 10,993,783 B2 | 5/2021 | Wu |
| 2001/0010008 A1 | 7/2001 | Gellman |
| 2002/0022764 A1 | 2/2002 | Smith |
| 2002/0161375 A1 | 10/2002 | Ralph |
| 2004/0102790 A1 | 5/2004 | Ralph |
| 2004/0147935 A1 | 7/2004 | Segler |
| 2004/0162568 A1 | 8/2004 | Saadat |
| 2004/0176763 A1 | 9/2004 | Foley |
| 2004/0186346 A1 | 9/2004 | Smith |
| 2004/0199169 A1 | 10/2004 | Koons |
| 2004/0225183 A1 | 11/2004 | Michlitsch |
| 2004/0225295 A1 | 11/2004 | Zubok |
| 2004/0225305 A1 | 11/2004 | Ewers |
| 2005/0038498 A1 | 2/2005 | Dubrow |
| 2005/0075653 A1 | 4/2005 | Saadat |
| 2005/0085720 A1 | 4/2005 | Jascob |
| 2005/0143747 A1 | 6/2005 | Zubok |
| 2005/0221072 A1 | 10/2005 | Dubrow |
| 2005/0222576 A1 | 10/2005 | Kick |
| 2005/0245945 A1 | 11/2005 | Ewers |
| 2006/0025677 A1 | 2/2006 | Verard |
| 2006/0036255 A1 | 2/2006 | Pond |
| 2006/0041270 A1 | 2/2006 | Lenker |
| 2006/0064164 A1 | 3/2006 | Thelen |
| 2006/0084867 A1 | 4/2006 | Tremblay |
| 2006/0204738 A1 | 9/2006 | Dubrow |
| 2006/0235279 A1 | 10/2006 | Hawkes |
| 2006/0271061 A1 | 11/2006 | Beyar |
| 2007/0100212 A1 | 5/2007 | Pimenta |
| 2007/0106123 A1 | 5/2007 | Gorek |
| 2007/0198022 A1 | 8/2007 | Lang |
| 2007/0282247 A1 | 12/2007 | Desai |
| 2007/0282448 A1 | 12/2007 | Abdou |
| 2008/0015417 A1 | 1/2008 | Hawkes |
| 2008/0243127 A1 | 10/2008 | Lang |
| 2008/0255498 A1 | 10/2008 | Houle |
| 2008/0262318 A1 | 10/2008 | Gorek |
| 2008/0262504 A1 | 10/2008 | Ralph |
| 2008/0281328 A1 | 11/2008 | Lang |
| 2008/0281329 A1 | 11/2008 | Fitz |
| 2008/0281426 A1 | 11/2008 | Fitz |
| 2009/0012612 A1 | 1/2009 | White |
| 2009/0014016 A1 | 1/2009 | Clifford |
| 2009/0018656 A1 | 1/2009 | Clifford |
| 2009/0018665 A1 | 1/2009 | Clifford |
| 2009/0149857 A1 | 6/2009 | Culbert |
| 2009/0157087 A1 | 6/2009 | Wei |
| 2009/0162643 A1 | 6/2009 | Dubrow |
| 2009/0216234 A1 | 8/2009 | Farr |
| 2009/0259107 A1 | 10/2009 | Crenshaw |
| 2009/0264930 A1 | 10/2009 | McBride |
| 2009/0276054 A1 | 11/2009 | Clifford |
| 2010/0160982 A1 | 6/2010 | Justis |
| 2010/0168864 A1 | 7/2010 | White |
| 2010/0178100 A1 | 7/2010 | Fricke |
| 2010/0203155 A1 | 8/2010 | Wei |
| 2010/0204699 A1 | 8/2010 | Wei |
| 2010/0210939 A1 | 8/2010 | Hartmann |
| 2010/0211086 A1 | 8/2010 | Ewers |
| 2010/0249658 A1 | 9/2010 | Sherman |
| 2010/0249659 A1 | 9/2010 | Sherman |
| 2010/0249660 A1 | 9/2010 | Sherman |
| 2010/0249777 A1 | 9/2010 | Sherman |
| 2010/0249789 A1 | 9/2010 | Rock |
| 2010/0268232 A1 | 10/2010 | Betz |
| 2010/0274124 A1 | 10/2010 | Jascob |
| 2010/0286791 A1 | 11/2010 | Goldsmith |

(56) References Cited

U.S. PATENT DOCUMENTS

| | | |
|---|---|---|
| 2010/0305573 A1 | 12/2010 | Fitz |
| 2010/0305574 A1 | 12/2010 | Fitz |
| 2011/0054259 A1 | 3/2011 | Gorek |
| 2011/0054408 A1 | 3/2011 | Wei |
| 2011/0066193 A1 | 3/2011 | Lang |
| 2011/0071581 A1 | 3/2011 | Lang |
| 2011/0071643 A1 | 3/2011 | Clifford |
| 2011/0184325 A1 | 7/2011 | Behzadian |
| 2011/0184476 A1 | 7/2011 | Ralph |
| 2011/0201984 A1 | 8/2011 | Dubrow |
| 2011/0213368 A1 | 9/2011 | Fitz |
| 2011/0213373 A1 | 9/2011 | Fitz |
| 2011/0213374 A1 | 9/2011 | Fitz |
| 2011/0213377 A1 | 9/2011 | Lang |
| 2011/0213427 A1 | 9/2011 | Fitz |
| 2011/0213428 A1 | 9/2011 | Fitz |
| 2011/0213429 A1 | 9/2011 | Lang |
| 2011/0213430 A1 | 9/2011 | Lang |
| 2011/0213431 A1 | 9/2011 | Fitz |
| 2011/0218539 A1 | 9/2011 | Fitz |
| 2011/0218584 A1 | 9/2011 | Fitz |
| 2011/0230888 A1 | 9/2011 | Lang |
| 2011/0238073 A1 | 9/2011 | Lang |
| 2011/0240064 A1 | 10/2011 | Wales |
| 2011/0250626 A1 | 10/2011 | Williams |
| 2011/0257664 A1 | 10/2011 | Cauthen, III |
| 2011/0295329 A1 | 12/2011 | Fitz |
| 2011/0313423 A1 | 12/2011 | Lang |
| 2011/0319897 A1 | 12/2011 | Lang |
| 2011/0319900 A1 | 12/2011 | Lang |
| 2012/0029520 A1 | 2/2012 | Lang |
| 2012/0066892 A1 | 3/2012 | Lang |
| 2012/0071881 A1 | 3/2012 | Lang |
| 2012/0071882 A1 | 3/2012 | Lang |
| 2012/0071883 A1 | 3/2012 | Lang |
| 2012/0072185 A1 | 3/2012 | Lang |
| 2012/0097194 A1 | 4/2012 | McDaniel |
| 2012/0101503 A1 | 4/2012 | Lang |
| 2012/0130180 A1 | 5/2012 | Pell |
| 2012/0143197 A1 | 6/2012 | Lang |
| 2012/0203070 A1 | 8/2012 | Crenshaw |
| 2012/0215315 A1 | 8/2012 | Hochschuler |
| 2013/0019883 A1 | 1/2013 | Worm |
| 2013/0041228 A1 | 2/2013 | Gorek |
| 2013/0123792 A1 | 5/2013 | Fitz |
| 2013/0131683 A1 | 5/2013 | Shah |
| 2013/0144297 A1 | 6/2013 | Wilkinson |
| 2013/0173004 A1 | 7/2013 | Greenhalgh |
| 2013/0204372 A1 | 8/2013 | Mohar |
| 2013/0218272 A1 | 8/2013 | Clifford |
| 2013/0237766 A1 | 9/2013 | Pell |
| 2014/0018707 A1 | 1/2014 | Sherman |
| 2014/0038777 A1 | 2/2014 | Bird |
| 2014/0058399 A1 | 2/2014 | Shah |
| 2014/0066936 A1 | 3/2014 | Fitz |
| 2014/0074441 A1 | 3/2014 | Fitz |
| 2014/0107659 A1 | 4/2014 | Walters |
| 2014/0148692 A1 | 5/2014 | Hartmann |
| 2014/0148828 A1 | 5/2014 | Ewers |
| 2014/0163664 A1 | 6/2014 | Goldsmith |
| 2014/0163683 A1 | 6/2014 | Seifert |
| 2014/0172110 A1 | 6/2014 | Ralph |
| 2014/0196631 A1 | 7/2014 | McDaniel |
| 2014/0222007 A1 | 8/2014 | Rock |
| 2014/0243605 A1 | 8/2014 | Gorek |
| 2014/0316439 A1 | 10/2014 | Cauthen, III |
| 2014/0364917 A1 | 12/2014 | Sandstrom |
| 2014/0378980 A1 | 12/2014 | Lomeli |
| 2015/0010341 A1 | 1/2015 | Fricke |
| 2015/0032163 A1 | 1/2015 | Abdou |
| 2015/0119989 A1 | 4/2015 | Pimenta |
| 2015/0148194 A1 | 5/2015 | Bird |
| 2015/0148886 A1 | 5/2015 | Rao |
| 2015/0157305 A1 | 6/2015 | Gorek |
| 2015/0165272 A1 | 6/2015 | Bird |
| 2015/0250672 A1 | 9/2015 | Fossez |
| 2015/0289910 A1 | 10/2015 | Mirghasemi |
| 2015/0351734 A1 | 12/2015 | Crenshaw |
| 2016/0022429 A1 | 1/2016 | Greenhalgh |
| 2016/0038182 A1 | 2/2016 | Gorek |
| 2016/0038207 A1 | 2/2016 | Wei |
| 2016/0074124 A1 | 3/2016 | Fitz |
| 2016/0089188 A1 | 3/2016 | McBride, Jr. |
| 2016/0206331 A1 | 7/2016 | Fitz |
| 2016/0242923 A1 | 8/2016 | Davenport |
| 2016/0242927 A1 | 8/2016 | Seifert |
| 2016/0250038 A1 | 9/2016 | Wei |
| 2016/0278821 A1 | 9/2016 | Artaki |
| 2017/0135706 A1 | 5/2017 | Frey |
| 2017/0143513 A1 | 5/2017 | Sandstrom |
| 2017/0143945 A1 | 5/2017 | Culbert |
| 2017/0151022 A1 | 6/2017 | Jascob |
| 2017/0181864 A1 | 6/2017 | Davenport |
| 2017/0182225 A1 | 6/2017 | Rao |
| 2017/0245872 A1 | 8/2017 | Rock |
| 2017/0252072 A1 | 9/2017 | Artaki |
| 2017/0273677 A1 | 9/2017 | Gorek |
| 2017/0333756 A1 | 11/2017 | Bird |
| 2017/0340321 A1 | 11/2017 | Cauthen, III |
| 2017/0340454 A1 | 11/2017 | Lomeli |
| 2018/0035992 A1 | 2/2018 | Pell |
| 2018/0064497 A1 | 3/2018 | Hussain |
| 2018/0098788 A1 | 4/2018 | White |
| 2018/0098798 A1 | 4/2018 | Italiaie |
| 2018/0193162 A1 | 7/2018 | Davenport |
| 2018/0271576 A1 | 9/2018 | Lomeli |
| 2018/0296253 A1 | 10/2018 | Artaki |
| 2018/0353813 A9 | 12/2018 | Bird |
| 2018/0368986 A1 | 12/2018 | Greenhalgh |
| 2019/0008532 A1 | 1/2019 | Fitz |
| 2019/0090979 A1 | 3/2019 | Medeiros |
| 2019/0110821 A1 | 4/2019 | Perrow |
| 2019/0151716 A1 | 5/2019 | Bird |
| 2019/0216454 A1 | 7/2019 | Thommen |
| 2019/0247050 A1 | 8/2019 | Goldsmith |
| 2019/0269469 A1 | 9/2019 | Bush, Jr. |
| 2019/0336302 A1 | 11/2019 | Seifert |
| 2019/0336652 A1 | 11/2019 | Rao |
| 2020/0000495 A1 | 1/2020 | Italiaie |
| 2020/0054315 A1 | 2/2020 | Pell |
| 2020/0077996 A1 | 3/2020 | Gorek |
| 2020/0093529 A1 | 3/2020 | Biedermann |
| 2020/0138518 A1 | 5/2020 | Lang |
| 2020/0170723 A1 | 6/2020 | Crawford |
| 2020/0170730 A1 | 6/2020 | Cameron |
| 2020/0205993 A1 | 7/2020 | Davenport |
| 2020/0253657 A1 | 8/2020 | Suddaby |
| 2020/0268368 A1 | 8/2020 | White |
| 2021/0023250 A1 | 1/2021 | Golkowski |

* cited by examiner

ADJUSTABLE ANGLE ORTHOPEDIC DISTRACTOR, COMPRESSOR, AND DISTRACTOR-COMPRESSOR

CROSS REFERENCE TO RELATED APPLICATIONS

The present application is a non-provisional of, and claims benefit of priority from, U.S. Provisional Patent Application No. 63/436,387, filed Dec. 30, 2022, the entirety of which is expressly incorporated herein by reference.

FIELD OF THE INVENTION

The present invention relates to the field of orthopedic distractors and compressors, and more particularly to orthopedic distractors and compressors with control of proximity and angle of proximation.

BACKGROUND OF THE INVENTION

Each reference or patent cited herein is expressly incorporated herein by reference in its entirety.

A number of devices are known for separating proximate bones during a procedure. These are known as bone distractors. Because the human hand is well adapted to generate a squeezing force, these devices generally have handles which are pivoting about an axis, but the working end does not cross the pivot plane. A more complex mechanism may be implemented to convert the squeezing force into a distraction force, which may pass the force across a main pivot plane or axis of symmetry.

A bone compressor is a device that is used to compress proximate bones across a gap, such as due to injury or during an orthopedic procedure. When the bones are compressed into proximity, alignment is important. Typically, after alignment, the bones are fixed with a plate or other fixation device, though in some cases the compressor fixture is maintained until the bone fuses.

A bone plate is a metal implantable device used to mechanically hold and stabilize two bone fragments together after alignment of the bones. This implant aids in the fusion of the bones through healing and is fastened to the bone with screws. Proper placement of this device requires it to rest flat on the two adjoining pieces of bone.

When compression is achieved by squeezing handles about a pivot, the operational end of the device normally follows an arc, and therefore if the bone is aligned and fixed to the device before compression of the handles, after compression, alignment will be lost. Further, the optimal alignment may not be clear before the handles are compressed.

Thus, where the levers cross the pivot at the plane of symmetry, a compression on one side leads to a compression on the other; while where the levers are reflected at the pivot at the plane of symmetry, a compression at one side leads to an expansion at the other. The distal ends sweep an arc, and therefore have an intrinsic relationship between displacement and angle.

Other instruments are known that convert an axial movement to a change in angle between elements perpendicular to the axis. In simple designs, both the distance between the elements and angle are dependent on the displacement along the axis.

U.S. Pat. No. 4,944,739 discloses a bone fixation clamp with distal feet that compress two bone fragments together. The feet cannot be mounted into the bone and therefore may be prone to lateral repositioning on the bone surface during compression, which leads to failure of collinear alignment of bone fragments when proximated. In addition, because the feet cannot be screwed into the bone or hold the bone by means other than manual compression, this device could not be used for distraction of bone fragments and cleaning of the cartilage surface. This bone clamp is intended for use in fusing bones with a diagonal cut after an osteotomy rather than for transverse fractures.

U.S. Pat. No. 4,475,544 discloses a scissors-like bone clamp similar to the above device except for having sharp distal feet that are turned inwards towards each other.

U.S. Pat. No. 9,339,319 discloses a surgical instrument that is capable of both distraction and compression of bone fragments through engagement of tips with one or more implants in the bone. This patent describes an instrument that has one tip that engages with a bone plate and another that can engage with a bone fastener, such as a guide wire and/or a screw, and uses a ratchet mechanism to move the distal ends with respect to one another and hold them in a locked position.

U.S. Pat. No. 6,315,780 discloses a bone clamp that has a pair of jaws with spikes that effect stabilization of two adjacent bone fragments in parallel, and uses a ratcheting mechanism to apply and maintain pressure.

The Jansen retractor has a central screw and passes through a follower that displaces extensions of a pair of pivoting arms. Thus, the axial displacement is converted to an arcuate movement of the pivoting arms. See, www.eickemeyer.co.uk/Orthopaedic-Implants/Knee/Stifle-Distractor-Wallace.html.

U.S. Pat. No. 7,097,647 discloses an orthopedic device similar to the Jansen retractor, having a central screw actuator that adjusts the angle of a pair of pivoting arms. The mechanism has a screw, and a follower, and controls the distance of a plate from the follower. The plate is connected to a pair of pivoting intermediate arms, which in turn are connected to two pincer arms. The pincer arms have a root pivot axis on lateral aspects of the follower. See, www.dginstruments.com/Tarsal.html. The intermediate arms reduce, but do not eliminate the arcuate movement.

www.intech-medical.com/products/instruments/compressors/parallel-compressor/discloses a complex mechanism, with a scissors mechanism that controls an X-pivot parallel linkage, such that a compression of the handles leads to a change in distance between the bone compression elements, while maintaining parallelism.

See, US Patent and Published Patent Applications 20180271576; 20170340454; 20170245872; 20140378980; 20140222007; 20140018707; 20100249789; 20100249777; 20100249660; 20100249659; 20100249658; 20050143747; 20040225295; 20210023250; 20200268368; 20200253657; 20200205993; 20200170730; 20200170723; 20200138518; 20200093529; 20200077996; 20200054315; 20200000495; 20190336652; 20190336302; 20190269469; 20190247050; 20190216454; 20190151716; 20190110821; 20190090979; 20190008532; 20180368986; 20180353813; 20180296253; 20180193162; 20180098798; 20180098788; 20180064497; 20180035992; 20170340321; 20170333756; 20170273677; 20170252072; 20170182225; 20170181864; 20170151022; 20170143945; 20170143513; 20170135706; 20160278821; 20160250038; 20160242927; 20160242923; 20160206331; 20160089188; 20160074124; 20160038207; 20160038182; 20160022429; 20150351734; 20150289910; 20150250672; 20150165272; 20150157305; 20150148886; 20150148194; 20150119989; 20150032163; 20150010341; 20140364917; 20140316439; 20140243605; 20140196631; 20140172110;

20140163683; 20140163664; 20140148828; 20140148692; 20140107659; 20140074441; 20140066936; 20140058399; 20140038777; 20130237766; 20130218272; 20130204372; 20130173004; 20130144297; 20130131683; 20130123792; 20130041228; 20130019883; 20120215315; 20120203070; 20120143197; 20120130180; 20120101503; 20120097194; 20120072185; 20120071883; 20120071882; 20120071881; 20120066892; 20120029520; 20110319900; 20110319897; 20110313423; 20110295329; 20110257664; 20110250626; 20110240064; 20110238073; 20110230888; 20110218584; 20110218539; 20110213431; 20110213430; 20110213429; 20110213428; 20110213427; 20110213377; 20110213374; 20110213373; 20110213368; 20110201984; 20110184476; 20110184325; 20110071643; 20110071581; 20110066193; 20110054408; 20110054259; 20100305574; 20100305573; 20100286791; 20100274124; 20100268232; 20100211086; 20100210939; 20100204699; 20100203155; 20100178100; 20100168864; 20100160982; 20090276054; 20090264930; 20090259107; 20090216234; 20090162643; 20090157087; 20090149857; 20090018665; 20090018656; 20090014016; 20090012612; 20080281426; 20080281329; 20080281328; 20080262504; 20080262318; 20080255498; 20080243127; 20080015417; 20070282448; 20070282247; 20070198022; 20070106123; 20070100212; 20060271061; 20060235279; 20060204738; 20060084867; 20060064164; 20060041270; 20060036255; 20060025677; 20050245945; 20050222576; 20050221072; 20050085720; 20050075653; 20050038498; 20040225305; 20040225183; 20040199169; 20040186346; 20040176763; 20040162568; 20040147935; 20040102790; 20020161375; 20020022764; 20010010008; U.S. Pat. Nos. 10,993,783; 10,980,575; 10,980,528; 10,973,529; 10,966,839; 10,966,736; 10,959,760; 10,945,861; 10,945,773; 10,945,764; 10,939,939; 10,932,826; 10,918,498; 10,918,425; 10,898,253; 10,893,879; 10,893,876; 10,893,874; 10,888,335; 10,874,446; 10,874,438; 10,874,414; 10,864,019; 10,857,004; 10,856,914; 10,849,693; 10,849,670; 10,849,663; 10,849,631; 10,849,609; 10,835,389; 10,835,385; 10,835,290; 10,828,070; 10,806,593; 10,806,493; 10,799,296; 10,786,362; 10,786,361; 10,779,959; 10,772,641; 10,772,640; 10,772,557; 10,758,288; 10,751,197; 10,751,127; 10,751,094; 10,743,939; 10,743,937; 10,743,794; 10,736,667; 10,736,666; 10,729,819; 10,729,470; 10,722,310; 10,695,112; 10,695,105; 10,687,867; 10,687,830; 10,682,160; 10,682,130; 10,660,675; 10,660,631; 10,653,467; 10,653,408; 10,646,262; 10,646,258; 10,646,213; 10,639,164; 10,631,900; 10,624,761; 10,617,453; 10,610,380; 10,610,377; 10,603,179; 10,603,113; 10,603,076; 10,603,055; 10,603,046; 10,603,026; 10,588,754; 10,588,672; 10,583,013; 10,582,955; 10,582,936; 10,575,959; 10,575,862; 10,568,667; 10,568,666; 10,561,426; 10,555,817; 10,555,757; 10,549,014; 10,548,739; 10,543,108; 10,543,107; 10,543,024; 10,543,022; 10,524,808; 10,512,470; 10,507,120; 10,499,894; 10,492,918; 10,492,688; 10,485,678; 10,485,530; 10,478,364; 10,478,232; 10,470,780; 10,463,406; 10,463,402; 10,456,175; 10,449,057; 10,441,318; 10,433,979; 10,433,971; 10,433,887; 10,433,880; 10,433,872; 10,426,492; 10,426,454; 10,426,453; 10,420,655; 10,420,651; 10,420,593; 10,413,426; 10,413,287; 10,405,989; 10,405,986; 10,405,927; 10,405,841; 10,398,572; 10,390,862; 10,390,845; 10,383,665; 10,376,372; 10,376,287; 10,368,947; 10,368,854; 10,363,073; 10,350,391; 10,350,081; 10,349,995; 10,349,982; 10,335,220; 10,335,209; 10,322,011; 10,321,918; 10,321,904; 10,307,263; 10,299,934; 10,293,147; 10,292,768; 10,285,683; 10,278,777; 10,278,711; 10,278,687; 10,251,676; 10,245,154; 10,245,087; 10,238,508; 10,238,499; 10,238,378; 10,231,849; 10,231,739; 10,226,360; 10,226,285; 10,213,322; 10,206,792; 10,206,714; 10,206,697; 10,206,695; 10,201,891; 10,195,053; 10,194,959; 10,194,958; 10,188,772; 10,188,529; 10,179,054; 10,159,870; 10,159,869; 10,159,578; 10,159,530; 10,159,498; 10,149,674; 10,149,673; 10,117,972; 10,117,682; 10,111,757; 10,105,167; 10,098,681; 10,092,283; 10,085,855; 10,085,843; 10,080,670; 10,080,590; 10,080,559; 10,070,973; 10,070,968; 10,064,739; 10,045,807; 10,039,661; 10,039,570; 10,034,769; 10,034,767; 10,028,837; 10,028,771; 10,016,226; 10,016,221; 10,004,538; 10,004,449; 9,999,519; 9,999,416; 9,987,024; 9,981,071; 9,980,780; 9,968,573; 9,968,376; 9,962,204; 9,956,010; 9,956,003; 9,949,731; 9,943,418; 9,937,062; 9,936,994; 9,925,060; 9,918,849; 9,913,734; 9,889,020; 9,888,928; 9,877,846; 9,872,709; 9,861,446; 9,855,075; 9,848,995; 9,848,914; 9,844,335; 9,839,374; 9,833,335; 9,827,108; 9,814,590; 9,814,499; 9,808,351; 9,808,346; 9,801,729; 9,801,640; 9,801,639; 9,801,546; RE46,582; 9,795,410; 9,795,399; 9,339,319; 7,141,015; 6,716,218; 6,315,780; 4,944,739; 4,475,544; CH653544; CN212755860u; CN212996697u.

SUMMARY OF THE INVENTION

The present invention provides a mechanism which enables a surgeon to easily achieve compression, distraction, and correction of angular deformity of bone fractures, osteotomies, deformities, and musculoskeletal joints of the spine, upper and lower extremities, skull, jaw, ribs, and pelvis. This mechanism enables a surgeon to independently control both the relative distances and relative angles of two bones or bone fragments.

This is achieved by a complex mechanism that provides a linked pair of quadrilateral linkages, sharing a common point. The quadrilateral linkages ensure that the bone fixation elements maintain their relative angle as they are proximated or displaced from each other. The common point is at the base of the screw actuator and corresponds to the scissor pivot axis. When the screw actuator is adjusted, the distance of the base of the screw actuator is altered with respect to a follower, which in turn changes the angle of the quadrilateral linkages. Therefore, the angle of the bone fixation elements is arbitrarily controlled by adjusting the screw, which alters the distance between the base of the screw and the follower, which in turn alters the aspect ratio of the quadrilaterals.

The arms may be separated by a spring mechanism, e.g., a flexural leaf spring, to release the compression of the feet when the ratchet is not engaged.

The quadrilaterals are defined by the common point pivot at the base of the screw, two pivots on lateral aspects of an element displaced by the follower, two pivots on the ends of the scissor mechanism, and two pivots which float between pairs of arms from the ends of the scissors mechanism and the lateral aspects of the displaced element.

The device is useful in a range of common orthopedic operations including, but not limited to, correction of bony malunions, fractures, or deformities in long bones, the reduction of fractures in the hands and feet, bunion surgery, discectomy and corpectomy, and the treatment of kyphosis or lordosis in the spine.

The adjustable angle orthopedic distractor and/or compressor according to the present technology allows the surgeon to perform multiple steps of the surgery, namely distraction, cleaning, compression, and fixation, with one handheld tool instead of multiple tools.

The technology allows the user to change the angle of two mounting feet during a procedure. By giving the surgeon control over the relative angle of the bone fragments, the tool provides better access to the joint surfaces while cleaning and ensures better alignment and compression of bones during fixation. Furthermore, the mechanism allows the user to adjust the relative angles of two mounting feet independently of their relative distance. This mechanism can be combined with a variety of tool bodies to address specific orthopedic applications.

The first series of embodiments, the Adjustable Angle Orthopedic Distractor and the Adjustable Angle Orthopedic Compressor, are intended to be used in the reduction of fractures in long bones such as the pediatric (or adult) femur and humerus. This procedure, an example of open reduction and internal fixation (ORIF) surgery, involves two steps: realignment of the bone fragments followed by fixation with wires, bone screws, and/or plates.

Several complications can arise from ORIF surgery, including malunion, delayed union, and nonunion of the bones. Malunion can occur when bones are improperly aligned during fixation, and results in delayed healing and curvature in the healed bone. One option permits the surgeon to first properly clean damaged tissue and debris from the fracture site. Another option facilitates collinear compression and accurate angular alignment of bone fragments across the fracture.

In the first set of embodiments, the relative distance of the mounting feet can be adjusted via manual compression of a pair of handles with a scissor mechanism. The compression force on the manual manipulator end passes through a pivot and is transferred as a contraction or distraction force between the mounting feet, depending on the configuration of the device. A second, independent control provides an axial displacement along a central plane of symmetry of the device and controls a relative angle of the mounting feet.

Compression of the handles allows transmission of a force through the inner bars and results in a corresponding contraction (in the case of the first option) or distraction (in the case of the second option) at the mounting feet. The first option has the handles cross in an X pattern such that each mounting foot is leveraged by a handle on the opposite side of the device, resulting in compression of the two bone fragments upon compression of the handles. In contrast, the second option has the handles meet at the central pivot point, but they do not cross, instead connecting to mounting feet on the same side of the tool, which permits distraction of the feet upon compression of the handles. Manipulation of the knob on the angular adjustment shaft moves the U-bar forward or backward and alters the quadrilateral geometry formed by the handles, outer bars, mounting feet, and U-bar. This shift in geometry produces a change in the relative angle of the mounting feet.

A ratchet may be provided at the rear of the compression handle embodiment to maintain the force after initial application, until the ratchet is released.

This technology may also be tailored for surgeries on small bones in the hands and feet. One such common procedure is the reduction of a Lisfranc fracture, in which misalignment of the midfoot joints (including the Lisfranc joint between the medial cuneiform and the second metatarsal) resulting from physical injury is corrected in a multi-step process. This procedure involves distraction of the dislocated bones in the midfoot and cleaning of the joint and fracture surfaces (i.e., removal of cartilage or damaged tissue), realignment of the bones, compression of the bones across the joint, and fixation with a combination of wires, screws, and/or plates.

Common complications that can occur after Lisfranc surgery are the development of arthritis and the formation of scar tissue in the fused joints. The first can occur due to insufficient removal of cartilage between the joints, which allows remaining cartilage to become inflamed. The second can occur due to improper fusion resulting from the misalignment of bones or a lack of sufficient force across the joint when compressed. This leads to the formation of scar tissue at the bone interface, which weakens the healed bone and increases the potential for refracture.

The device may provide two screw mechanisms to control the relative angle and distance between the feet, respectively. This embodiment of the device takes advantage of a dual-knob system with a mechanism to both compress and distract bone fragments, as well as independently adjust their relative angle. This design provides precise positioning and alignment of the bones, and does not require a ratchet, but takes more time to position than a ratchet due to the need for multiple turns of the screws.

The two handles connect with each other and with each mounting foot and are responsible for transmitting force to each mounting foot. Outer parallel bars connect with a central U-bar and to each mounting foot and permit the application of torsional force to each mounting point. The dual-knob system consists of a separation adjustment shaft and an angular adjustment shaft, with a separation adjustment shaft knob and an angular adjustment shaft knob to adjust the relative distance or angle, respectively, of the mounting feet. These rods are connected orthogonally with a central slider that permits translation of the separation adjustment shaft only along the angular adjustment shaft. The separation adjustment shaft has a pair of mirrored threads (clockwise and counterclockwise) and one fixed knob; rotation of this rod moves the threaded catches closer together or farther apart, transmitting a force through the inner bars and resulting in a corresponding contraction or distraction at the mounting feet.

In order to provide visual access to the operative field, the feet may be offset from a plane defined by the arms, or inclined.

Additionally, a bone plate may be provided at the working end closest to the mounting feet and would be placed onto the bone fragments prior to alignment of the bones. This bone plate would consist of a metal implant with two long slots in the center and screw holes on both sides. To enable the above-described devices to work in conjunction with such a bone plate, the mounting feet on each device would have removable bone screws that fit through the central slots. The central slots allow the user to first place bone screws partially into the two bone fragments and then adjust the relative angle of the bone fragments by manipulation of the angular adjustment shaft mechanism. After alignment of the bone fragments is achieved, additional bone screws would be placed into the bone fragments through the screw holes on either side of the bone plate, effectively fixing the bone plate to the aligned bone fragments and joining the fragments together. The device would then be removed from the surgical space by detaching it from the central slot screws.

As an asymmetric alternative to the symmetric designs discussed above, a further iteration of the tool comprises a main handle with a fixed mounting foot positioned on the working end at a preset (or manually adjustable) angle and four different configurations for adjustment of the relative distance of the mounting feet: a ratchet mechanism (for distraction or compression) and a screw mechanism (for distraction or both distraction and compression). In all four configurations, the device features a rack-and-pinion mechanism with a linkage, e.g., quadrilateral linkage, that connects to an adjustable mounting foot. An L-shaped bracket attaches a worm gear to the rack-and-pinion mechanism and connects it to the quadrilateral linkage. The rack-and-pinion mechanism is driven by rotation of a worm gear via a key, wrench, screwdriver, or other twisting driver. This mechanism permits adjustment of the relative angle of the mounting feet through rotation of the adjustable mounting foot.

In the two ratchet configurations, the adjustable handle is connected to the main handle via a joint that pivots. Compression of the adjustable handle allows transmission of a force that results in a corresponding separation (or proximation) of the adjustable mounting foot relative to the fixed mounting foot. A non-crossed set of handles and ratchet mechanism may be provided to control distraction of the bone, or a crossed set of handles and ratchet mechanism may be provided to control compression of the bone.

In the two screw configurations, the threaded rod is attached to the main handle via an anchor that pivots to accommodate the angle changes of the adjustable handle relative to the main handle during compression or distraction. In the first screw configuration, a threaded knob is manually rotated and translated along the axis of the screw until it reaches a follower, at which it begins to exert a force on the adjustable handle resulting in a corresponding separation of the mounting feet. The second screw configuration features the same knob that can be manually rotated to translate it along the axis of the screw, except that it is flanked on both sides by followers. In addition to separation of the mounting feet caused by translation towards the follower on the adjustable handle, translation of the knob towards the follower at the end of the screw causes a force to be exerted on the adjustable handle that results in the corresponding proximation of the mounting feet. Thus, this second configuration of the screw mechanism enables both compression and distraction of the bones. In both configurations, the screw can be released from the follower(s) and rotated out of the place of the scissors mechanism to enable cleaning of the threading.

As an asymmetric alternative to the symmetric designs discussed above, a further iteration of the tool comprises a main handle with a fixed mounting foot positioned on the working end at a preset (or manually adjustable) angle and two different configurations for adjustment of the relative distance of the mounting feet: a ratchet mechanism and a screw mechanism. In both configurations, the device features a rack-and-pinion mechanism with a linkage, e.g., quadrilateral linkage, that connects to an adjustable mounting foot. An L-shaped bracket attaches a worm gear to the rack-and-pinion mechanism and connects it to the quadrilateral linkage. The rack-and-pinion mechanism is driven by rotation of a worm gear via a key, wrench, screwdriver, or other twisting driver. This mechanism permits adjustment of the relative angle of the mounting feet through rotation of the adjustable mounting foot.

In the ratchet-mechanism configuration, the adjustable handle is connected to the main handle via a joint that pivots. Compression of the adjustable handle allows transmission of a force that results in a corresponding separation of the adjustable mounting foot relative to the fixed mounting foot. A non-crossed set of handles and ratchet mechanism may be provided to control distraction of the bone, or a crossed set of handles and ratchet mechanism may be provided to control compression of the bone.

In the screw-mechanism configuration, the threaded rod is attached to the main handle via a joint that allows it to pivot to accommodate the angle changes of the adjustable handle relative to the main handle during compression or distraction. A counter-threaded knob permits translation of a screw follower along the axis of the screw, resulting in a corresponding separation or proximation of the mounting feet. Thus, this mechanism enables both compression and distraction of the bones, as opposed to one or the other with a ratchet.

A modification of this device, in which the angle of the fixed mounting foot can be adjusted, such as with a screw or gear, would provide dual maneuverability for the mounting feet, as opposed to adjustability of a single mounting foot. An additional modification of this device could be included in which a mechanism allows the fixed mounting foot to be translated along the axis of the main handle, such as with a sliding bar. The addition of this mechanism would provide means by which the user could account for any offset in the relative position of the feet in the orthogonal axis, thereby increasing the precision of alignment of two bone fragments.

The above-discussed embodiments could be used in surgeries on the spine. Two applications for these devices would be in corpectomy (using, e.g., a device with knob controls for adjustment of both foot separation and foot angle); and anterior cervical discectomy and fusion, or ACDF (using, e.g., a device with a manual compression control for foot separation and knob for foot angle). Corpectomy is a surgical excision of part or all of a vertebral body, which is performed in cases of serious compression of the spinal cord and nerve, where a large degree of decompression is necessary. ACDF is one of the most common surgeries in spinal procedures to relieve minor compression on the spinal cord and nerve and involves the removal of one or more intervertebral disc(s) in the spine.

In corpectomy, the tips of Caspar pins are screwed into the midline of the vertebral bodies above and below the vertebral body to be excised. By placing a distractor on these pins, a surgeon can separate the adjacent vertebrae. This allows for the removal of the vertebral body, discs, and cartilage, and the insertion of bone grafts or expandable cages. Current distractors do not allow for adjustment of the angle of these pins, impeding vertebral body, disc, and cartilage removal as well as alignment.

A common risk of corpectomy is placing excessive stress on the spinal cord and nerves during distraction of the vertebrae. The use of the dual-knob embodiment or the screw configuration of the asymmetric embodiment would allow a surgeon to precisely control the distance and angle of the vertebrae, resulting in less stress placed on the nerves and spinal cord, thereby reducing the risk of injury to the patient. Precise control over the angle comes with the added benefit of allowing surgeons to control for kyphosis and lordosis and correct improper angulation of the fused vertebrae.

The devices would likewise prove useful in ACDF procedures. As in a corpectomy, the use of these devices would allow the surgeon to distract the vertebral bodies and adjust their relative angle such that the intervertebral disc can be removed, and an artificial disc or bone graft can be inserted.

The sizes of each of the devices can be scaled to meet the needs of the specific use case, with smaller sizes for more delicate small bone procedures and larger sizes for procedures involving larger bones. A range of sizes may be provided to ensure that the forces applied by the tool are sufficient to adequately distract and/or compress the bones in each use case.

The mounting feet at the front end of the tool may be modular and interchangeable such that different mounting foot sizes, hole sizes, and hole types can be used for specific applications. The mounting feet may have recesses which engage with the heads of bone screws and, after alignment of the bones and affixation of the screws, may be disengaged from the screws. Modular mounting feet would also allow for a left-handed surgeon to have the feet oriented in the opposite direction as those for a right-handed surgeon to make the device compatible with either handedness. In addition, a U-shaped configuration of the mounting feet would allow for a large offset of the body of the tool from the incision site to prevent intrusion in the wound or obstruction of the surgical space by the tool body.

The bone plate at the front end of the tool may be modular and interchangeable such that different bone plate sizes, hole sizes, and hole types can be used for specific applications. In addition, the bone screws may be interchangeable such that different bone screw sizes and types can be used for specific applications and to accommodate different types of bone plates.

These devices should be made from austenitic 316 stainless or martensitic 420 or 440 surgical stainless steel due to their strength, corrosion resistance, and ease of sterilization. This material is commonly used for medical devices and may be machined in order to produce the various components of the tool. No plating is required on the metal and the surface may be smooth.

Since these tools are constructed using surgical-grade stainless steel, they can be subjected to a wide variety of sterilization methods to ensure adequate cleaning of the tool after each use. These devices may be sterilized using high heat and pressure (such as those used in gravity-displacement autoclaves), sodium hydroxide, enzymatic or detergent cleaners, and ultrasonic sterilization, without danger of corrosion, wear, or damage to the components. In order to remove trapped tissue and debris in crevices and joints of the instruments, these tools should be partially disassembled and certain parts manually cleaned.

Small grooves in the threaded components require particular attention during sterilization and cleaning, so these components are designed to be easily removed.

To sanitize the separation adjustment shaft, the knob is removed and the handles separated until the ends of the handles release from the separation adjustment shaft. The separation adjustment shaft can then be unclipped from the central slider. The separation adjustment shaft can be cleaned by hand and replaced onto the tool by putting it back into the central slider and allowing the threaded catches to be rethreaded onto either end of the rod.

In an alternate embodiment with a worm and rack adjustment mechanism (see FIGS. 14 and 15), the pin 307, for example, may be removable, to permit the mechanism to be disassembled for cleaning.

The angular adjustment shaft can also be cleaned and sterilized. The angular adjustment shaft has a ball joint at its base and is removed by aligning cutouts on the U-bar and central follower (slider) with paired grooves on the angular adjustment shaft. When the cutout is properly aligned with the slot, the angular adjustment shaft can pivot away from the plane of the tool about a ball joint. Because this procedure requires the angle and distance of the mounting feet to be much greater than the working range of the tool during surgery, there is no danger of the rod being released outside of a cleaning procedure. Once cleaned, the angular adjustment shaft can be slotted back in. To place the rod back onto the device, it is rotated back onto the central slider and the knob is turned clockwise until the angular adjustment shaft catches the threading on the U-bar, restoring the function of the knob mechanism to adjust the relative angle of the mounting feet.

It is therefore an object to provide an orthopedic instrument for angular and displacement control of bone, comprising: a pair of pivotally-connected arms, extending beyond a pivot axis of a first pivot; a pair of feet having a displacement controlled by the pair of pivotally-connected arms, at least one foot being pivotally mounted, the pair of feet being configured for affixation to respective portions of bone; an adjustment configured to control a relative orientation of the pair of feet; and a mechanism configured to maintain the relative orientation of the pair of feet over a range of displacement controlled by the pair of pivotally-connected arms.

The adjustment may comprise a screw, and the mechanism comprise a screw follower displaced by the screw, linked to a displaceable side of a quadrilateral linkage.

The mechanism may comprise a first fitting, proximate to the first pivot, for retaining an axial element; a second fitting, displaced from the first fitting, wherein a manipulation of the axial element by the adjustment alters a distance between the first fitting and the second fitting; a second pivot on an end of a pivotally-connected arm extending beyond the first pivot; one of the feet being pivotally mounted by the second pivot to the end of one of the pair of pivotally-connected arms extending beyond the first pivot; a third pivot each linked to the second fitting, and being laterally displaced from a plane (a bisecting symmetric plane, in a symmetric embodiment, or in an asymmetric embodiment, from an axis which intersects the pivot connecting the arms and provides one foot on each side of the axis) of the pair of pivotally-connected arms; a fourth pivot on the pivotally mounted foot, laterally displaced from the second pivot from the central plane of symmetry; and a lateral arm linking the third pivot and the fourth pivot, wherein the first pivot, second pivot, third pivot and fourth pivot define vertices of a quadrilateral, and the pivotally-connected arm extending beyond the first pivot, the feet, the lateral arm, and the second fitting representing the sides of the quadrilateral.

The mechanism may comprise a first fitting, proximate to the first pivot, for retaining an axial element; a second fitting, displaced from the first fitting, wherein a manipulation of the axial element by the adjustment alters a distance between the first fitting and the second fitting; a pair of second pivots on ends of the pair of pivotally-connected arms extending beyond the first pivot; the pair of feet being pivotally mounted by the pair of second pivots to the ends of the pair of pivotally-connected arms extending beyond the first pivot; a pair of third pivots each linked to the second fitting, and being laterally displaced from a bisecting plane of the pair of pivotally-connected arms; a pair of fourth pivots on the pair of feet, laterally displaced from the pair of second pivots from the central plane of symmetry; and a pair of lateral arms linking the third pivots and the fourth pivots, on the same side of the central plane of symmetry, wherein the first pivot, second pivots, third pivots and fourth pivots define vertices of a pair of linked quadrilaterals sharing the first pivot, and the pivotally-connected arms extending beyond the first pivot, the feet, the pair of lateral arms, and the second fitting representing the sides of the pair of linked quadrilaterals.

It is also an object of the invention to provide an orthopedic instrument for aligning and proximating or displacing bone, comprising: a pair of pivotally-connected arms, extending beyond a pivot axis of a first pivot and defining a central plane of symmetry; a first fitting, proximate to the first pivot, for retaining an axial element; a second fitting, displaced from the first fitting, wherein a manipulation of the axial element alters a distance between the first fitting and the second fitting; a pair of second pivots on ends of the pair of pivotally-connected arms extending beyond the first pivot; a pair of feet pivotally mounted by the pair of second pivots to the ends of the pair of pivotally-connected arms extending beyond the first pivot; a pair of third pivots each linked to the second fitting, and being laterally displaced from the central plane of symmetry; a pair of fourth pivots on the pair of feet, laterally displaced from the pair of second pivots from the central plane of symmetry; and a pair of lateral arms linking the third pivots and the fourth pivots, on the same side of the central plane of symmetry, wherein the first pivot, second pivots, third pivots and fourth pivots define vertices of a pair of linked quadrilaterals sharing the first pivot, and the pivotally-connected arms extending beyond the first pivot, the feet, the pair of lateral arms, and the second fitting representing the sides of the pair of linked quadrilaterals.

It is also an object to provide an orthopedic instrument, comprising: a pair of pivotally-connected arms, extending beyond a pivot axis of a first pivot and defining a central plane of symmetry; a pair of feet mounted to ends of the pair of pivotally-connected arms; and a quadrilateral linkage configured to maintain parallelism between the pair of feet over a range of angles and to selectively alter a distance between the pair of feet. The orthopedic instrument may comprise a first fitting, proximate to the first pivot, for retaining an axial element; a second fitting, displaced from the first fitting, wherein a manipulation of the axial element alters a distance between the first fitting and the second fitting; a pair of second pivots on ends of the pair of pivotally-connected arms extending beyond the first pivot; the pair of feet being pivotally mounted by the pair of second pivots to the ends of the pair of pivotally-connected arms extending beyond the first pivot; a pair of third pivots each linked to the second fitting, and being laterally displaced from the central plane of symmetry; a pair of fourth pivots on the pair of feet, laterally displaced from the pair of second pivots from the central plane of symmetry; and a pair of lateral arms linking the third pivots and the fourth pivots, on the same side of the central plane of symmetry, wherein the quadrilateral linkage comprises the first pivot, second pivots, third pivots and fourth pivots define vertices of a pair of linked quadrilaterals sharing the first pivot, and the pivotally-connected arms extending beyond the first pivot, the feet, the pair of lateral arms, and the second fitting representing the sides of the pair of linked quadrilaterals.

The distance between the pair of feet is controlled by rotation of a threaded rod or compression of two handles. The relative angle between the pair of feet is controlled by rotation of a threaded rod or rotation of a worm gear on a rack-and-pinion mechanism.

The quadrilateral linkage may comprise a pair of quadrilateral linkages, each having rigid arms connected by pivots, which share a common pivot.

A compression of the arms on one side of the pivot may separate or alternately compress the pair of feet.

The pair of pivotally-connected arms may act across the central plane of symmetry, such that compression on one side of the first pivot causes compression on the other side of the first pivot. The pair of pivotally-connected arms may act on respective sides of the central plane of symmetry, such that compression on one side of the first pivot causes expansion on the other side of the first pivot.

The pair of pivotally-connected arms may also be hinged asymmetrically, such that one is static (i.e., one foot and corresponding handle remain in fixed relative position) whereas the other moves (i.e., the angle and displacement of the foot to the supporting handle changes along with a change in the relative angle and displacement of the handles), such that compression on the moving arm causes a distraction force relative to the static arm.

The orthopedic instrument may further comprise a ratchet configured to retain unidirectional displacement of the pair of pivotally-connected arms until released.

The orthopedic instrument may further comprise a screw configured to control a displacement of the pair of pivotally-connected arms.

The feet may each comprise at least one hole or slot for retaining a bone pin or screw.

The follower may comprise a U-shaped member, which maintains the pair of third pivots laterally displaced from the central plane of symmetry and proximal to the first fitting with respect to a contact region of the second fitting with the axial element.

The axial element may comprise a screw, and the second fitting comprises a screw follower.

On each side of the central plane of symmetry, the first pivot and each third pivot may define a line parallel to a line defined by the second pivot and fourth pivot. On each side of the central plane of symmetry, the first pivot and each second pivot may define a line parallel to a line defined by the third pivot and fourth pivot.

The first fitting may comprise a ball joint that retains the axial element while permitting rotation when the axial element is aligned with the central plane of symmetry, and permitting release of the axial element when inclined away from the central plane of symmetry.

The second fitting may comprise a slot, configured to follow a screw thread on the axial element when the axial element is aligned with the central plane of symmetry, and to permit the axial element to incline away from the central plane of symmetry.

The axial element may be centered between the pair of pivotally-connected arms in the central plane of symmetry by a pair of arms and a sleeve.

The orthopedic instrument may further comprise a transverse screw configured to control a displacement of the pair of pivotally-connected arms, wherein the axial element is centered between the pair of pivotally-connected arms in the central plane of symmetry by a sleeve riding on the transverse screw. The transverse screw may be mounted on ends of the pair of pivotally-connected arms through a pair of fifth pivots to a pair of third fittings.

It is also an object to provide an orthopedic instrument, comprising a pair of pivotally-connected arms, extending beyond a pivot axis of a first pivot and defining a central plane of symmetry; a pair of feet mounted to ends of the pair of pivotally-connected arms; and a quadrilateral linkage configured to maintain parallelism between the pair of feet over a range of angles and to selectively alter a distance between the pair of feet.

The distance between the pair of feet may be controlled by rotation of a first threaded rod and the relative angle between the pair of feet is controlled by rotation of a second threaded rod.

The quadrilateral linkage may comprise a pair of quadrilateral linkages, each having rigid arms connected by pivots, which share a common pivot.

The orthopedic instrument may further comprise: a first fitting, proximate to the first pivot, for retaining an axial element; a second fitting, displaced from the first fitting, wherein a manipulation of the axial element alters a distance between the first fitting and the second fitting; a pair of second pivots on ends of the pair of pivotally-connected arms extending beyond the first pivot; the pair of feet being pivotally mounted by the pair of second pivots to the ends of the pair of pivotally-connected arms extending beyond the first pivot; a pair of third pivots each linked to the second fitting, and being laterally displaced from the central plane of symmetry; a pair of fourth pivots on the pair of feet, laterally displaced from the pair of second pivots from the central plane of symmetry; and a pair of lateral arms linking the third pivots and the fourth pivots, on the same side of the central plane of symmetry, wherein the quadrilateral linkage comprises the first pivot, second pivots, third pivots and fourth pivots define vertices of a pair of linked quadrilaterals sharing the first pivot, and the pivotally-connected arms extending beyond the first pivot, the feet, the pair of lateral arms, and the second fitting representing the sides of the pair of linked quadrilaterals.

It is a further object to provide a method of aligning bone, comprising: providing an instrument comprising: a pair of pivotally-connected arms, extending beyond a pivot axis of a first pivot and defining a central plane of symmetry; a pair of feet mounted to ends of the pair of pivotally-connected arms; and a quadrilateral linkage configured to maintain a relative orientation between the pair of feet over a range of angles and to selectively alter a distance between the pair of feet; affixing the pair of feet to sections of bone; adjusting the quadrilateral linkage to define a relative orientation between the pair of feet; and adjusting a displacement of the pair of feet, to thereby relocate the portions of bone.

BRIEF DESCRIPTION OF THE DRAWINGS

FIG. 13 shows a front view of the small orthopedic compressor with the scissor hinge and two screw adjustments as shown in FIG. 10, after alignment of bone and placement of the bone plate;

FIG. 14 shows a top view of the small orthopedic compressor with the scissor hinge and two screw adjustments as shown in FIG. 13, after alignment of bone and placement of the bone plate;

FIGS. 32-40B show a compressor embodiment with feet angled with respect to the pivot axis, arms which are uncrossed, and a ratcheting mechanism to maintain separation of the feet. A longitudinal screw mechanism controls the relative angle of the feet.

FIGS. 50-60B show a compressor-distractor embodiment with feet angled with respect to the pivot axis, arms which are crossed, and a helical screw mechanism to control separation of the feet. A longitudinal screw mechanism controls the relative angle of the feet.

DETAILED DESCRIPTION OF THE PREFERRED EMBODIMENTS

Figure 1:
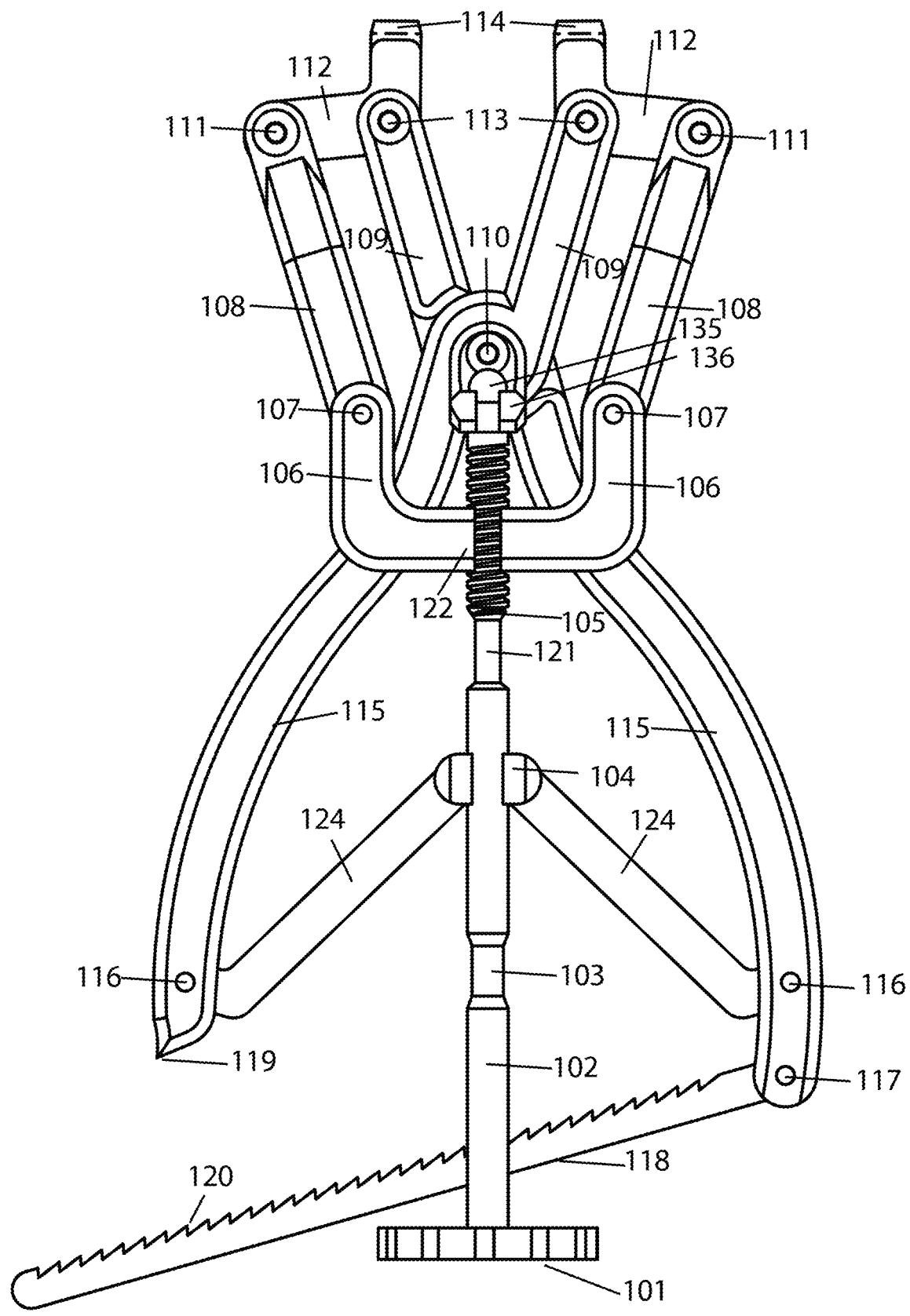
FIG. 1 shows a front view of a large orthopedic compressor with a scissor hinge and a screw adjustment.

The figures show various embodiments of the invention.

In general, to achieve bone compression, the handles are crossed in a scissor linkage, so that a compression of the handle leads to a corresponding compression of the operative legs of the device. To achieve distraction, the handles are uncrossed and have a linking pivot, so that a compression of the handle leads to a corresponding separation (distraction) of the operative legs of the device. However, if the displacement of the operative legs of the device is driven by a threaded rod, then distraction and compression may be achieved by the same device. Of course, other convenient simple mechanisms may be used to define the separation of the feet.

Therefore, the present technology provides an embodiment which is a distractor-compressor, having a distance between the feet bidirectionally controlled by action of a threaded rod on a follower; an embodiment which is a distractor, and acts to separate the bone; and an embodiment which is a compressor, that serves to proximate bone. Each of the embodiments has separate and independent control over the angle of the feet, which are affixed to the separate bones (or portions of a fractured or cut bone) when in use, and the distance between the feet.

Each of the embodiments provides a pair of pivotally-connected arms, extending beyond a pivot axis of a first pivot. The devices may be generally symmetric, or asymmetric.

A first fitting is provided proximate to the first pivot, for retaining an axially displaceable element, which is, for example, a threaded rod which sits in a threaded orifice.

A second fitting is provided, displaced from the first fitting, wherein a manipulation of the axially displaceable element alters a distance between the first fitting and the second fitting. Thus, for example, the end of the threaded rod is retained, such that a rotation of the threaded rod causes the first fitting to ride up or down the threaded rod.

A second pivot (or pair of pivots) is provided on end or ends of one or both pivotally-connected arms extending beyond the first pivot. One or both of the pair of feet are pivotally mounted by the second pivot(s) to the ends of the pivotally-connected arm(s) extending beyond the first pivot. A third pivot or pair of third pivots are also provided, each linked to the second fitting, and being laterally displaced from the central plane of symmetry. Advantageously, the third pivot(s) are longitudinally spaced from the first pivot by an element. In a symmetric embodiment with a pair of second pivots and third pivots, the element may be a U-shaped member.

A fourth pivot or pair of fourth pivots is provided on the foot or pair of feet, laterally displaced from the second pivot(s) from a longitudinal axis extending through the central pivot, or alternately, having been inclined with respect to a plane defined by the lateral arms.

A lateral arm or pair of lateral arms linking the third pivot(s) and the fourth pivot(s) are provided, on the same side of the longitudinal axis.

The first pivot, second pivots, third pivots and fourth pivots thus define vertices of a quadrilateral linkage or a pair of linked quadrilaterals sharing the first pivot, and the pivotally-connected arms extending beyond the first pivot, the feet, the pair of lateral arms, and the second fitting representing the sides of the pair of linked quadrilaterals.

The instrument may be disassembled in two steps. First, the arms are separated to their maximum, and in the case of the first embodiment, the separation adjustment shaft is freed. Then, the axially mounted angular adjustment rod is inclined out of the plane of the device, and may then be disengaged.

FIGS. 1-4 show a large orthopedic compressor with a scissor hinge and a screw adjustment. A pair of handles 115, linked with a hinge 110, control a displacement of a pair of feet 114. The handles 115 are retained in a desired degree of displacement by a ratchet mechanism having a ratchet bar 118, which is hinged to one of the handles 115 with a pivot 117, and which is maintained by a spur 119.

The angle of the feet is adjusted by a screw 105, controlled by a knob 101, acting on a shaft 102 having a first notch 103 and a second notch 121. The screw 105 acts on a screw follower 122 to control an axial depth of a U-shaped link 106, which is part of a quadrilateral linkage which includes outer sides 108, inner sides 109, and distal sides 112. The quadrilateral linkage has pivots 107 between the U-shaped link 106 and the outer sides 108, pivots 111 between the outer sides 108 and the distal sides 112, pivots 113 between the distal sides 112 and the inner sides 109. The hinge 110 acts as a common pivot for both halves.

The shaft 102 is centered and retained by a pair of arms 124 attached to the handles 115 by pivots 116, meeting at a central retaining element 104. When the screw 105 is fully extended, the notch 103 aligns with the central retaining element, and the notch 121 aligns with the screw follower 122, allowing the shaft 102 to be angled out of the plane of the instrument on a ball joint having ball 135 and socket 136 to allow for, e.g., cleaning of the shaft 102.

Figure 2:
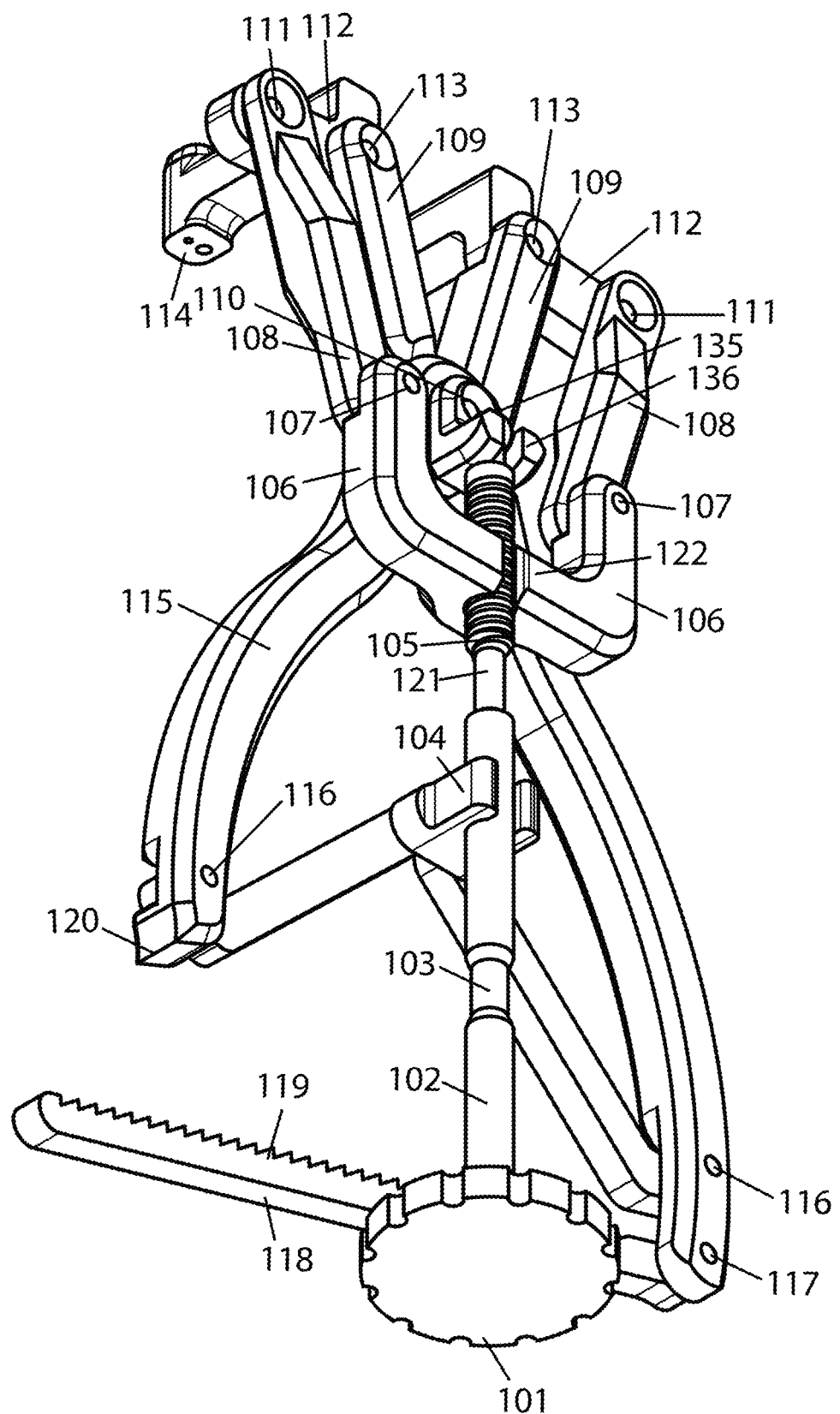
FIG. 2 shows a perspective view of the large orthopedic compressor with the scissor hinge.
Figure 3:
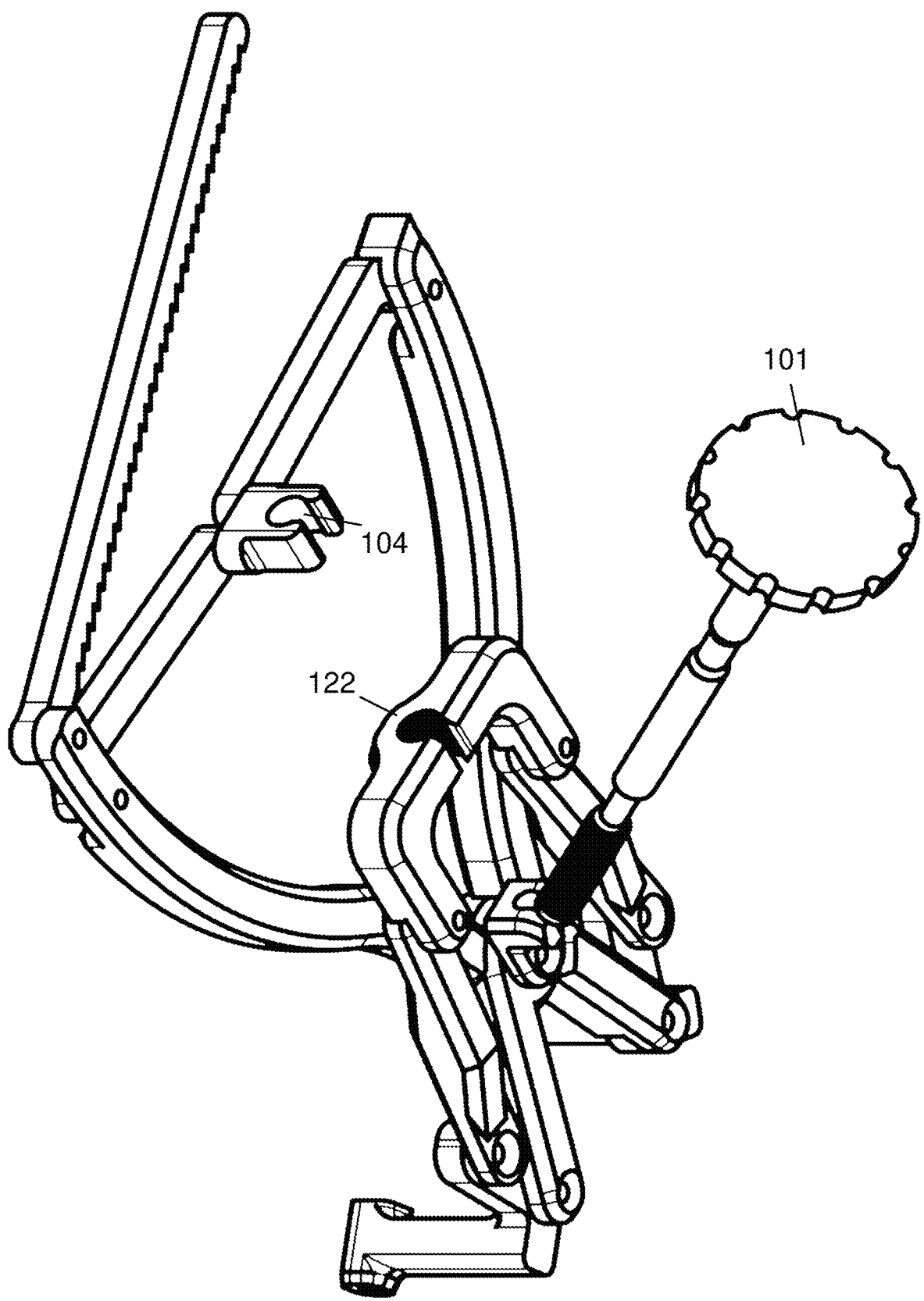
FIG. 3 shows a first perspective view of the large orthopedic compressor with the scissor hinge and an adjustment screw displaced from an operational position.
Figure 4:
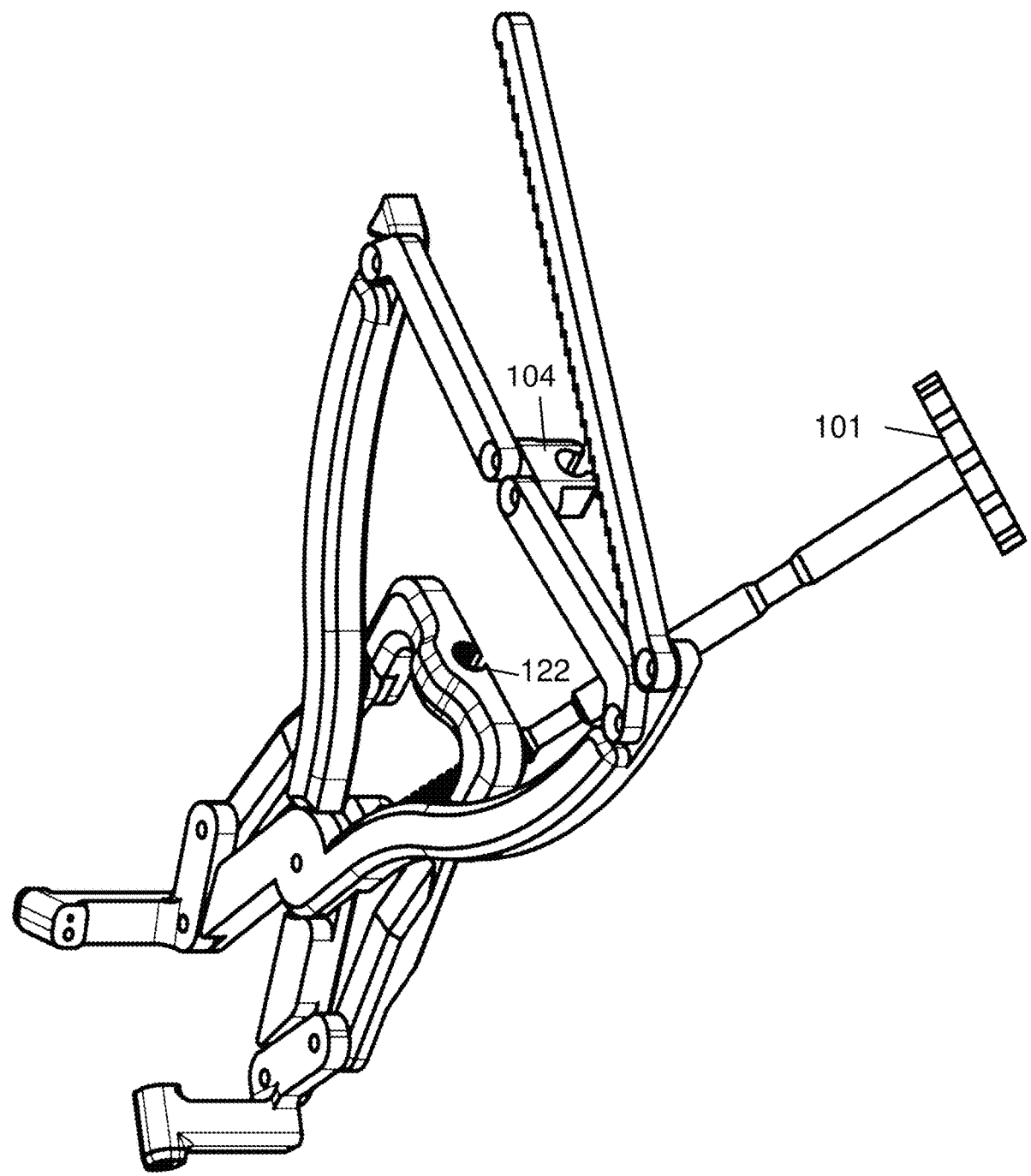
FIG. 4 shows a second perspective view of the large orthopedic compressor with the scissor hinge and an adjustment screw displaced from the operational position.

FIG. 1 shows a front view of a large orthopedic compressor in an operational state, and FIG. 2 shows a perspective view. FIGS. 3 and 4 show perspective views of the large orthopedic compressor with the adjustment screw displaced from an operational position, as described above.

Figure 5:
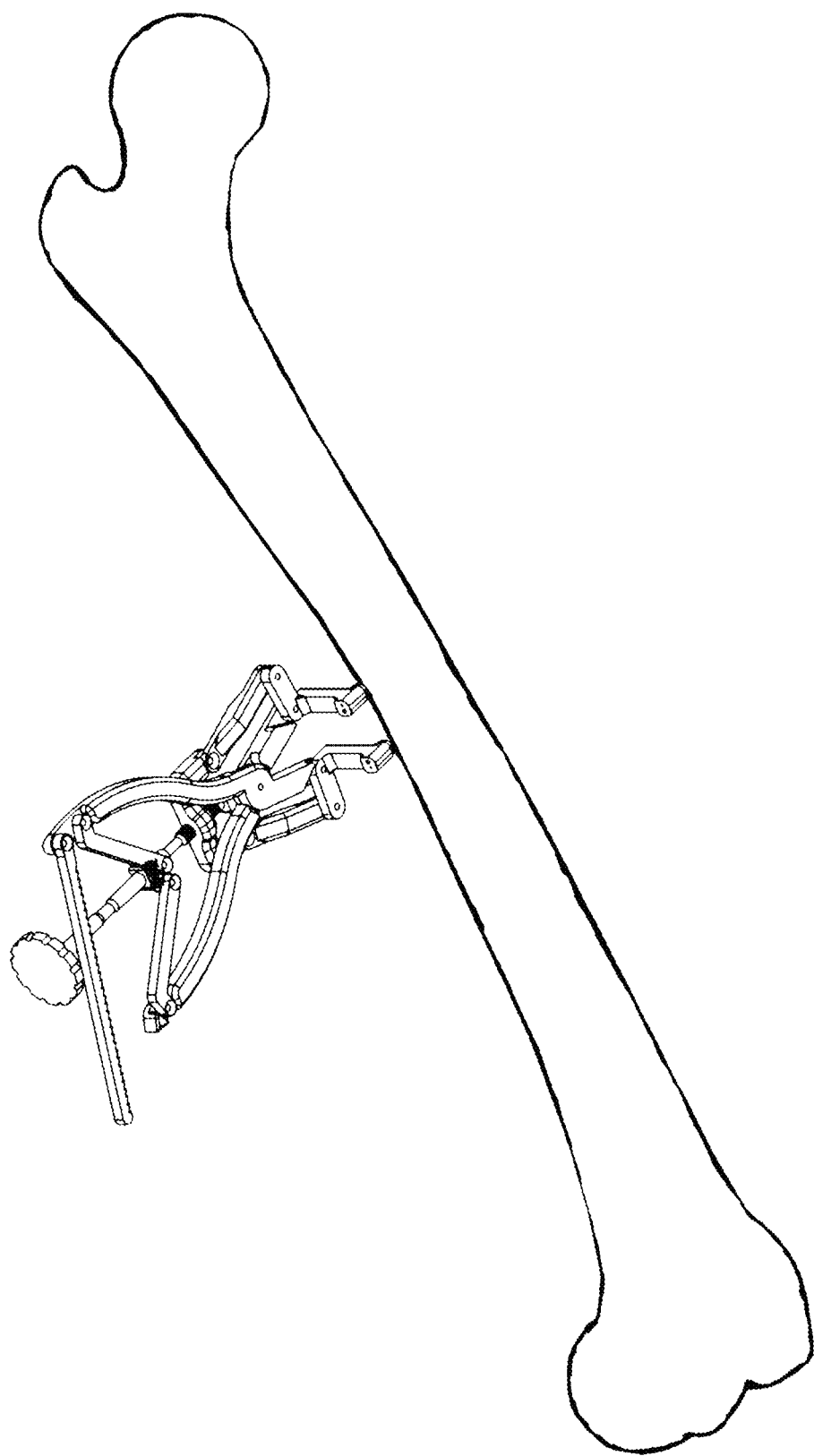
FIG. 5 shows a perspective view of the large orthopedic compressor according to FIGS. 1-4, in use to proximate portions of a femur.

FIG. 5 shows a perspective view of the large orthopedic compressor according to FIGS. 1-4, in use to proximate portions of a femur. In this case, the feet 114 are pinned to the bone, with the ends aligned and separated, and then the displacement of the portions of bone controlled by a displacement of the handles, with the angle of the portions maintained by the quadrilateral linkage.

Figure 6:
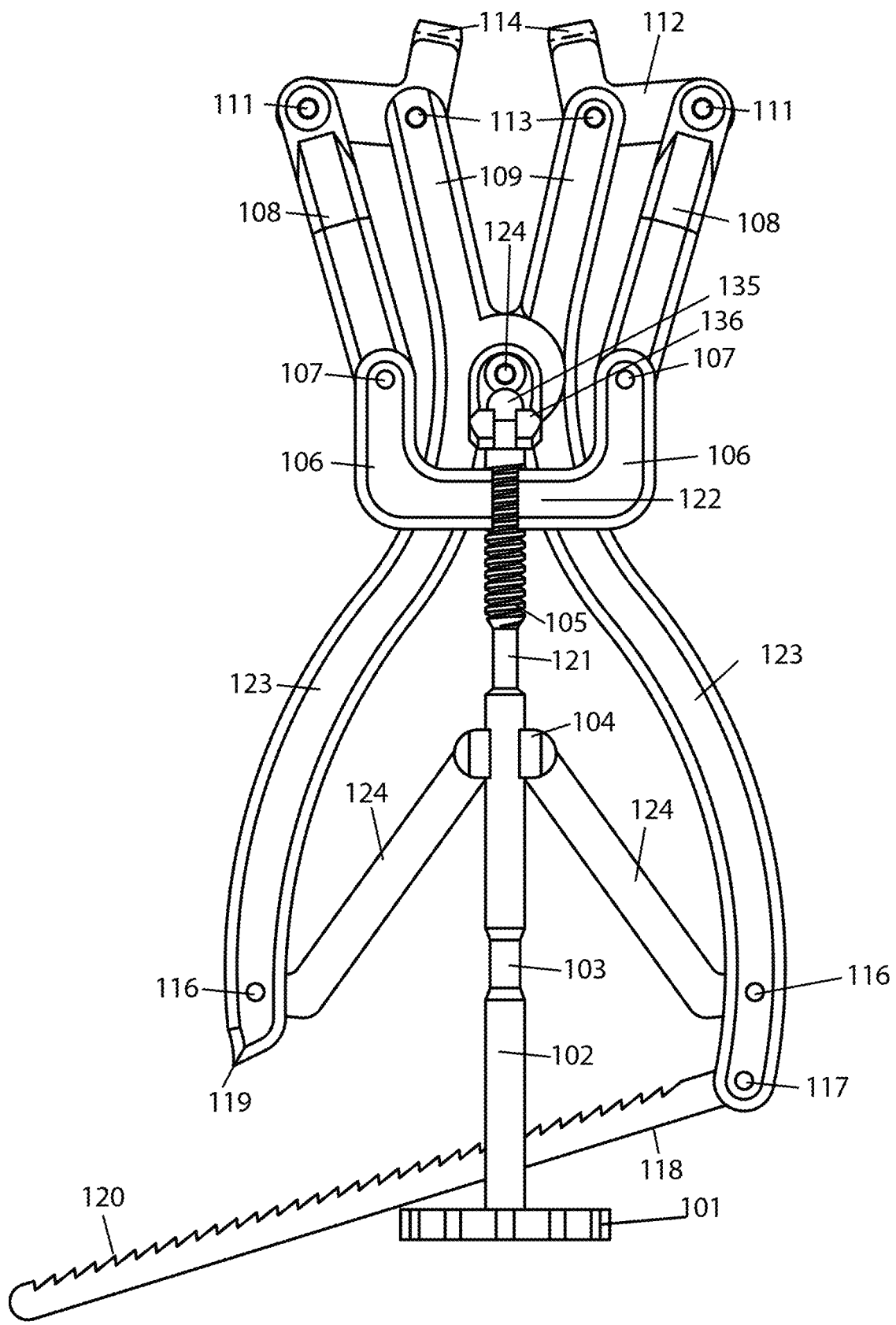
FIG. 6 shows a front view of a large orthopedic distractor, with an uncrossed hinge.
Figure 7:
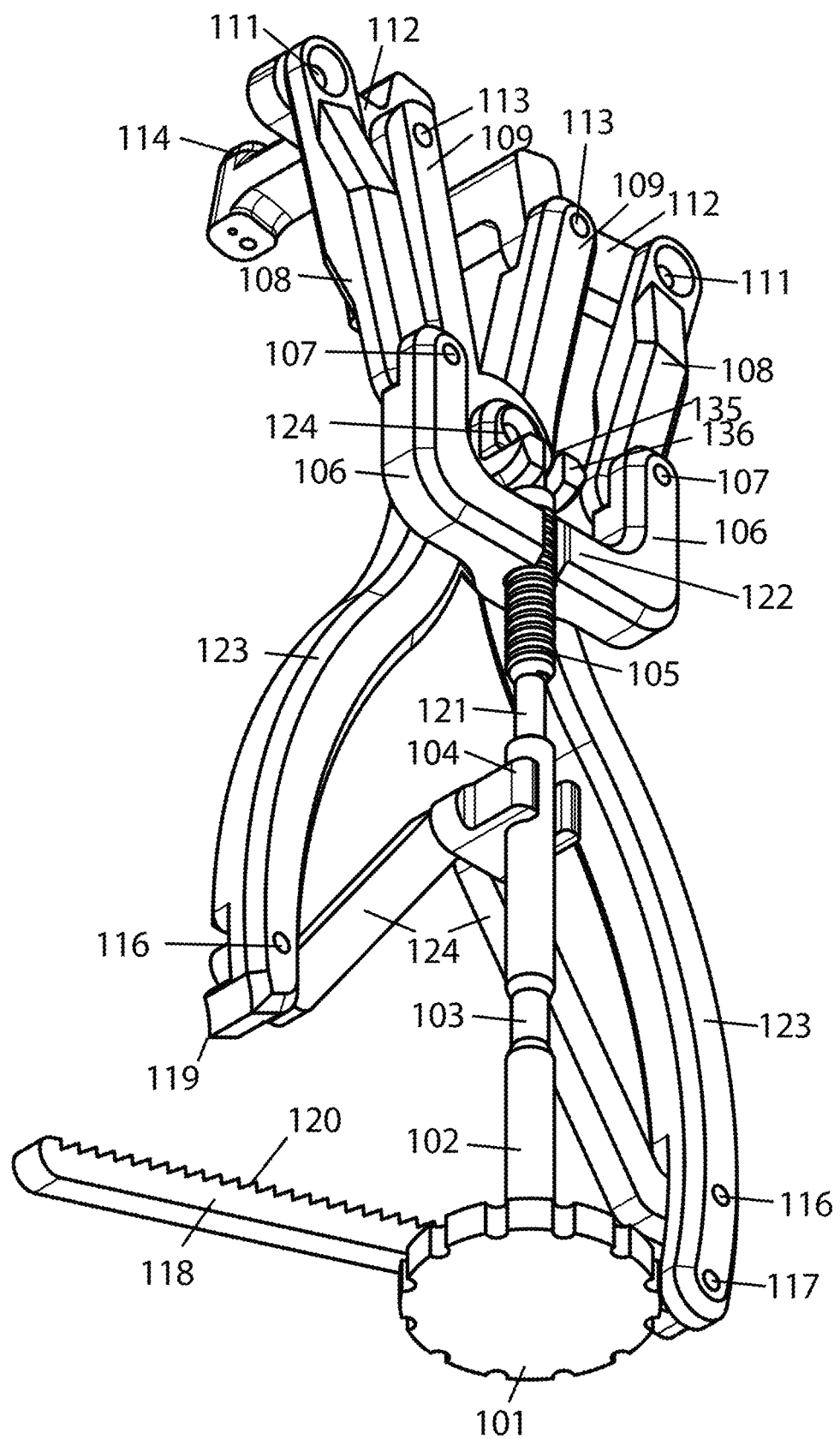
FIG. 7 shows a perspective view of the large distractor, with the uncrossed hinge.

FIGS. 6 and 7 show a large orthopedic distractor with a ratcheting mechanism and an uncrossed hinge, such that a compression of the handles separates the feet, in contrast to the embodiment shown in FIGS. 1-4, in which a compression of the handles causes the feet to compress.

A pair of handles 123, linked with a hinge 124, control a displacement of a pair of feet 114. The handles 123 are retained in a desired degree of displacement by a ratchet mechanism having a ratchet bar 118, which is hinged to one of the handles 115 with a pivot 117, and which is maintained by a spur 119.

The angle of the feet is adjusted by a screw 105, controlled by a knob 101, acting on a shaft 102 having a first notch 103 and a second notch 121. The screw 105 acts on a screw follower 122 to control an axial depth of a U-shaped link 106, which is part of a quadrilateral linkage which includes outer sides 108, inner sides 109, and distal sides 112. The quadrilateral linkage has pivots 107 between the U-shaped link 106 and the outer sides 108, pivots 111 between the outer sides 108 and the distal sides 112, pivots 113 between the distal sides 112 and the inner sides 109. The hinge 110 acts as a common pivot for both halves.

The shaft 102 is centered and retained by a pair of arms 124 attached to the handles 123 by pivots 116, meeting at a central retaining element 104. When the screw 105 is fully extended, the notch 103 aligns with the central retaining element, and the notch 121 aligns with the screw follower 122, allowing the shaft 102 to be angled out of the plane of the instrument on a ball joint having ball 135 and socket 136 to allow for, e.g., cleaning of the shaft 102.

FIGS. 8 to 15 show a small orthopedic compressor-distractor with a scissor hinge and two screw adjustments. The operation is similar to the embodiment of FIGS. 1-4, except the displacement of the handles is controlled by a second screw, no ratchet is required, and the second screw may be used to apply compressive or distractive forces.

The shaft 202 is centered and retained by a sleeve that rides on a second screw 230, having knob 231, and a pair of screw followers 233 linked to arms 224. A pair of handles arms 224, linked with a hinge 210, control a displacement of a pair of feet 214 by rotation of the screw 230, which is right hand threaded on one side, and left hand threaded on the other. Because the screw 230 is double threaded, rotation of the screw 230 causes a compression or distraction of the screw followers 233, which in turn apply a corresponding force on the arms 224 through the pivots 232. The screw followers 233 are attached to the arms 224 with pivots 232. The arms 224 are crossed, and the force is conveyed to the pivots 213, which compress or distract the distal sides 212, which are rigidly linked to the feet 214. Therefore, a compression of the screw followers 233 is converted into a compression of the feet 214.

The angle of the feet 214 is adjusted by a screw 205, controlled by a knob 201, acting on a shaft 202 having a notch 203. The screw 205 acts on a screw follower 204 to control an axial depth of a U-shaped link 206, which is part of a quadrilateral linkage which includes outer sides 208, inner sides 209, and distal sides 212. The quadrilateral linkage has pivots 207 between the U-shaped link 206 and the outer sides 208, pivots 211 between the outer sides 208 and the distal sides 212, pivots 213 between the distal sides 212 and the inner sides 209. The hinge 210 acts as a common pivot for both halves. As the U-shaped link 206 is raised or lowered with respect to the feet 214 by the rotation of the knob 201, the pivots 207, and outer side (lateral arms) 208 are also raised or lowered. Since the distal sides 212 are fixed by the pivots 213 holding the respective distal sides 212 to the respective arms 224, the angle of the distal sides 212 symmetrically changes with the adjustment.

Figure 8:
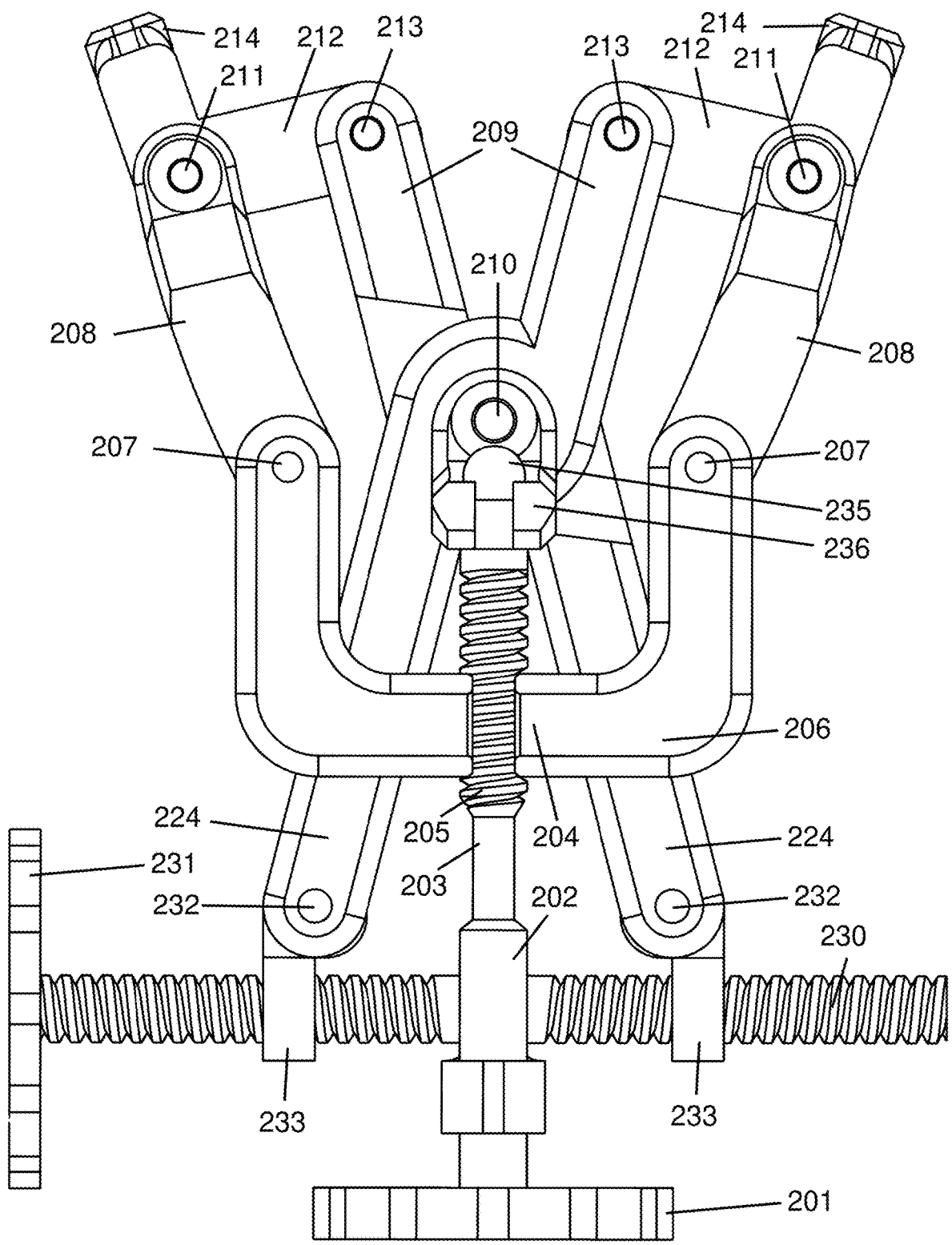
FIG. 8 shows a front view of a small orthopedic compressor with a scissor hinge and two screw adjustments.
Figure 9:
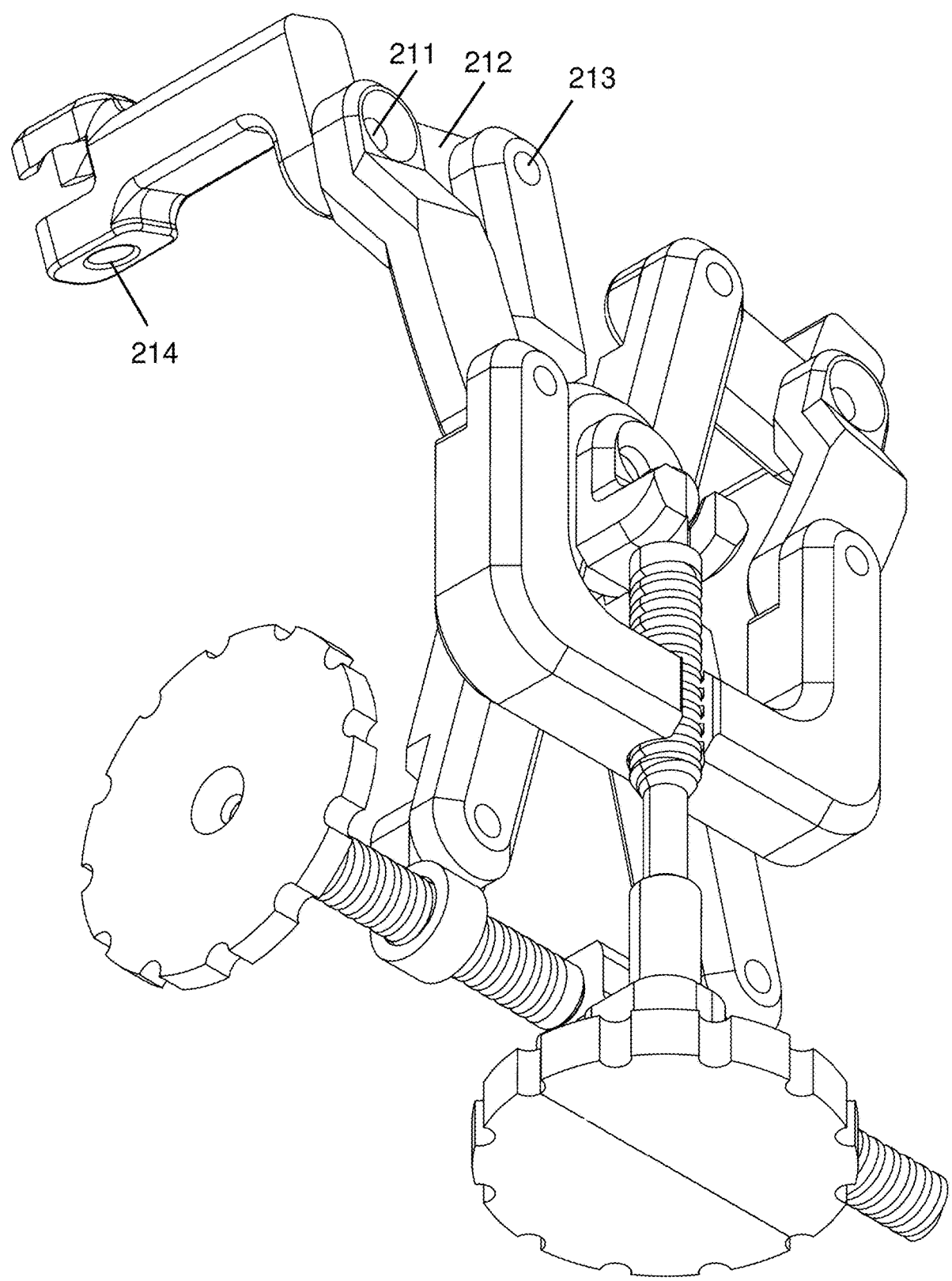
FIGS. 9 and 10 show perspective views of the small orthopedic compressor with the scissor hinge and two screw adjustments.
Figure 10:
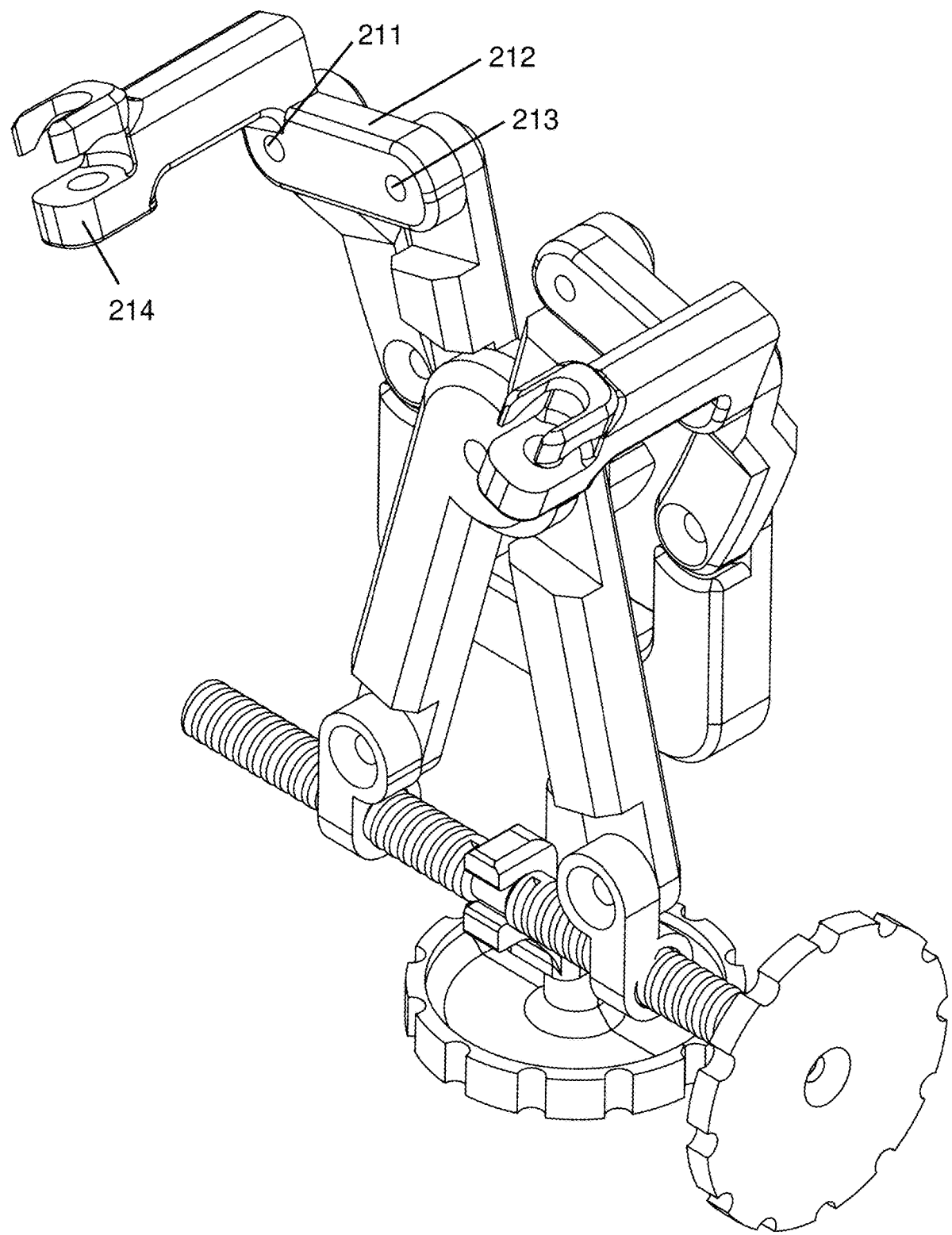
Figure 11:
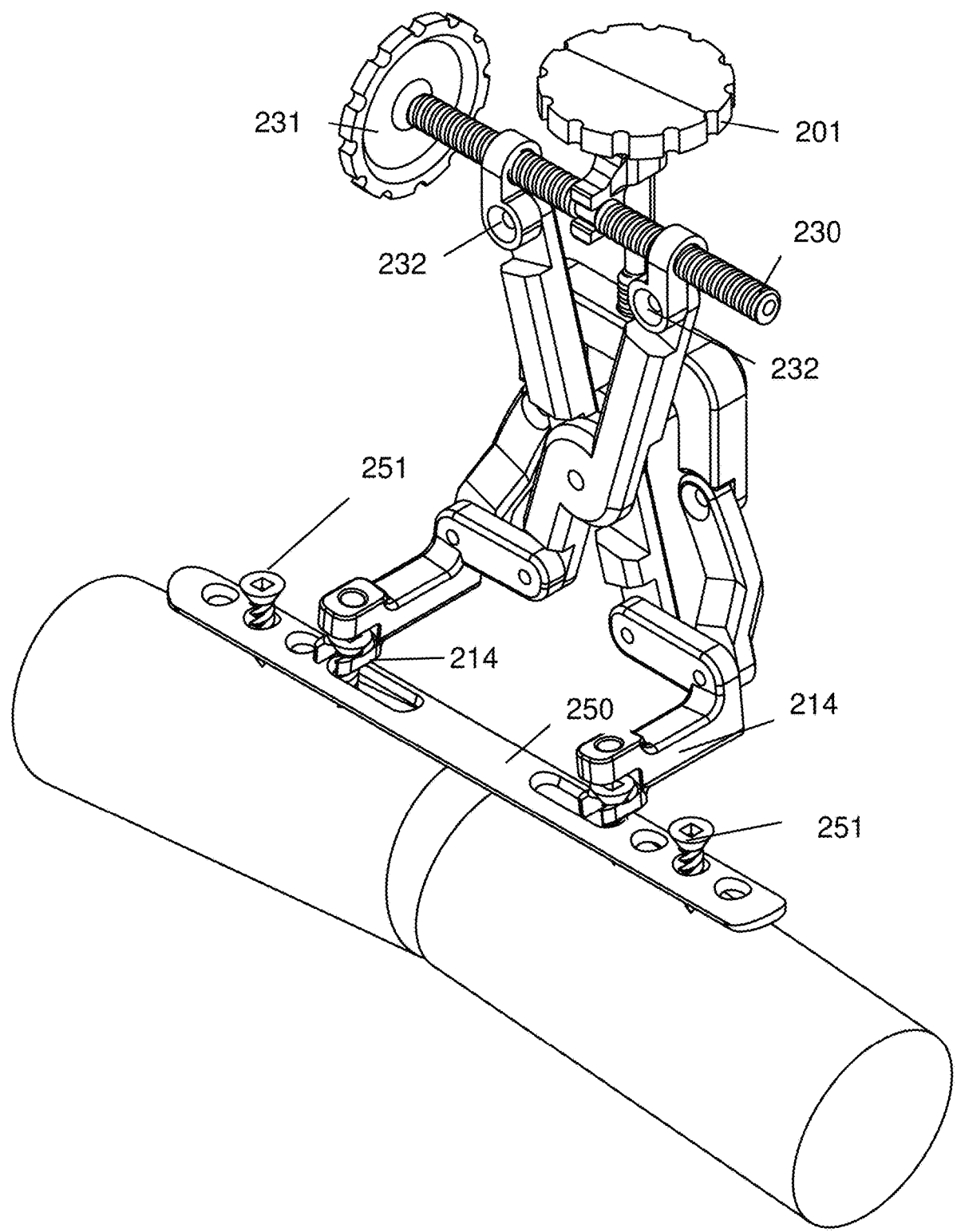
FIG. 11 shows a perspective view of the small orthopedic compressor with the scissor hinge and two screw adjustments, in use to align bones for placement of a bone plate.
Figure 12:
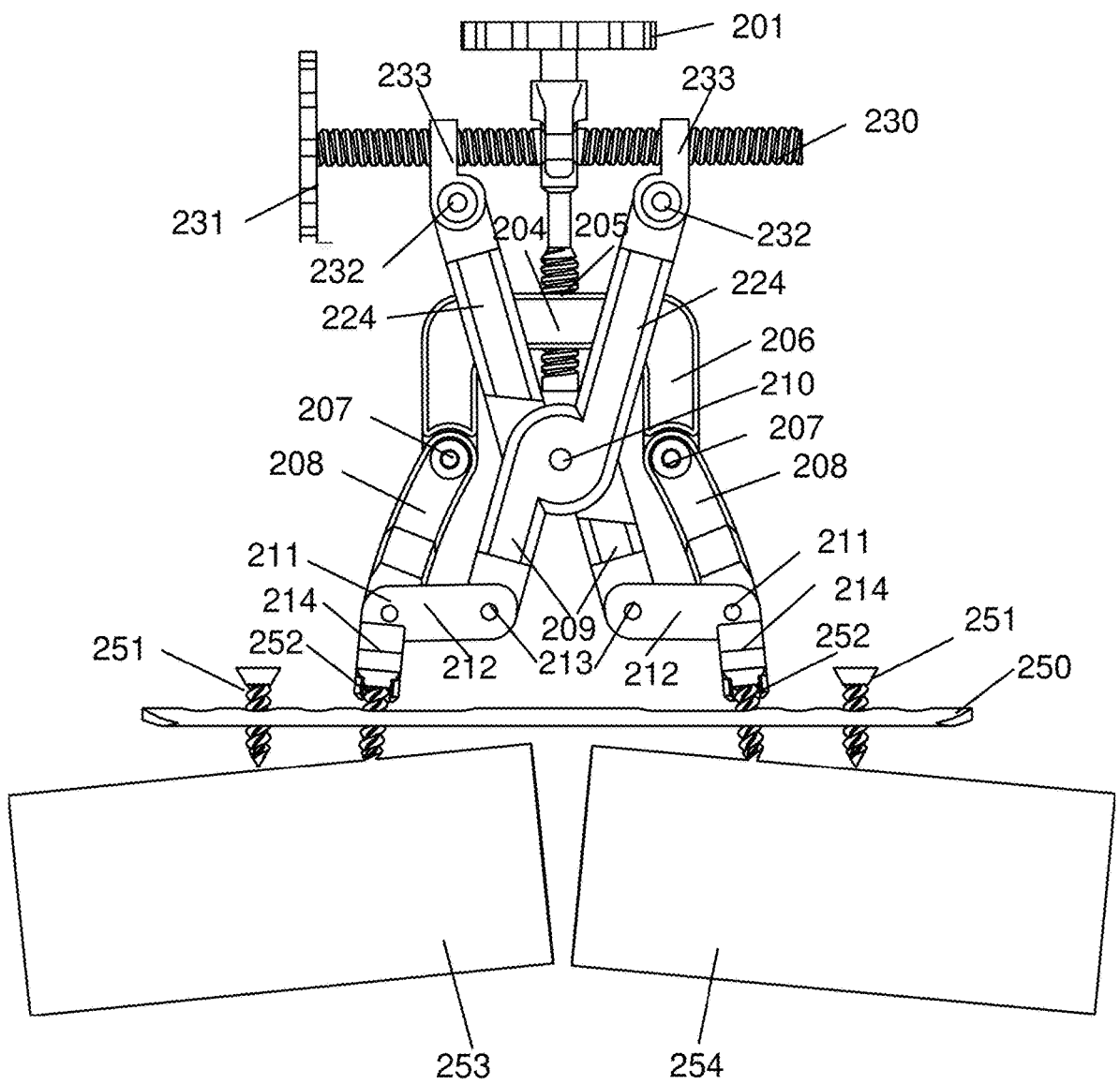
FIGS. 12 and 13 shows a front view of the small orthopedic compressor with the scissor hinge and two screw adjustments as shown in FIG. 11, before and after alignment of bones using a bone plate.
Figure 13:
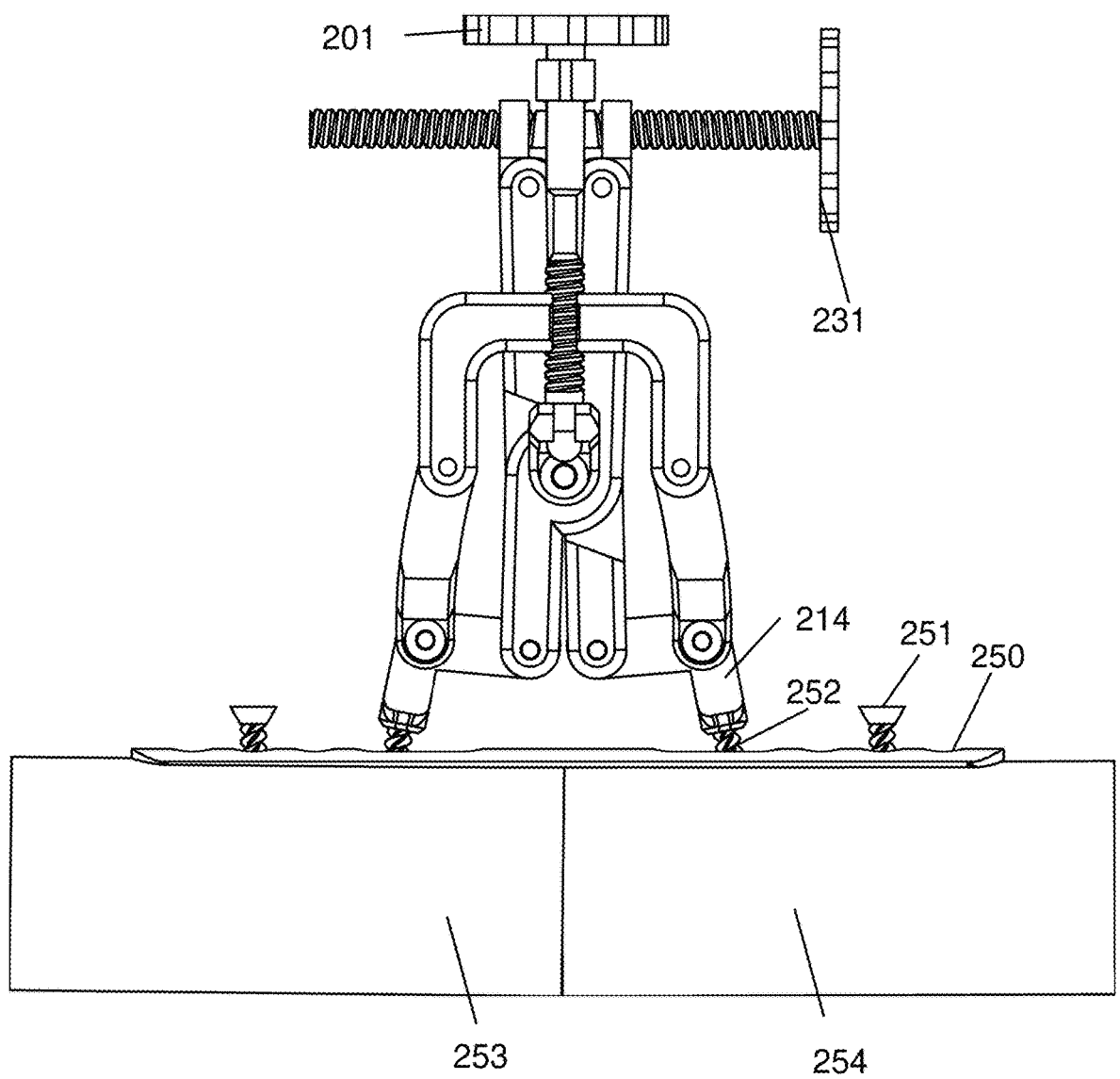
Figure 14:
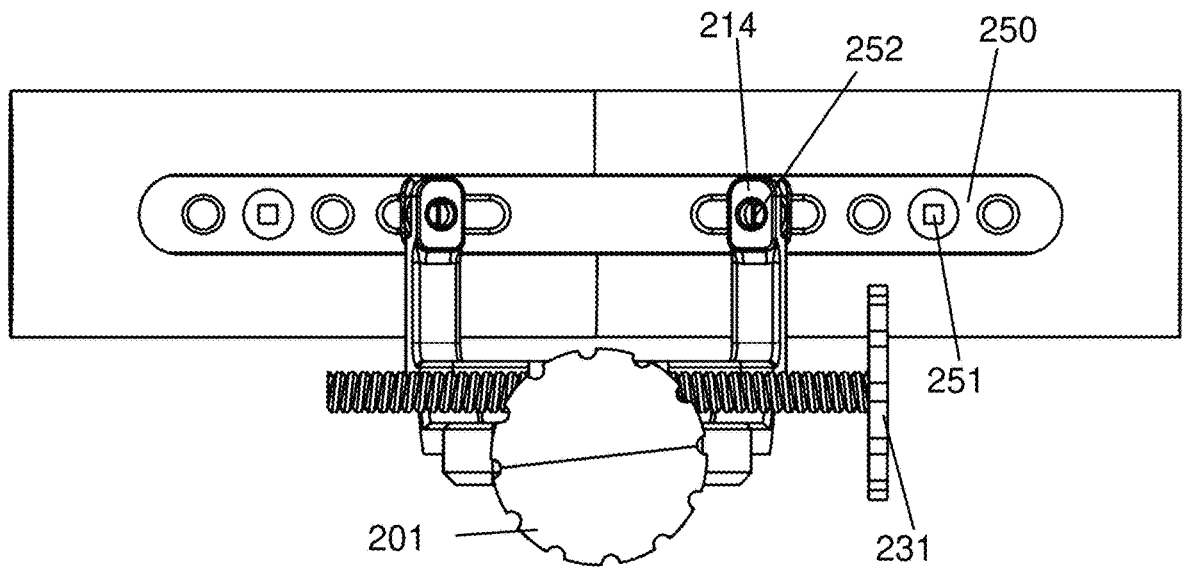
FIG. 14 shows a top view of the small orthopedic compressor with the scissor hinge and two screw adjustments, after alignment of bone and placement of the bone plate.
Figure 15:
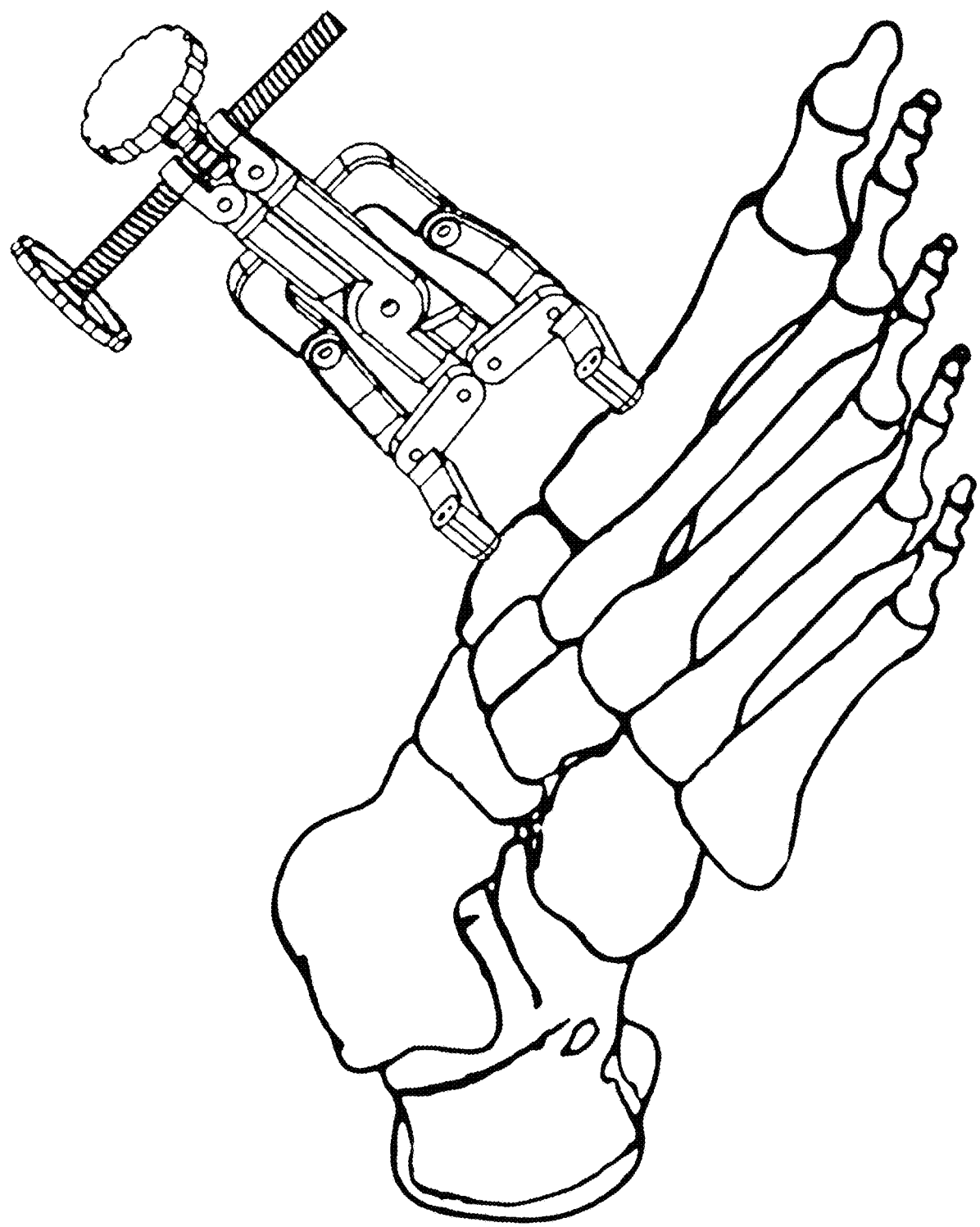
FIG. 15 shows a perspective view of the small orthopedic compressor with the scissor hinge and two screw adjustments, in use to proximate a metatarsal and cuneiform.

FIGS. 11, 12, 13, and 14 show the small orthopedic compressor according to the embodiments of FIGS. 8 to 10, in use to align bones for placement of a bone plate. The bone plate 250 has slots to accommodate the feet 214 over a range of lateral displacement. The feet 214 have recesses to accept and release from screws 252. The bone plate is screwed to the bone portions 253, 254 with the screws 252, and the adjustments used to align the bone 253, 254 portions and to proximate the respective ends. After alignment, a second set of screws 251 are then inserted through the plate 250 into the bone 253, 254 to hold the plate 250 and bone 253, 254 in place, and the instrument may then be removed with the bone 253, 254 aligned and the plate 250 ad screws 251, 252 in place.

The screws 252 are held in place to the feet 214 of the instrument, such that the feet 214, screws 252, and the bone plate 250 form one unit prior to contact with the bones. Typically, the screws 252 are loosely screwed through the plate 250 into the bone through slots in the plate 250. This allows adjustment of the lateral position of the feet 214 and of the relative angle of the feet 214 by rotation of the knobs 231 and 201, respectively. When the bone is correctly aligned and proximated, the screws 251, 252 are tightened into the bone 253, 254, and the instrument may be removed from the field. Therefore, the plate 250 can provide two-point fixation on each side of the fracture or spacing.

The screws 252 have heads which engage with the recess of the feet 214, but which after alignment of the bones and affixation of the screws 251, the feet 214 are disengaged from the screws 252, and the screws 252 then tightened to hold the bone plate securely. The head of screw 252 may be, e.g., hexagonal or square, permitting adjustment and/or removal of the screw 252 after the instrument is detached.

Figure 16:
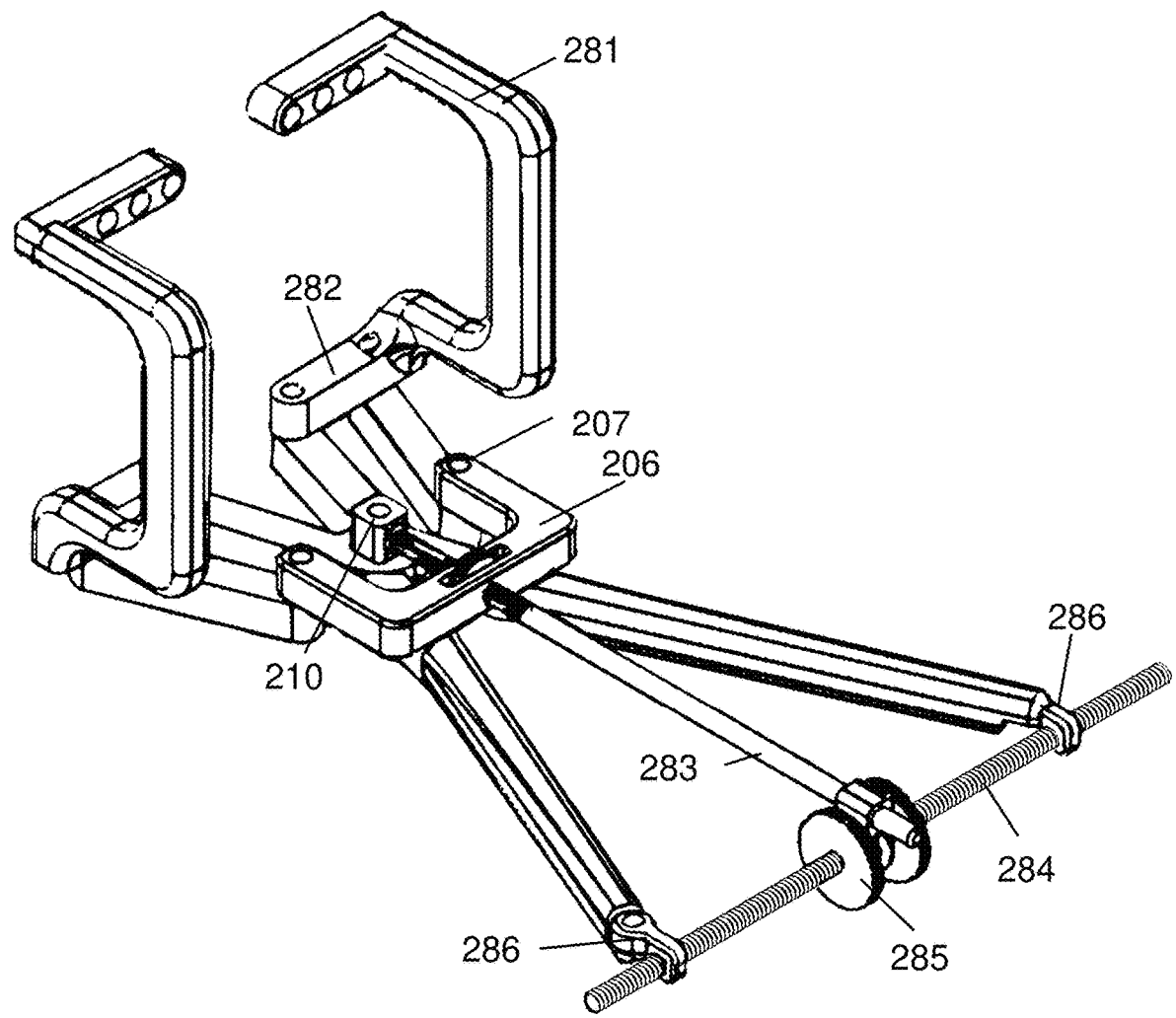
FIG. 16 shows an orthopedic compressor-distractor with offset feet, and having a handle for the angular adjustment shaft removed.

FIG. 16 shows a perspective view of the small orthopedic compressor with the scissor hinge and two screw adjustments, in use to proximate a metatarsal and cuneiform.

Figure 17:
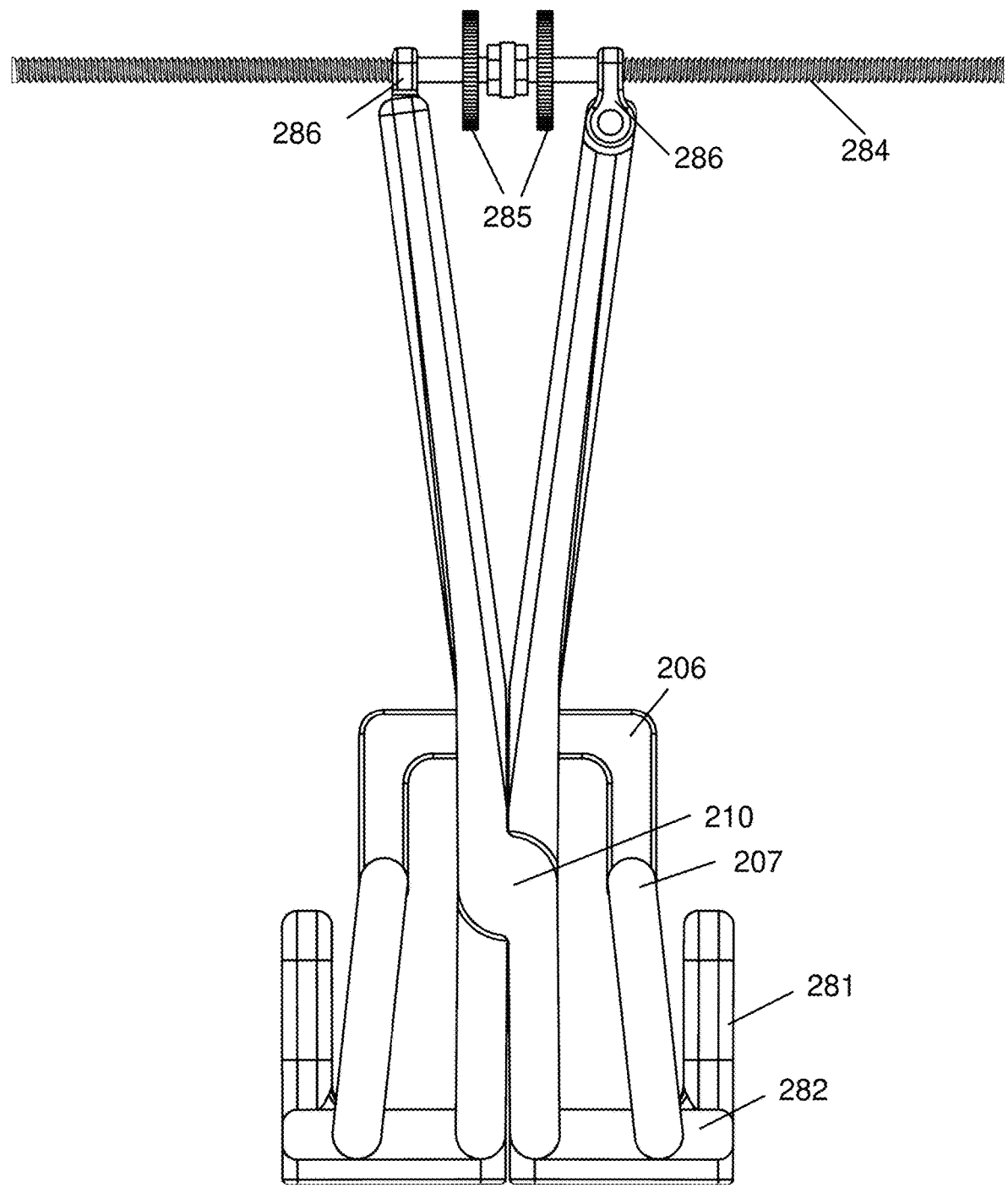
FIGS. 17-18 shows an orthopedic compressor-distractor with offset feet according to FIG. 16, and having the angular adjustment shaft and handle removed.
Figure 18:
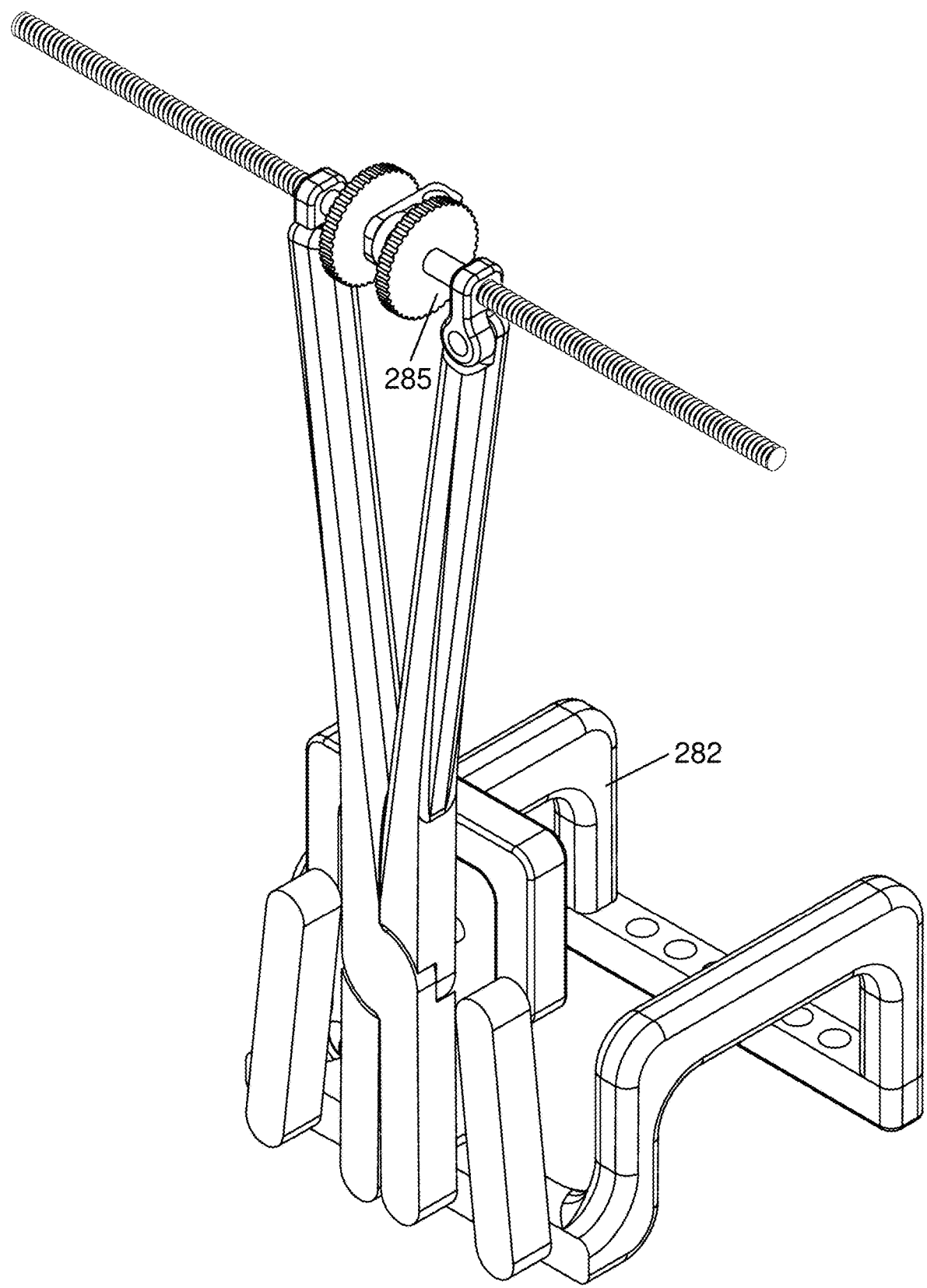

FIGS. 16-18 shows a perspective view of an orthopedic compressor-distractor having offset feet 281, removing the mechanism from the surgical field for increased visibility and reduced interference with other instruments. A knob corresponding to knob 201 is removed for visibility from FIG. 16, and the knob and angular adjustment shaft are removed in FIGS. 17 and 18. The feet 281 in this embodiment are displaced from the plane formed by the handles and scissor hinge, and are maintained in a defined relative angle by a rotation of shaft 283, which acts to rotate the quadrilateral linkage 282, which is continuous with the feet 281. In this embodiment, the separation of the feet 281 is controlled by a clockwise and counterclockwise threated rod 284, in followers 286, controlled by a rotation of thumbwheel 285.

Figure 19:
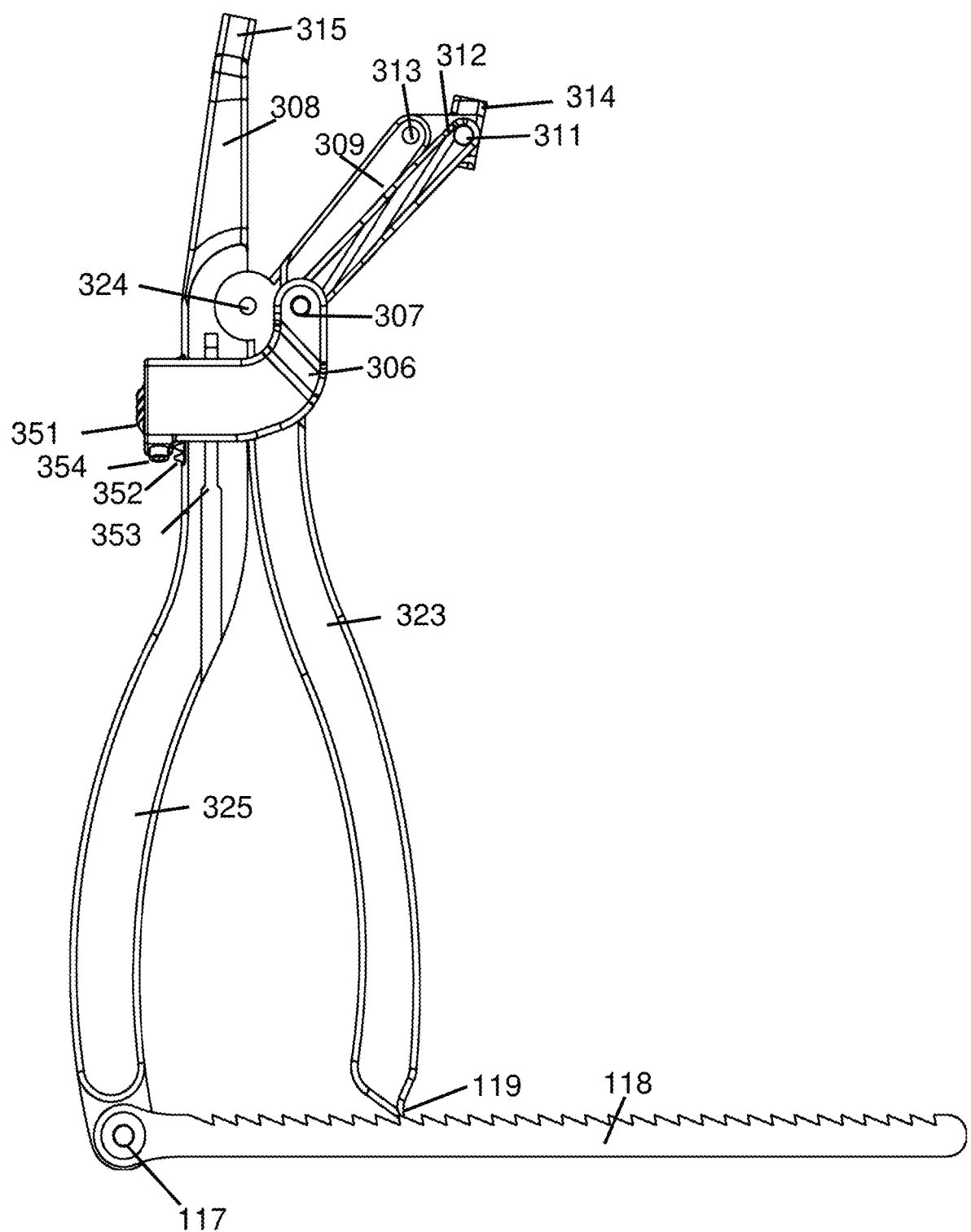
FIG. 19 shows a front view of an orthopedic distractor with an asymmetric adjustment mechanism and ratchet.
Figure 20:
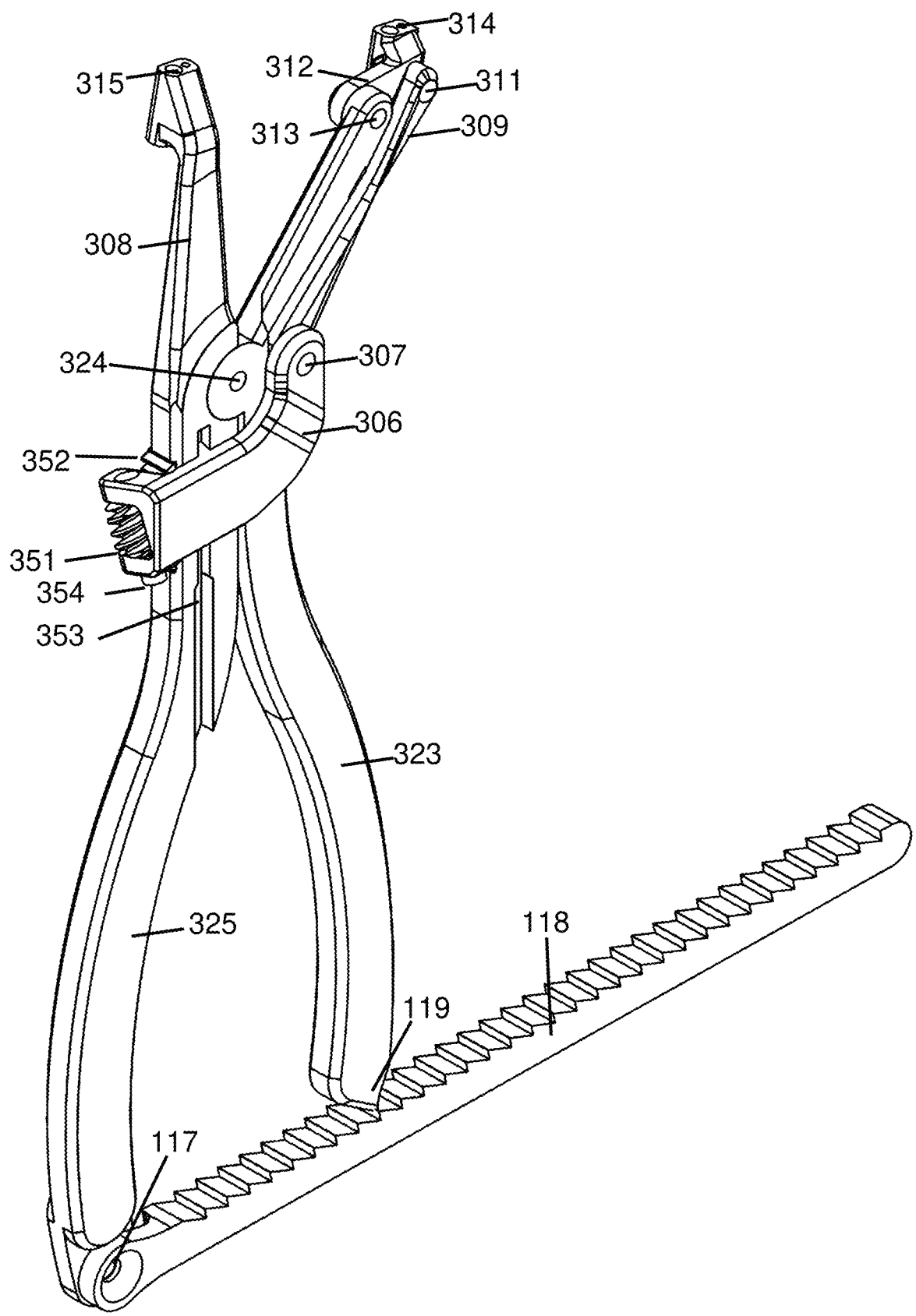
FIG. 20 shows a perspective view of the orthopedic compressor with an asymmetric adjustment mechanism and ratchet according to FIG. 19.

FIGS. 19-20 show an orthopedic distractor with uncrossed handles linked by a pivoting hinge 324 and helical threaded adjustment acting on a rack. A pair of handles 323, 325, linked with the hinge 324, control a distraction of a pair of feet 314, 315. The handles 323, 325 are retained in a desired degree of displacement by a ratchet mechanism having a ratchet bar 118, which is hinged to handle 325 with a pivot 117, and which is maintained by a spur 119.

The angle of the feet 314, 315 is adjusted by a helical screw 351, which is knurled, acting on a rack 352, and guided by a slot 353, to control an axial depth of a link 306, which is part of a quadrilateral linkage which includes outer side 308, inner side 309, and distal side 312. The helical screw 351 has a hexagonal recess 354 which accepts a hex key (Allen key) to provide an alternate to finger rotation of the helical screw. For example, a motor drive may be provided with a foot-operated switch to permit the surgeon or operator to adjust the distance between the feet 344, 345 in a hands-free manner.

Figure 21:
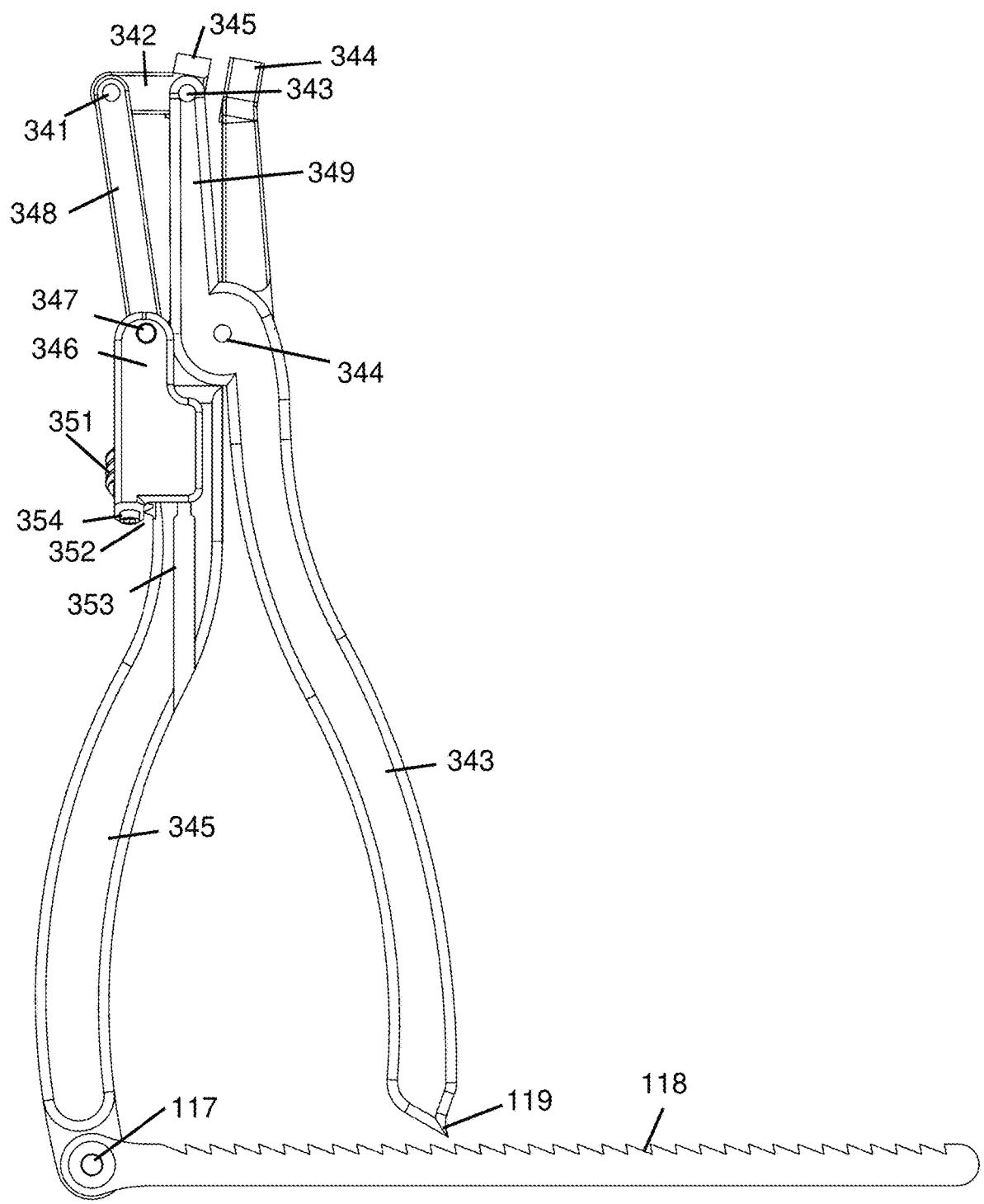
FIG. 21 shows a front view of an orthopedic compressor with an asymmetric adjustment mechanism and rachet.
Figure 22:
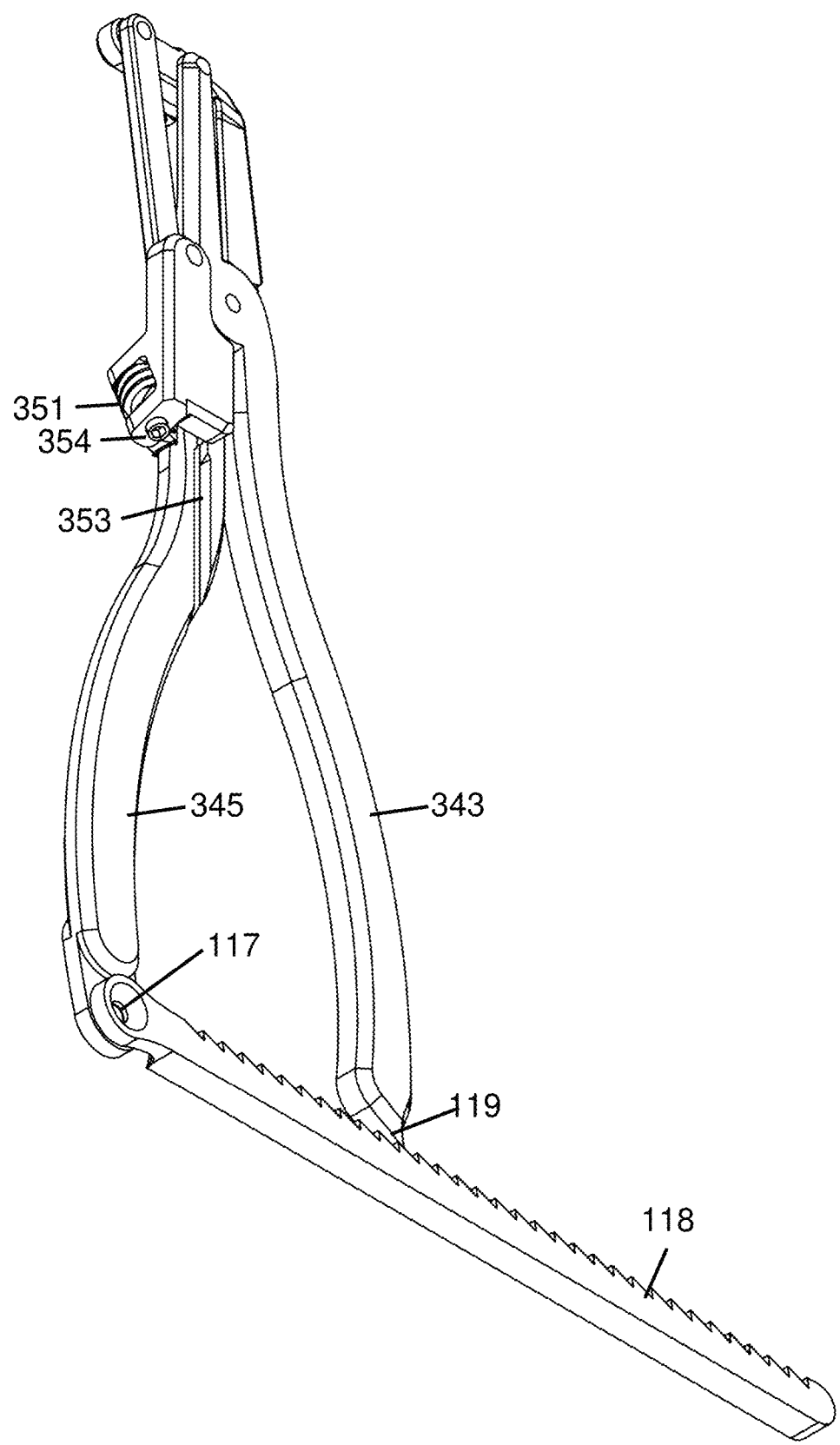
FIG. 22 shows a perspective view of the orthopedic compressor with an asymmetric adjustment mechanism and ratchet according to FIG. 21.

FIGS. 21-22 show an orthopedic compressor, similar to that of FIGS. 19-20, but with crossed handles instead of uncrossed handles, which upon application of force result in a corresponding contraction of the mounting feet rather than separation. A pair of handles 343, 345, linked with a scissor hinge 344, control a compression of a pair of feet 344, 345. The handles 343, 345 are retained in a desired degree of displacement by a ratchet mechanism having a ratchet bar 118, which is hinged to handle 345 with a pivot 117, and which is maintained by a spur 119.

The angle of the feet 344, 345 is adjusted by a helical screw 351, which is knurled, acting on a rack 352, and guided by a slot 353, to control an axial depth of a link 346, which is part of a quadrilateral linkage which includes outer side 348, inner side 349, and distal side 342. The helical screw 351 has a hexagonal recess 354 which accepts a hex key (Allen key) to provide an alternate to finger rotation of the helical screw. For example, a motor drive may be provided with a foot-operated switch to permit the surgeon or operator to adjust the distance between the feet 344, 345 in a hands-free manner. The quadrilateral linkage has pivots 347 between the link 346 and the outer side 348, pivot 341 between the outer side 348 and the distal side 342, pivot 343 between the distal side 342 and the inner side 349. The hinge 344 acts as a common pivot for both halves. This mechanism provides independence of separation of the feet 344, 345 and the relative angle of the feet 344, 345.

Figure 23:
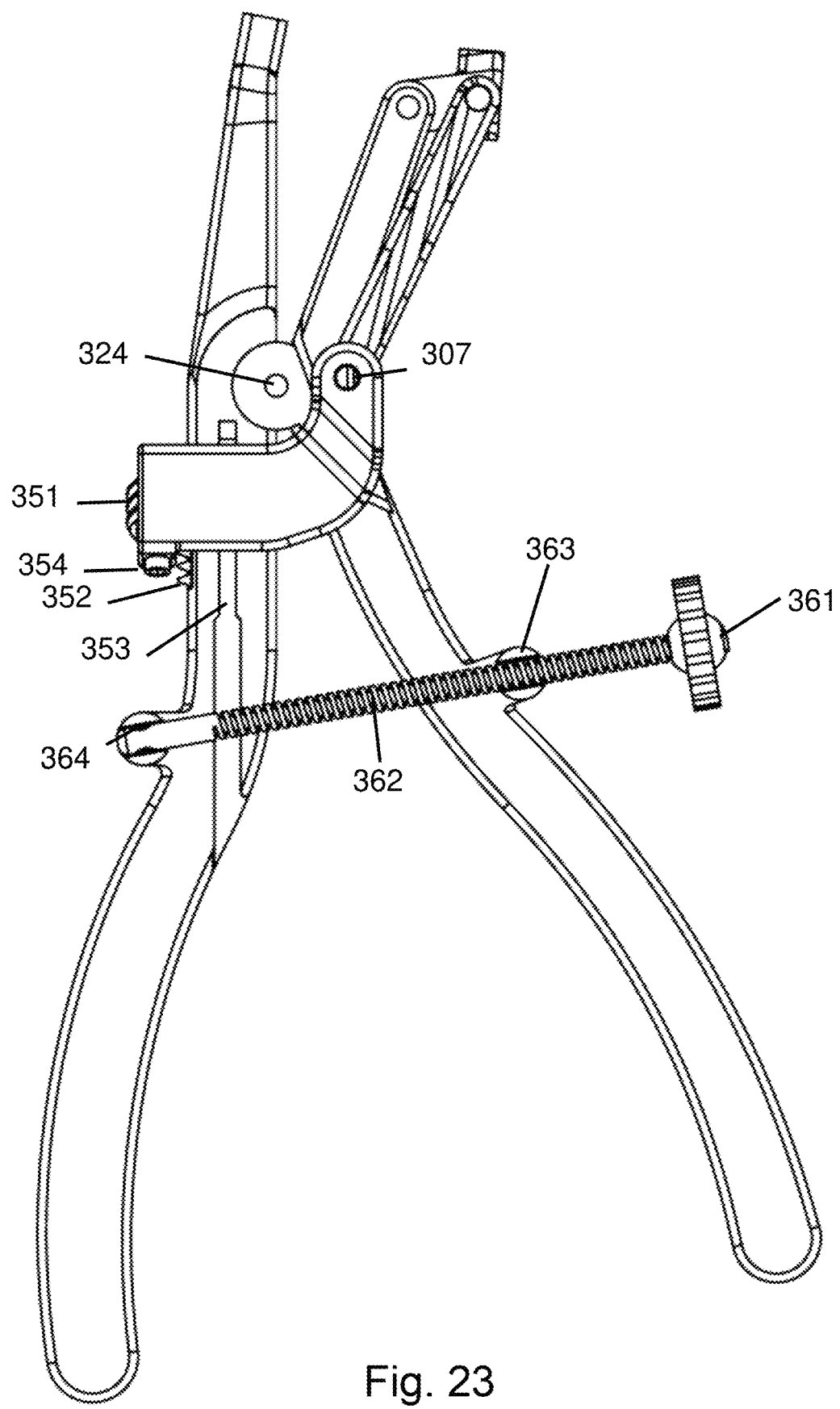
FIG. 23 shows a front view of a first embodiment of an orthopedic distractor with an asymmetric adjustment mechanism and screw adjustment of displacement.
Figure 24:
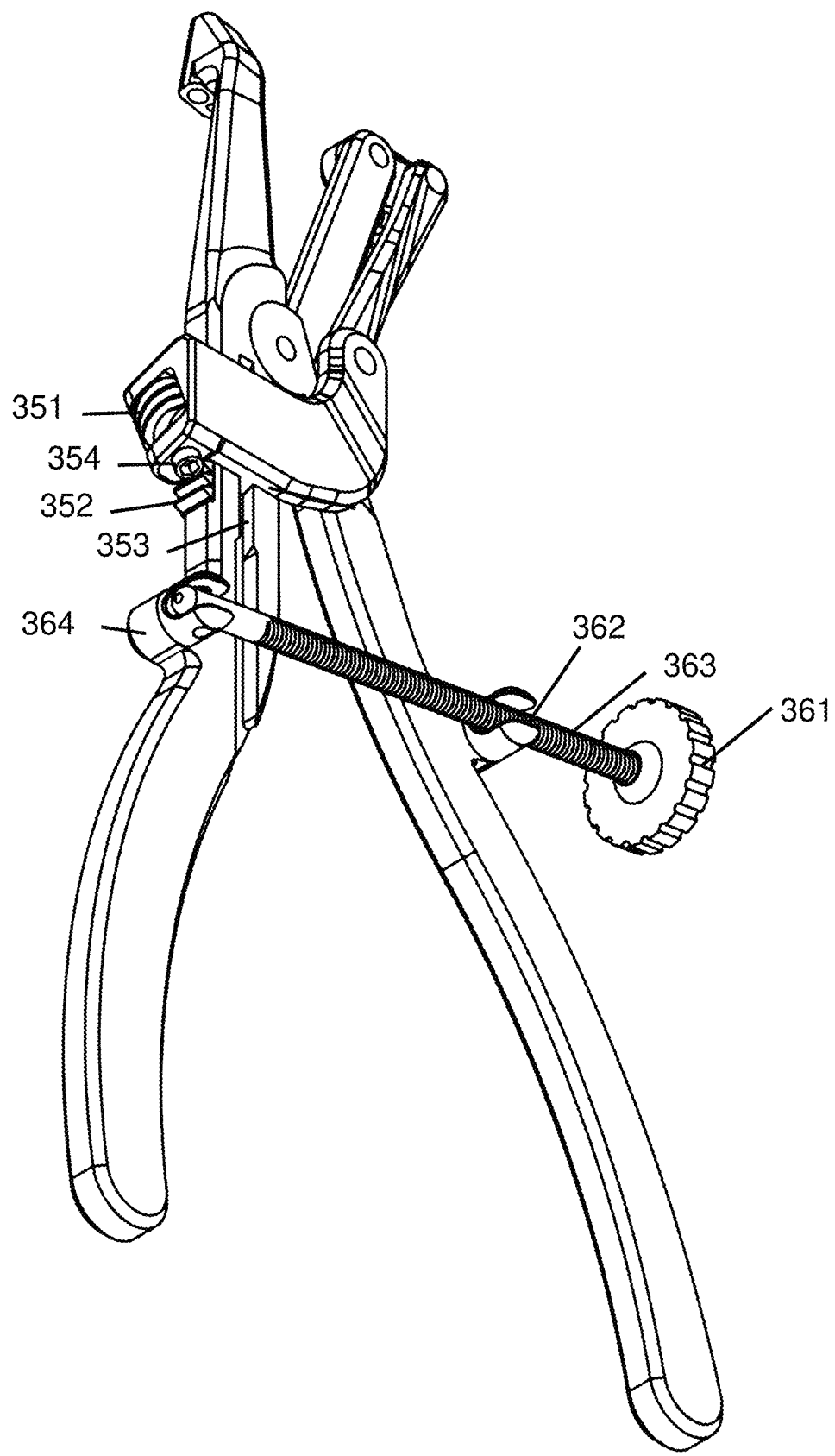
FIGS. 24 and 25 show perspective views of the first embodiment of the orthopedic distractor with an asymmetric adjustment mechanism and screw adjustment of displacement according to FIG. 23.
Figure 25:
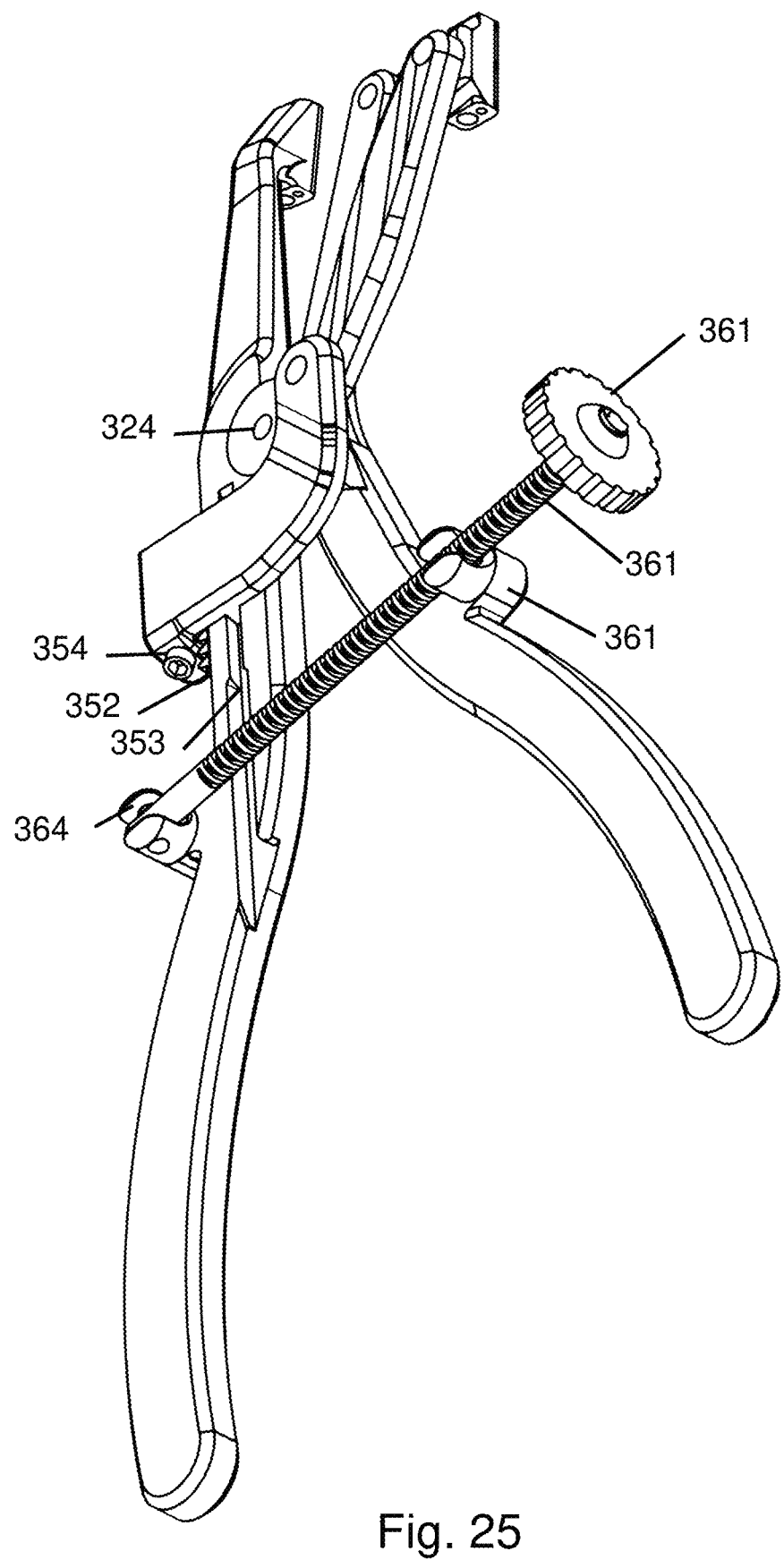

FIGS. 23-25 show a first embodiment of an orthopedic distractor with an asymmetric adjustment mechanism and screw adjustment of displacement. A screw 362 is rotated by manual rotation of a handle 361, to change a relative displacement of the scissors mechanism by applying a force between anchor 364 and follower 363. The anchor 364 is rotatable about an axis parallel to hinge 324, and also out of the plane of the uncrossed hinge mechanism. Follower 363 permits the screw 362 to be released and rotate out of the place of the scissors mechanism.

Figure 26:
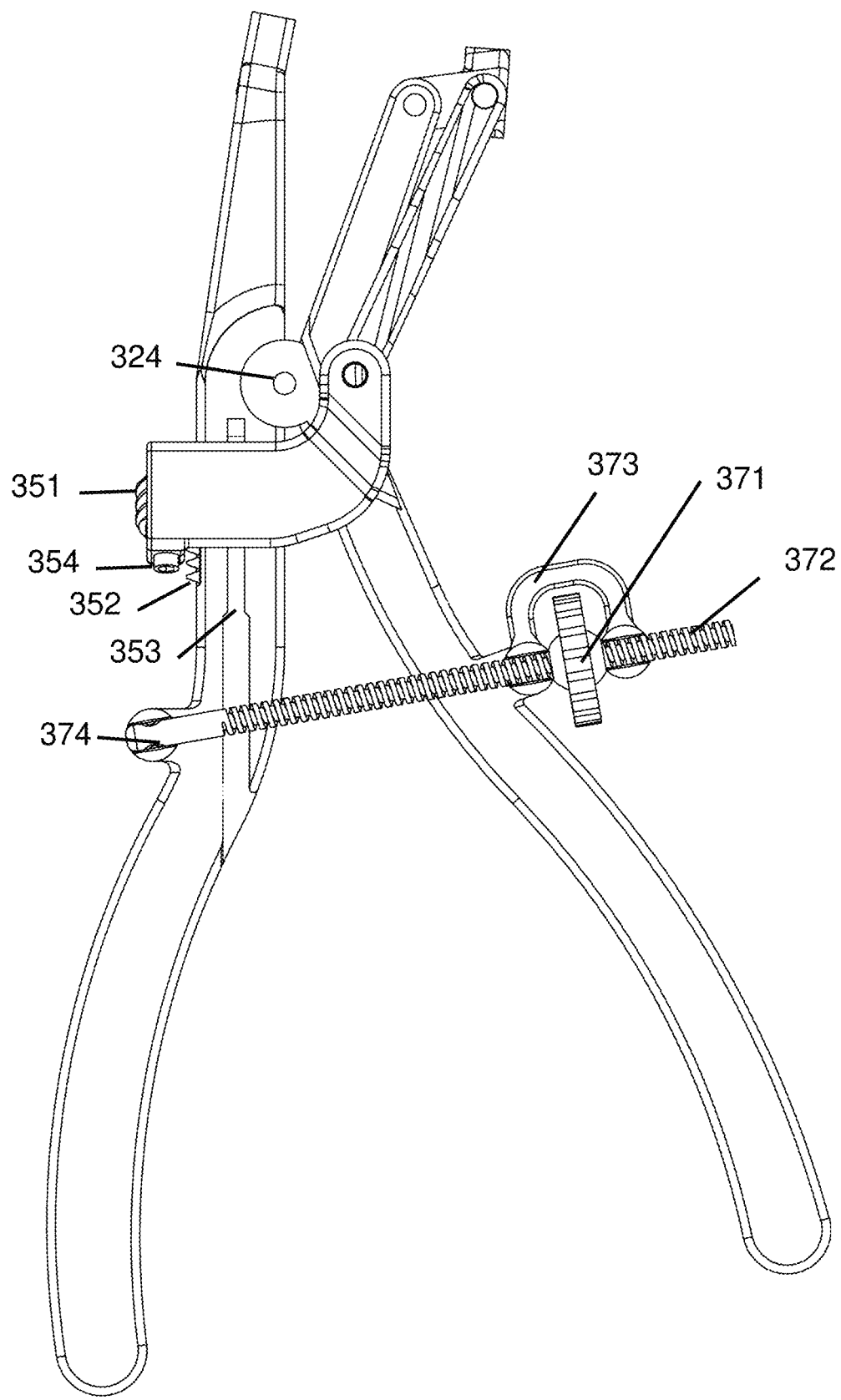
FIG. 26 shows a front view of a second embodiment of an orthopedic distractor with an asymmetric adjustment mechanism and screw adjustment of displacement.
Figure 27:
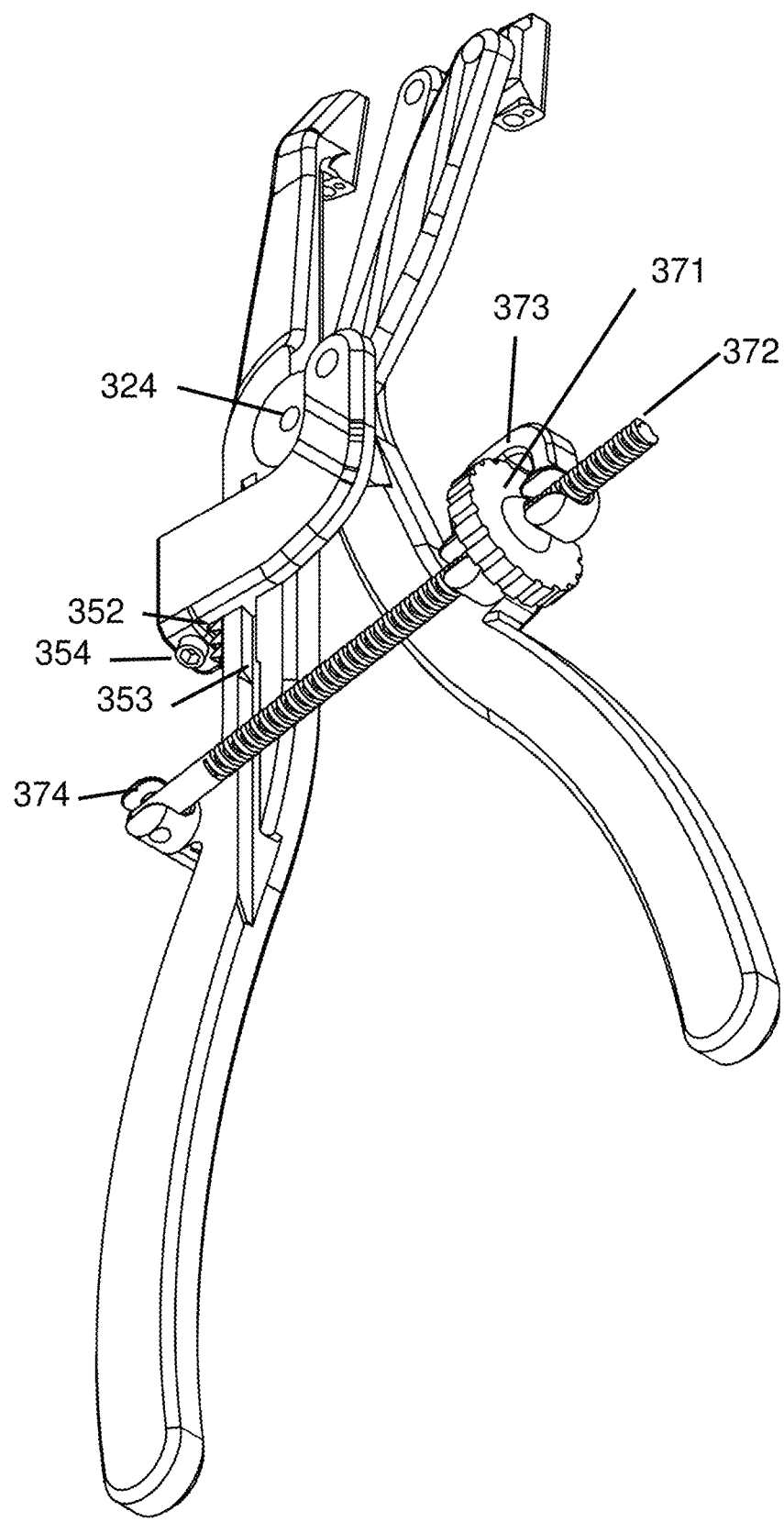
FIGS. 27 and 28 show perspective views of the second embodiment of the orthopedic distractor with an asymmetric adjustment mechanism and screw adjustment of displacement according to FIG. 26.
Figure 28:
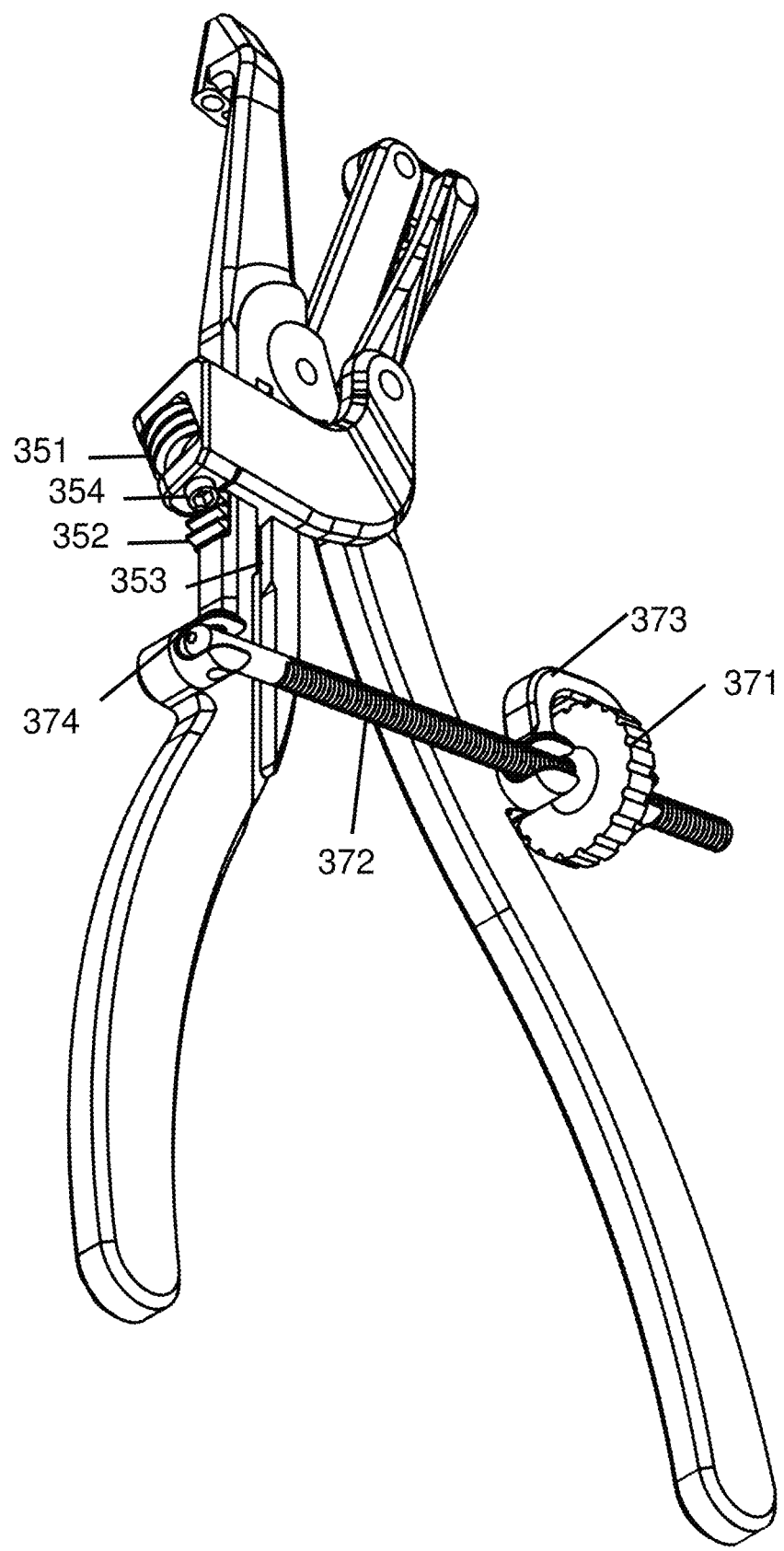

FIGS. 26-28 show a second embodiment of an orthopedic distractor with an asymmetric adjustment mechanism and screw adjustment of displacement. In this case, the adjustment mechanism is located at the end of the handles, with threaded rod 372 mounted on anchor 374, which is hinged to rotate parallel to the hinge 324. Knurled adjustment 371 acts on the threaded rod 372 to control the displacement of the anchor 374 and the follower 373. For cleaning, the knurled adjustment 371 may be removed from the follower 373 and the threaded rod 372 rotated downward.

Figure 29:
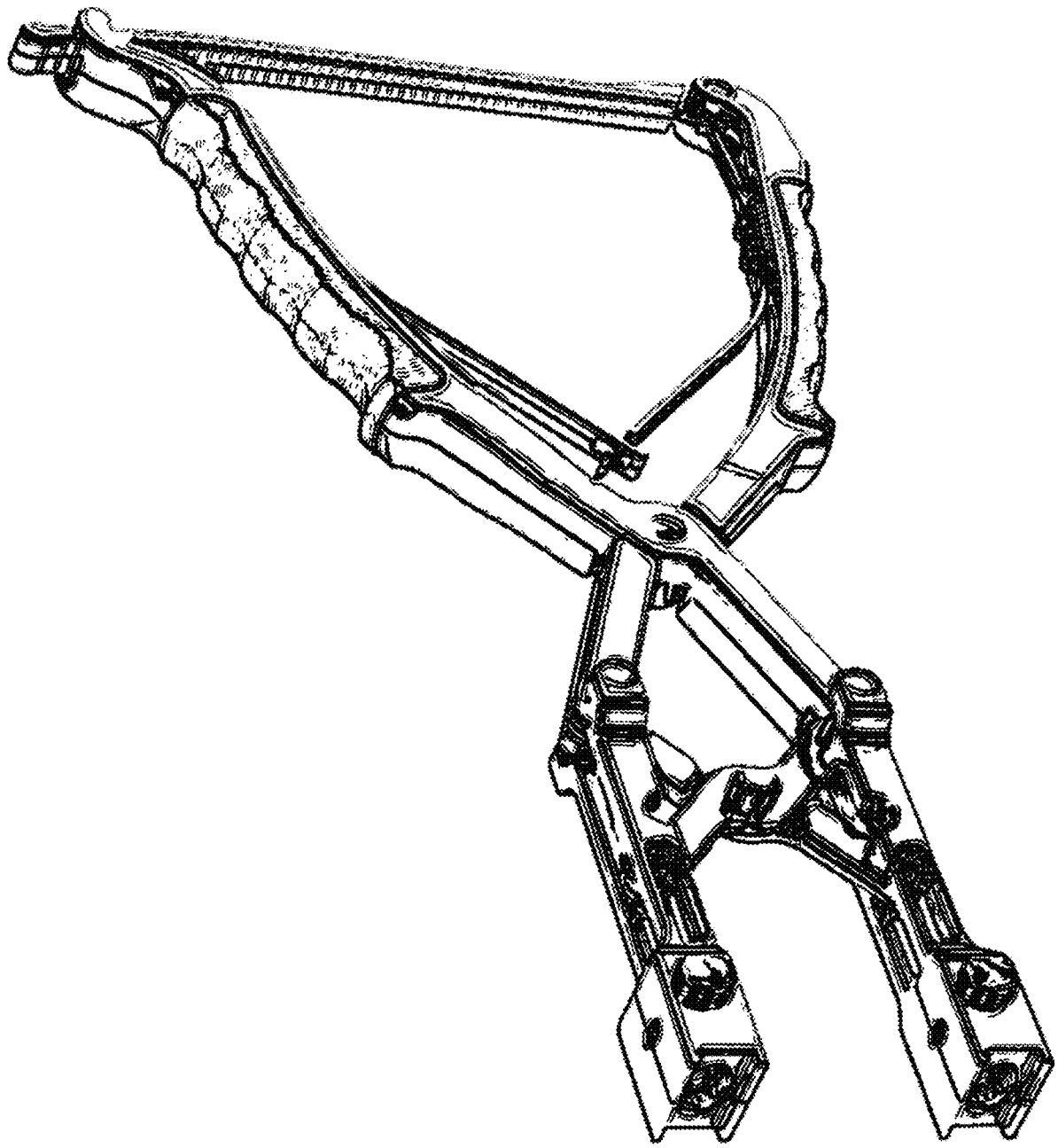
FIG. 29 shows a prior art Intech Medical parallel compressor.
Figure 30:
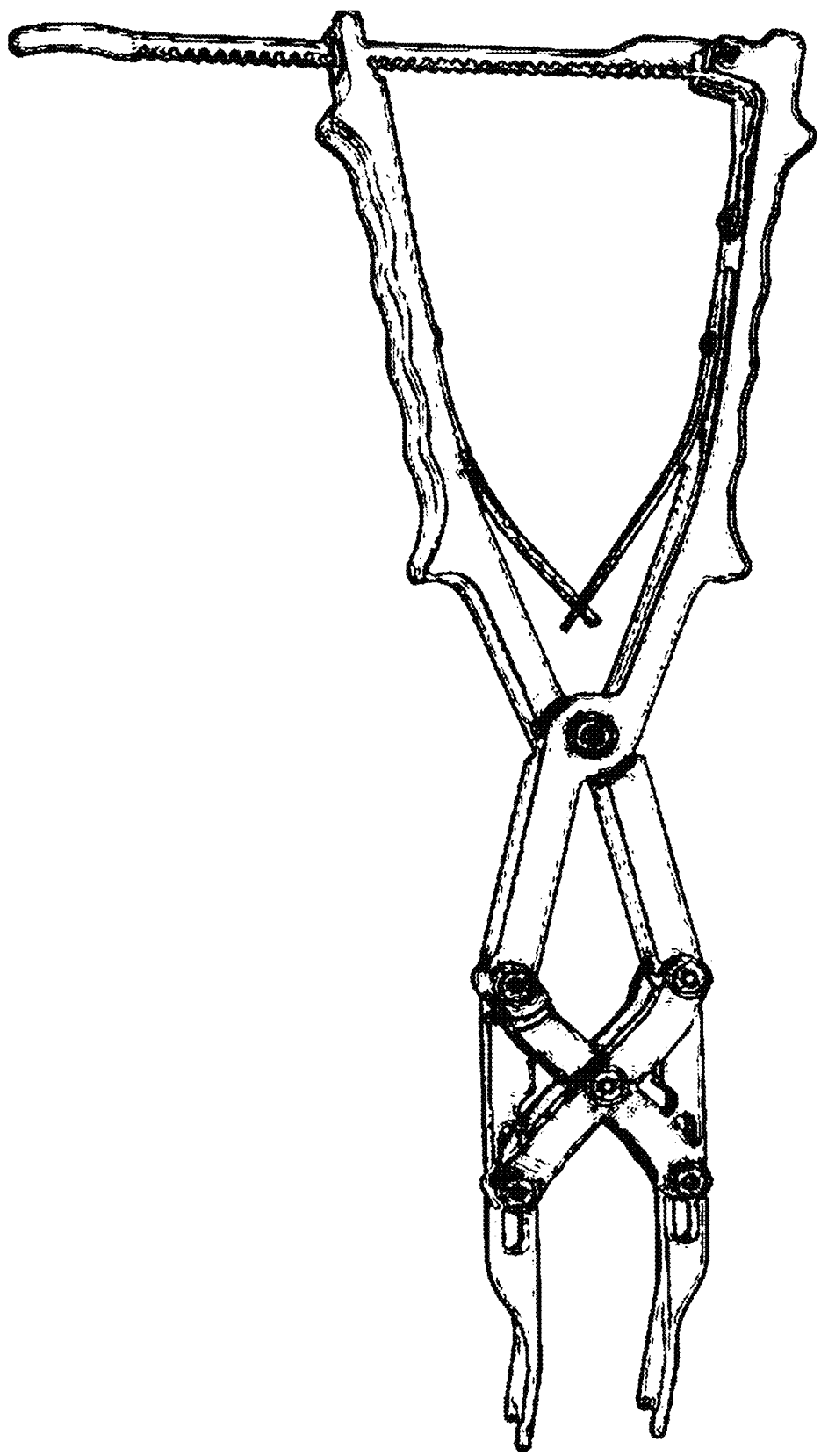
FIG. 30 shows a prior art Omnia Health self-retaining parallel compressor.
Figure 31:
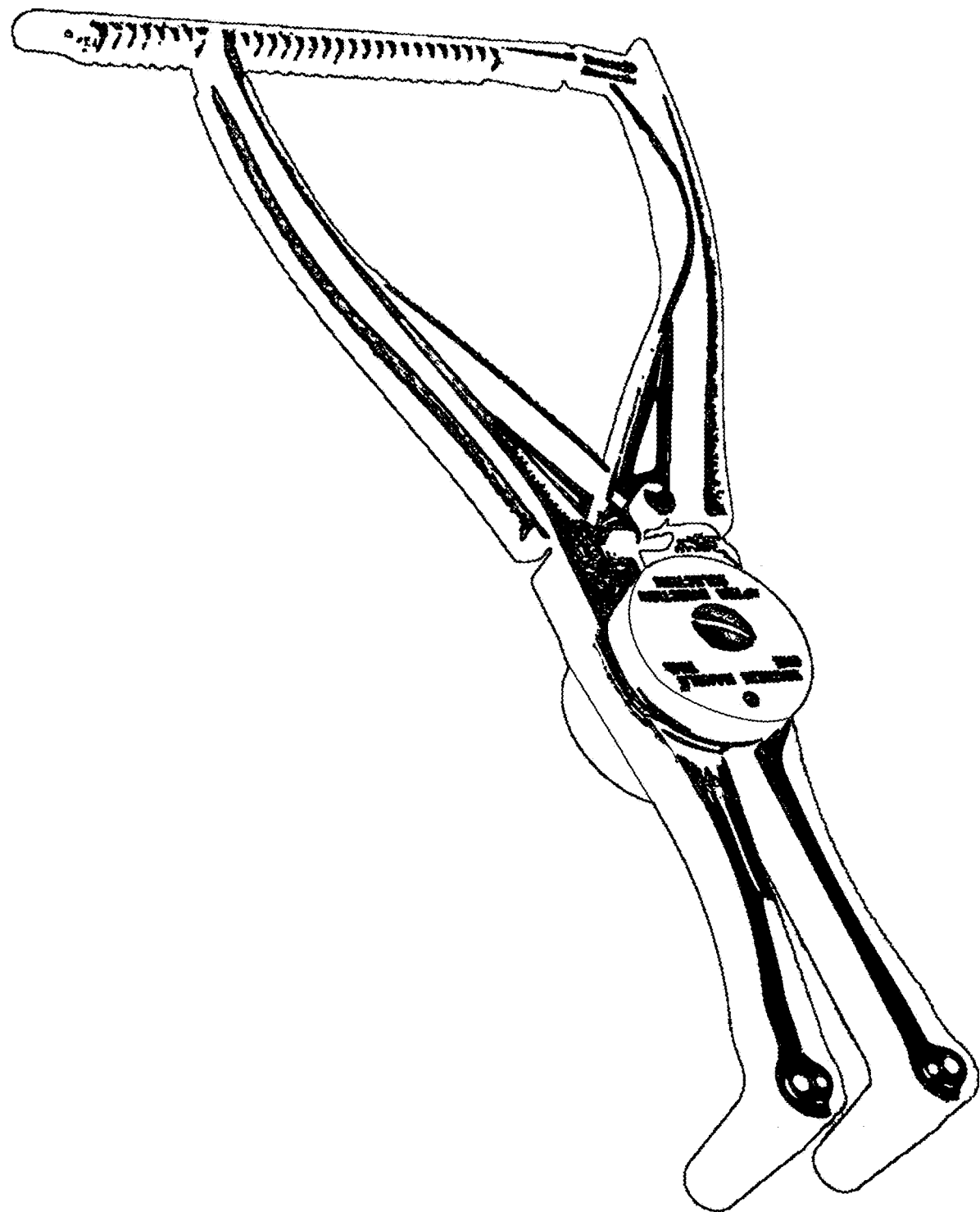
FIG. 31 shows a prior art Innomed compressor-distractor with switchable functioning.
Figure 32:
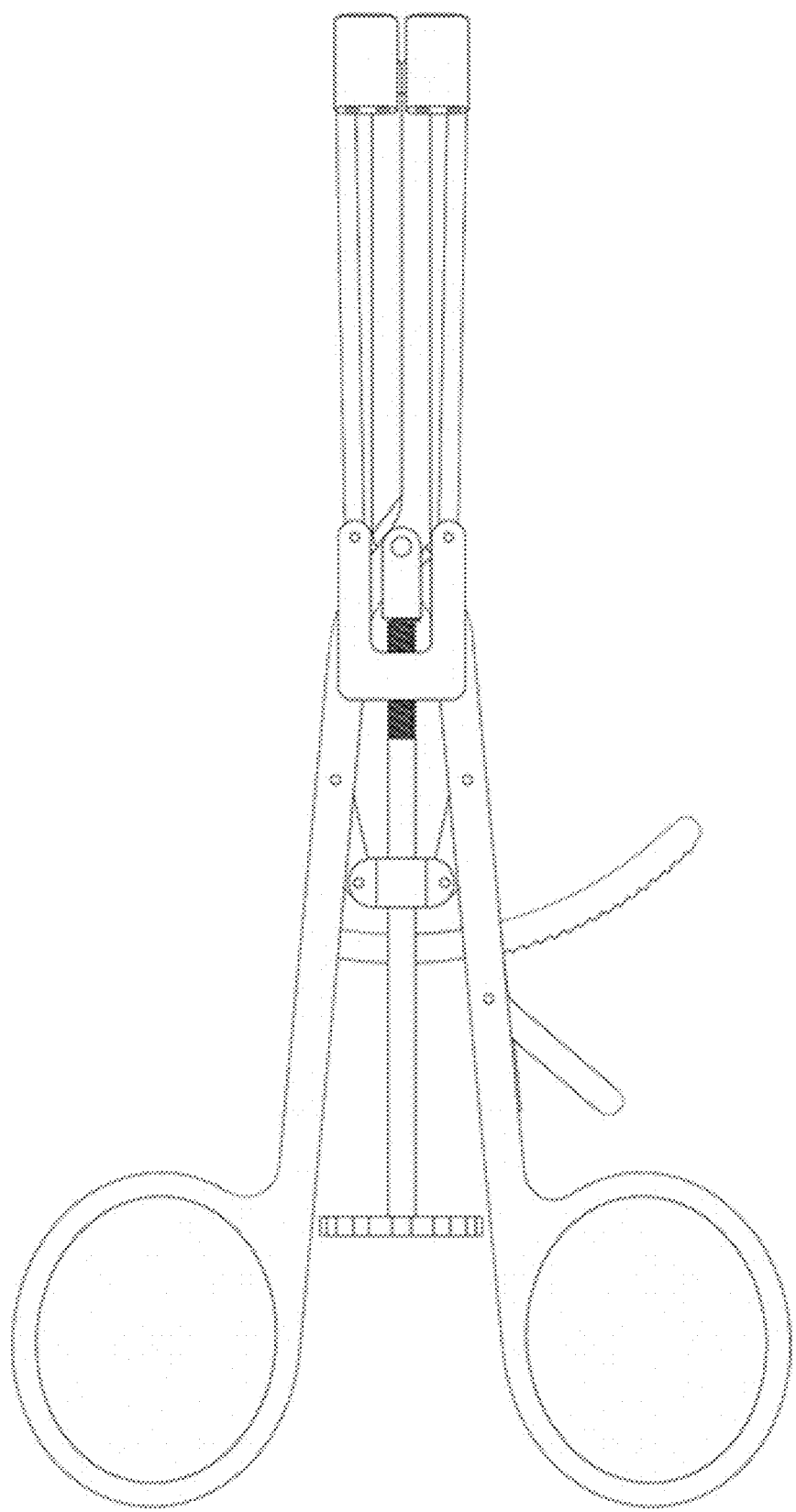
Figure 33:
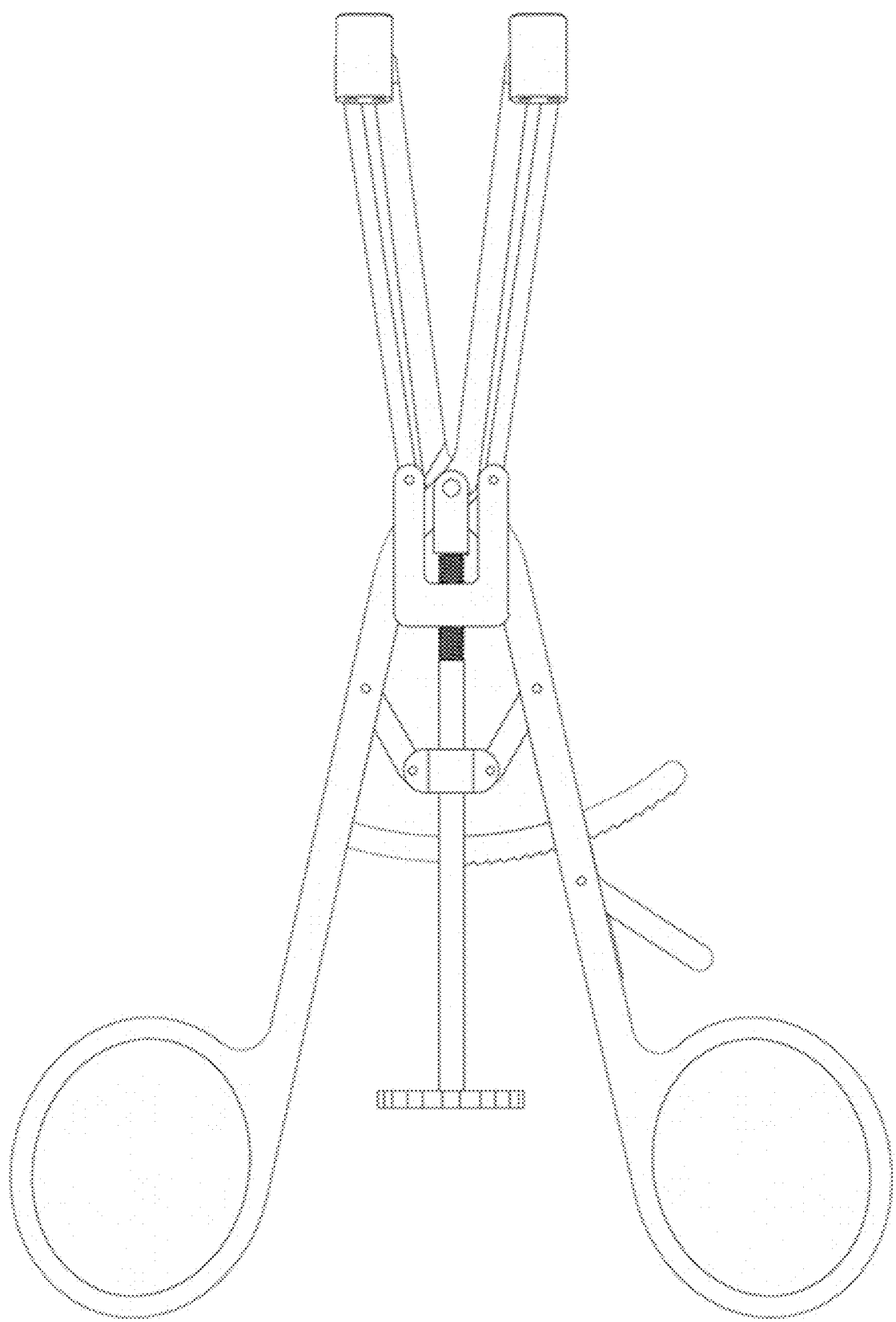
Figure 34:
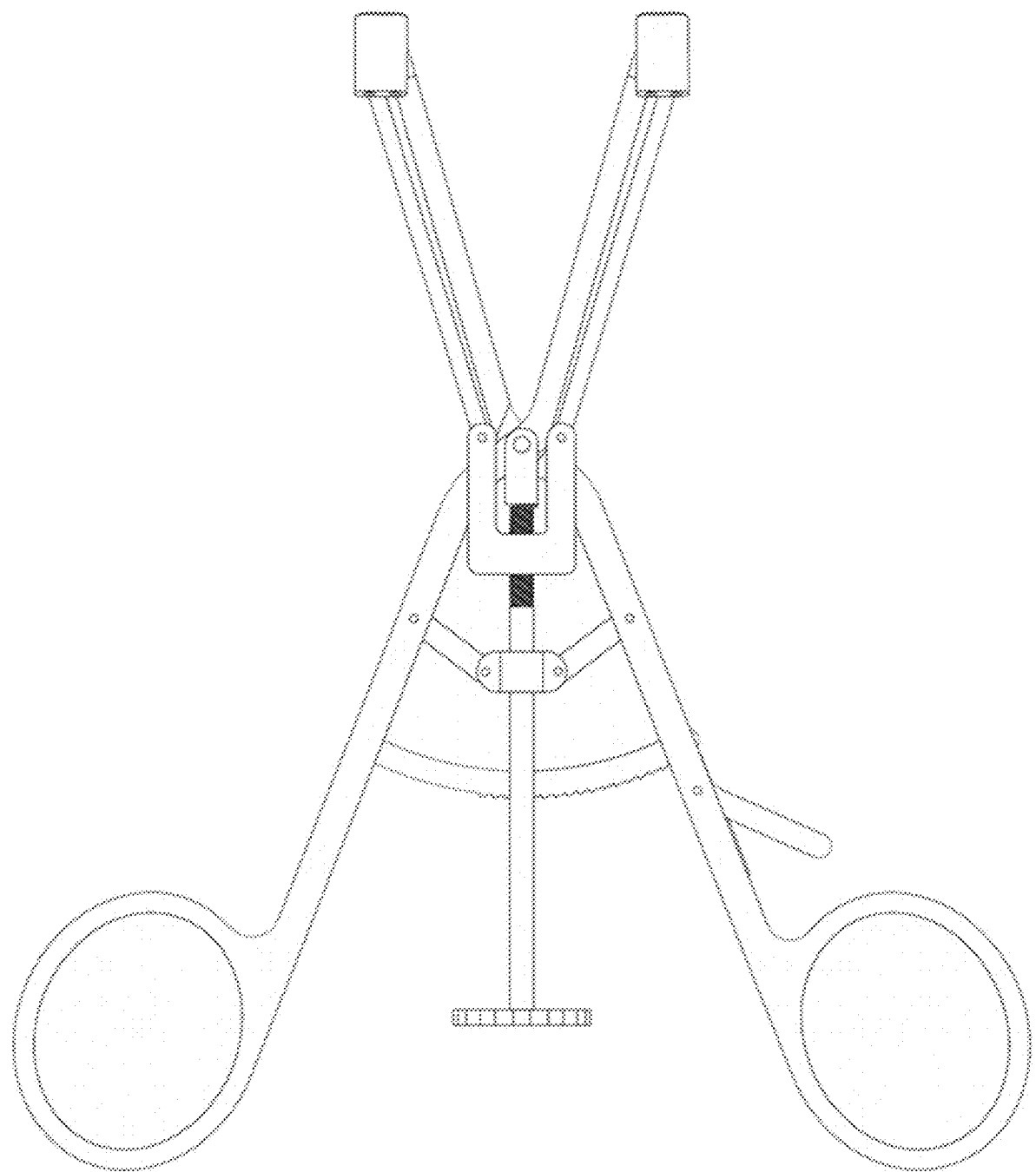
Figure 35:
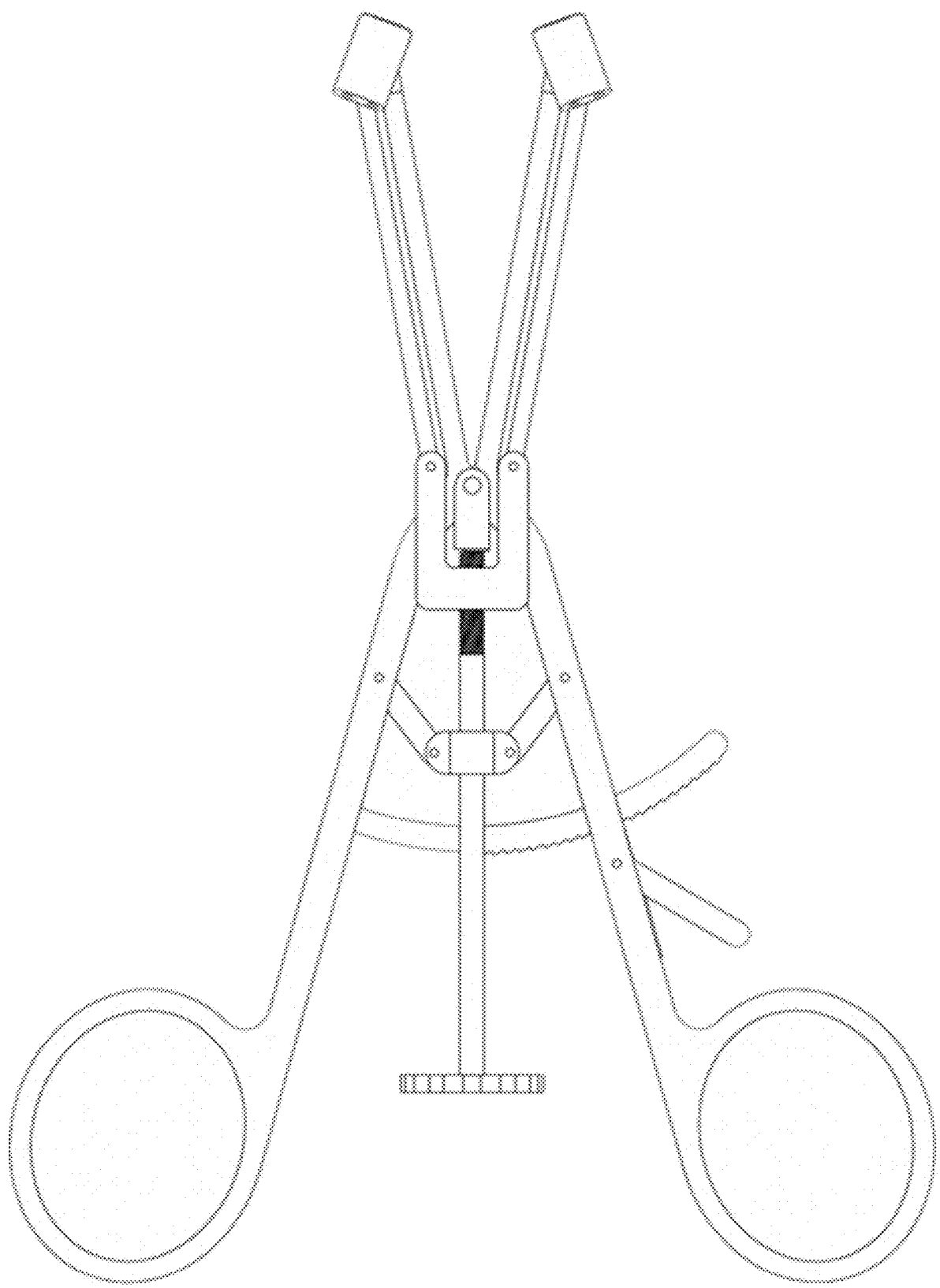
Figure 36:
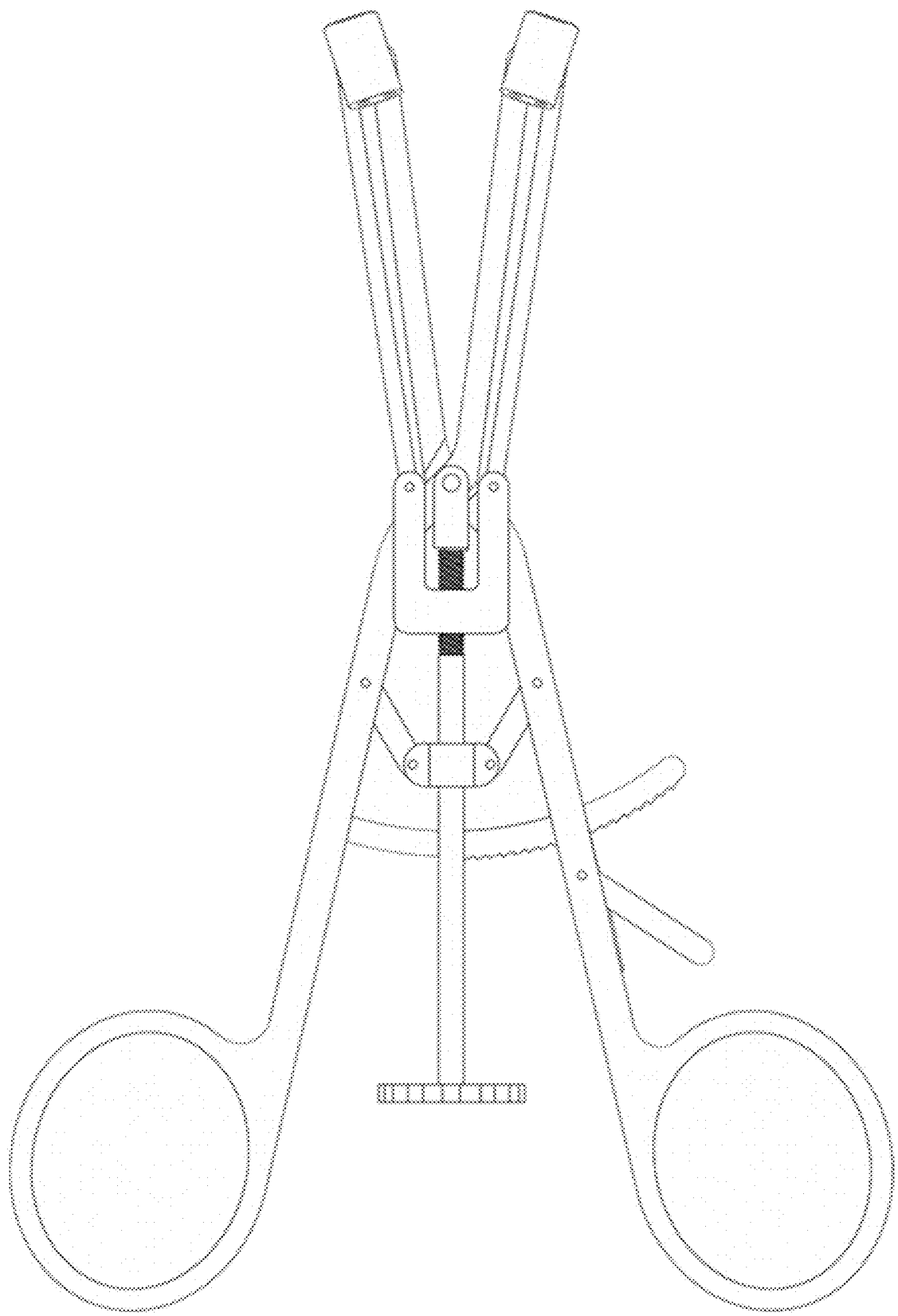
Figure 37:
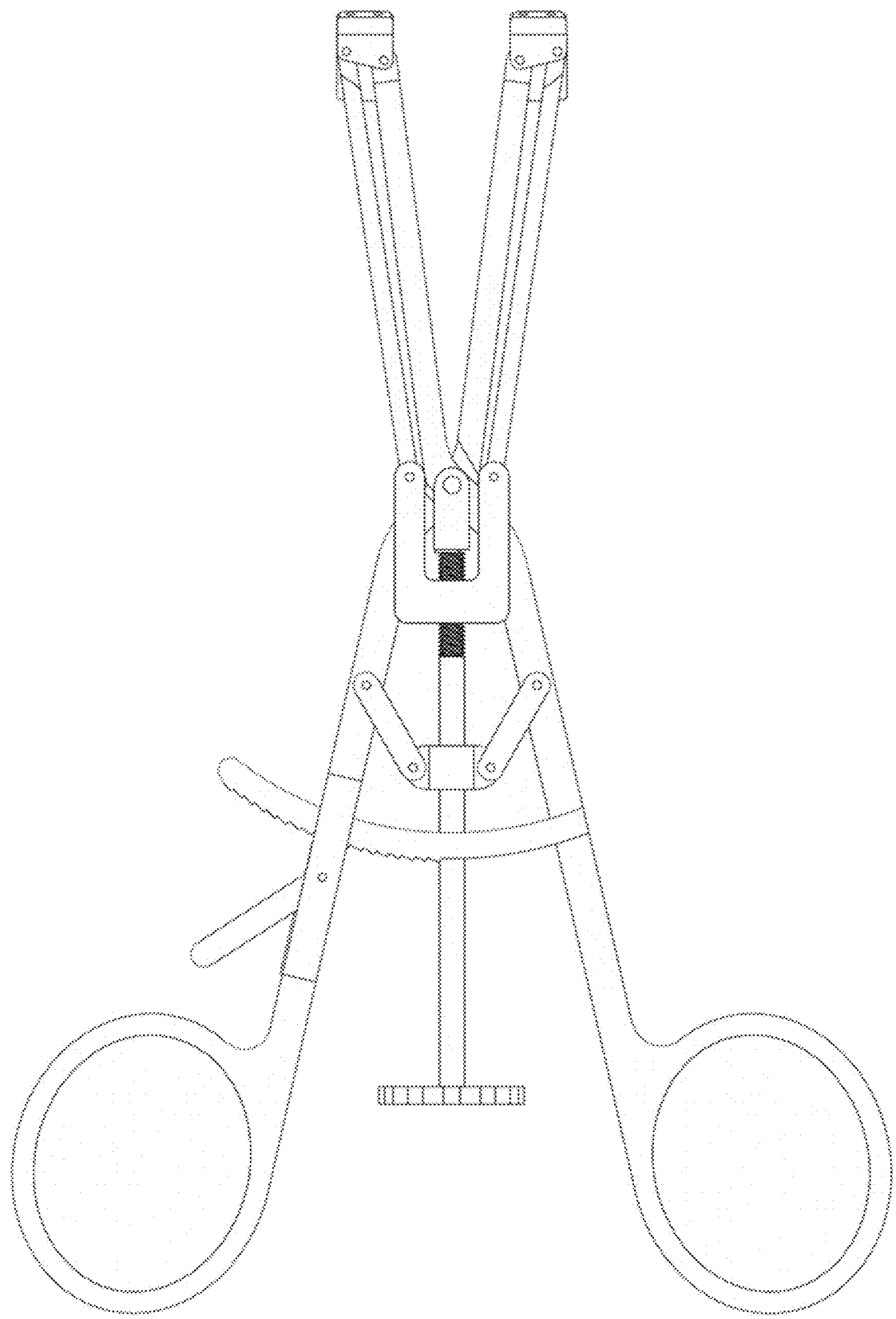
Figure 38:
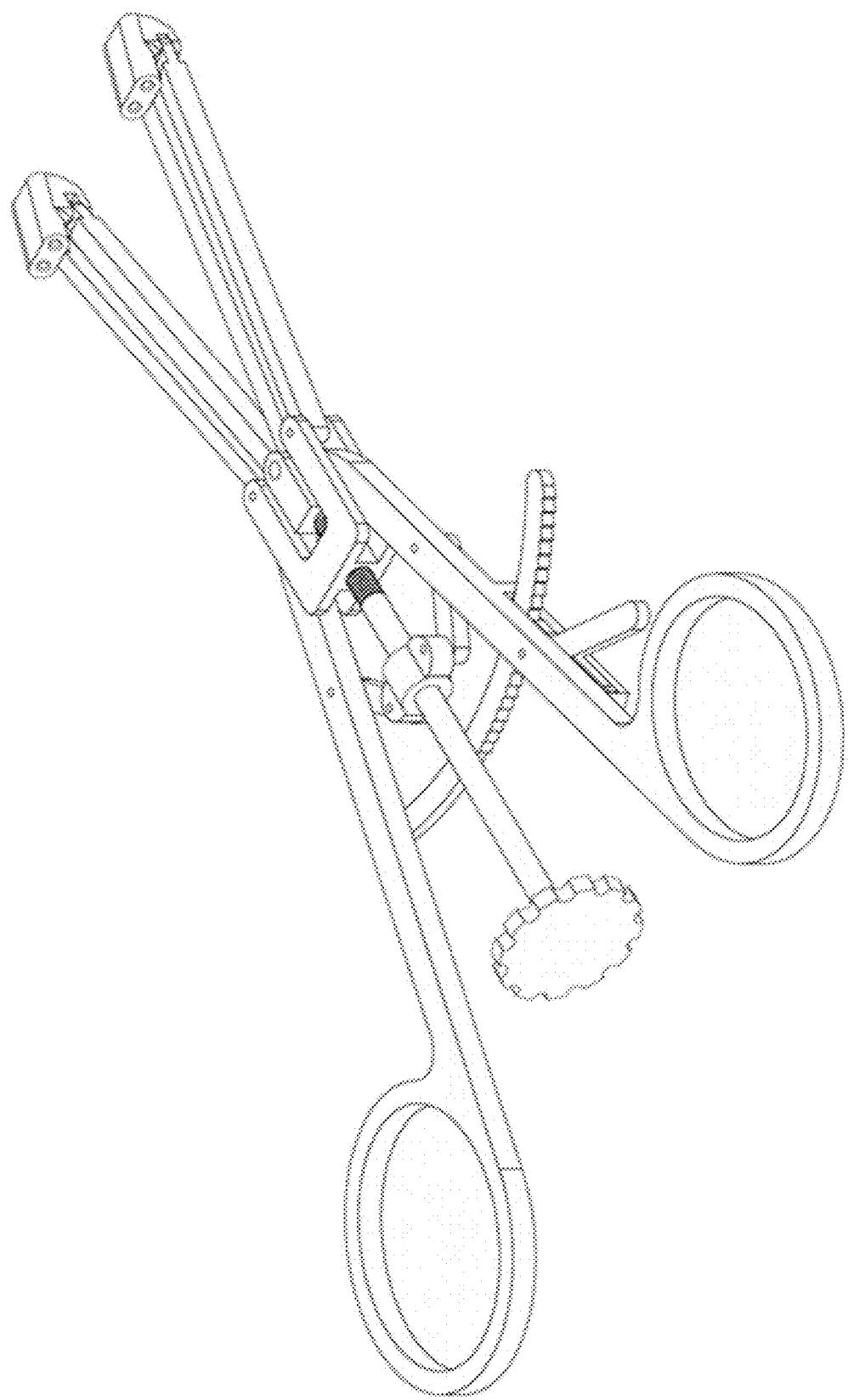
Figure 39A:
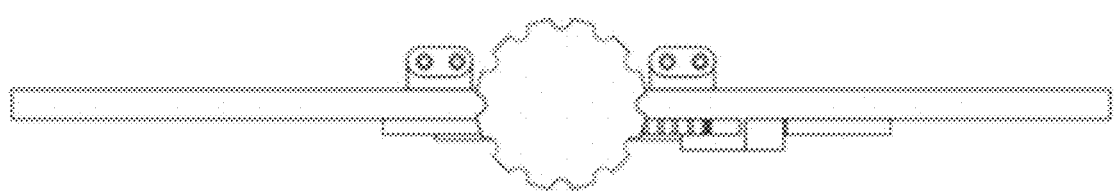
Figure 39B:
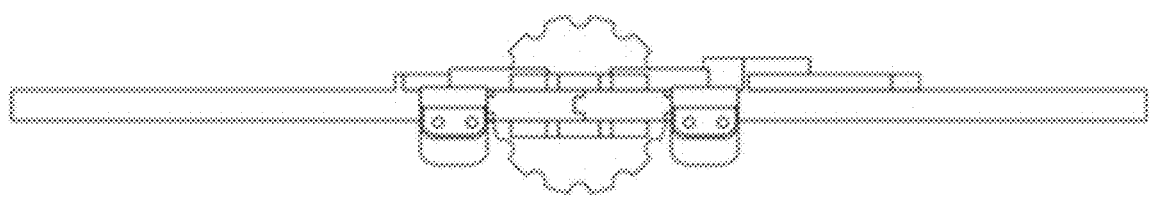
Figures 40A, 40B:
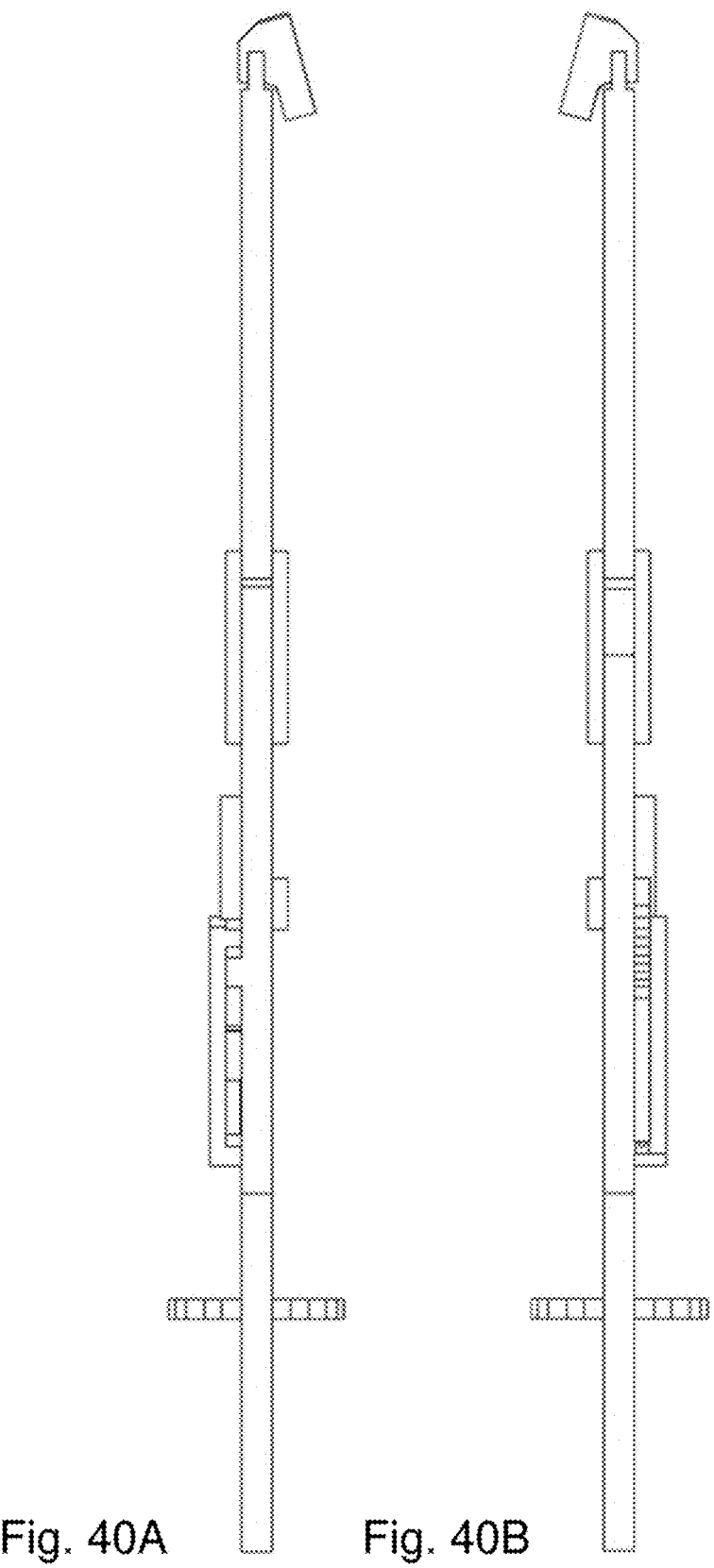
Figure 41:
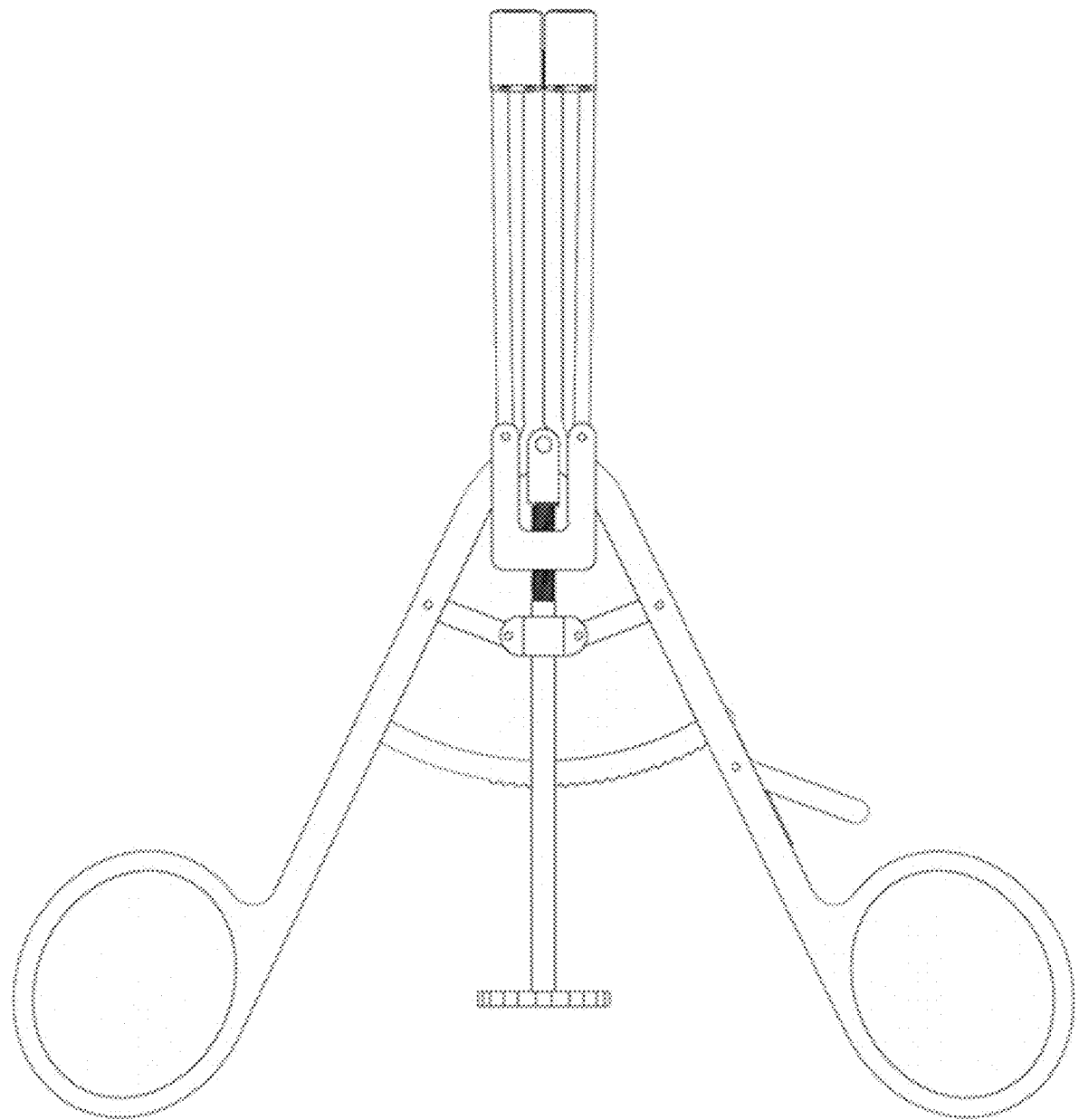
FIGS. 41-49B show a distractor embodiment with feet angled with respect to the pivot axis, arms which are crossed, and a ratcheting mechanism to maintain separation of the feet. A longitudinal screw mechanism controls the relative angle of the feet.
Figure 42:
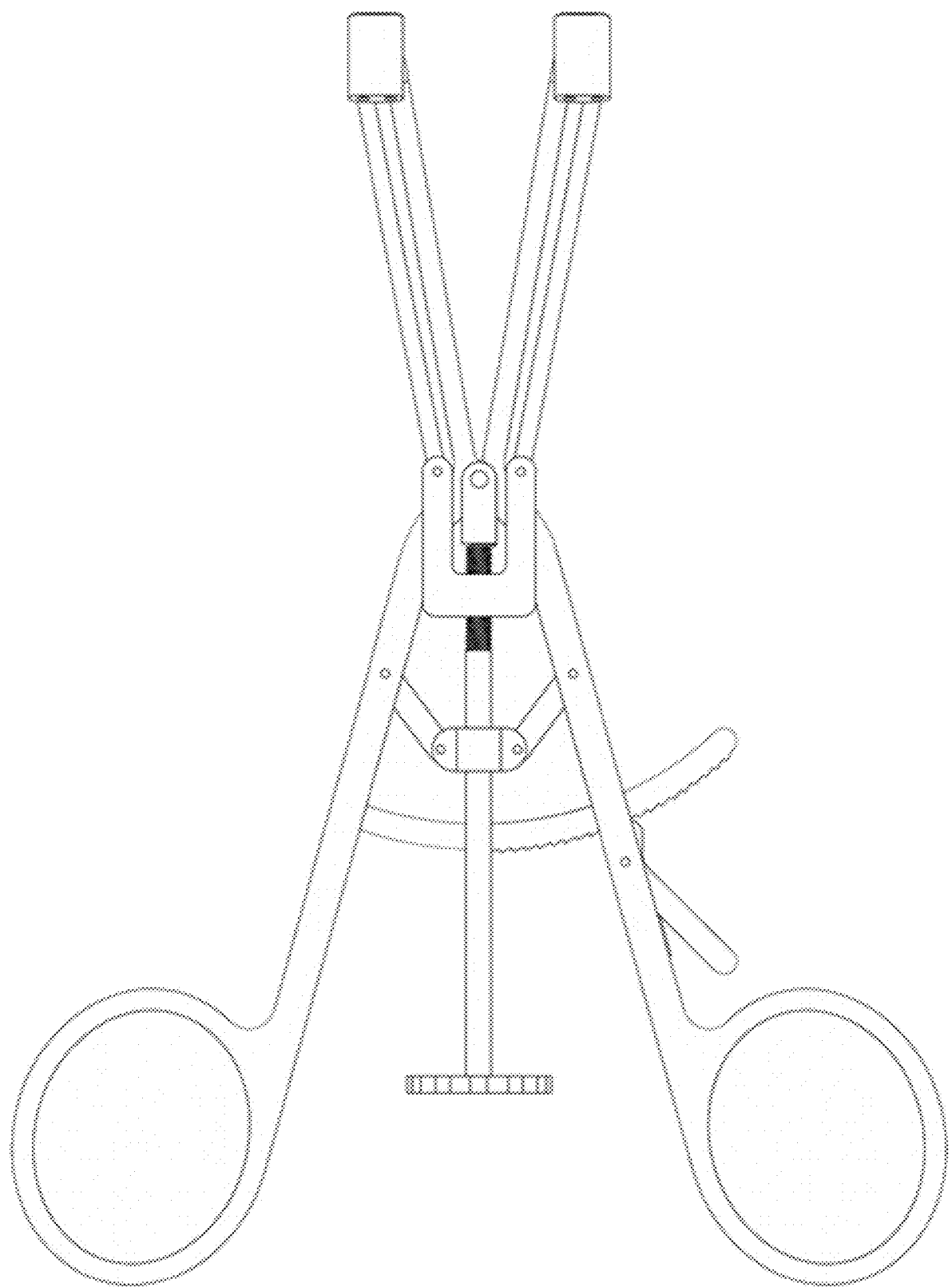
Figure 43:
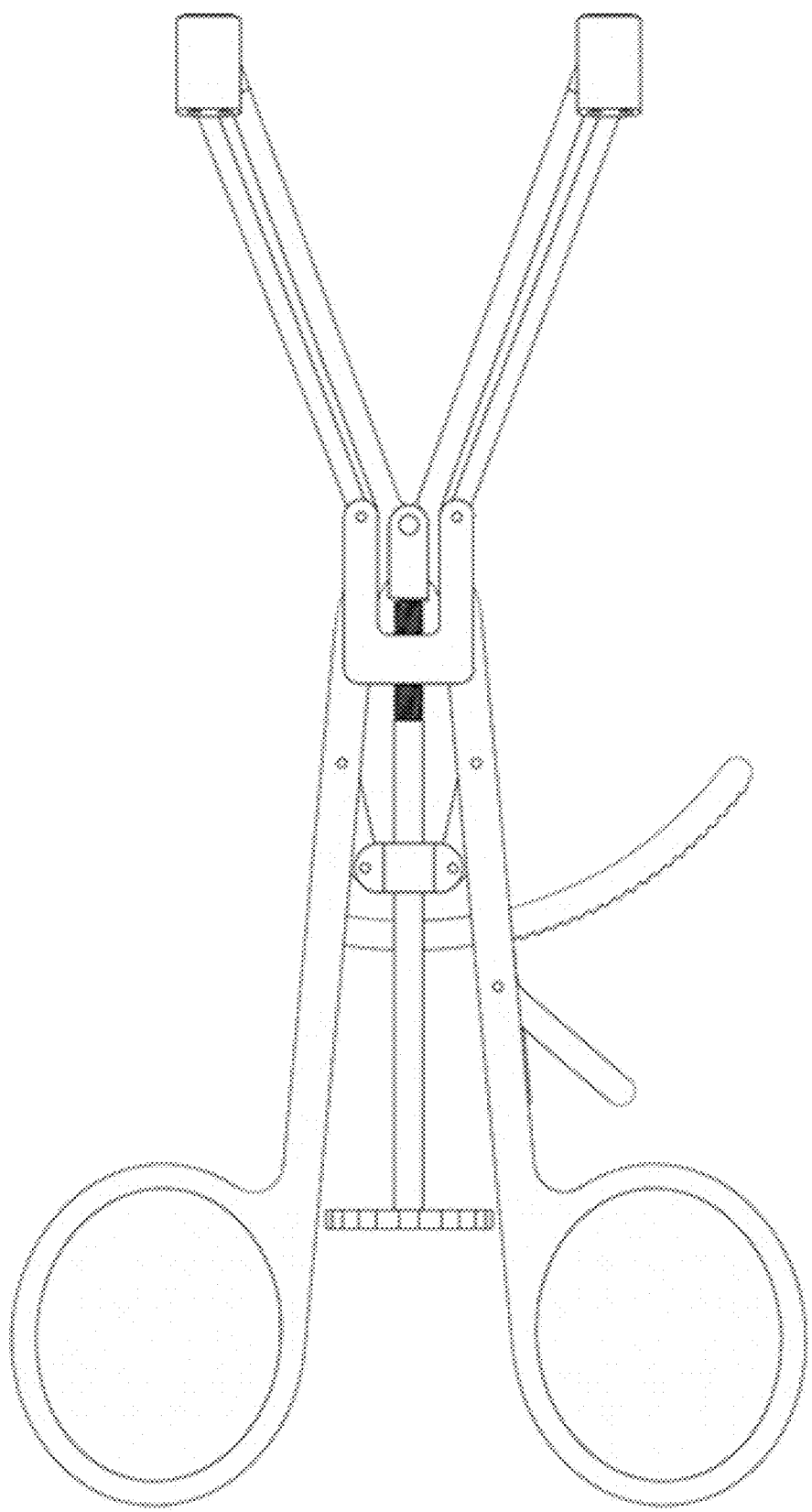
Figure 44:
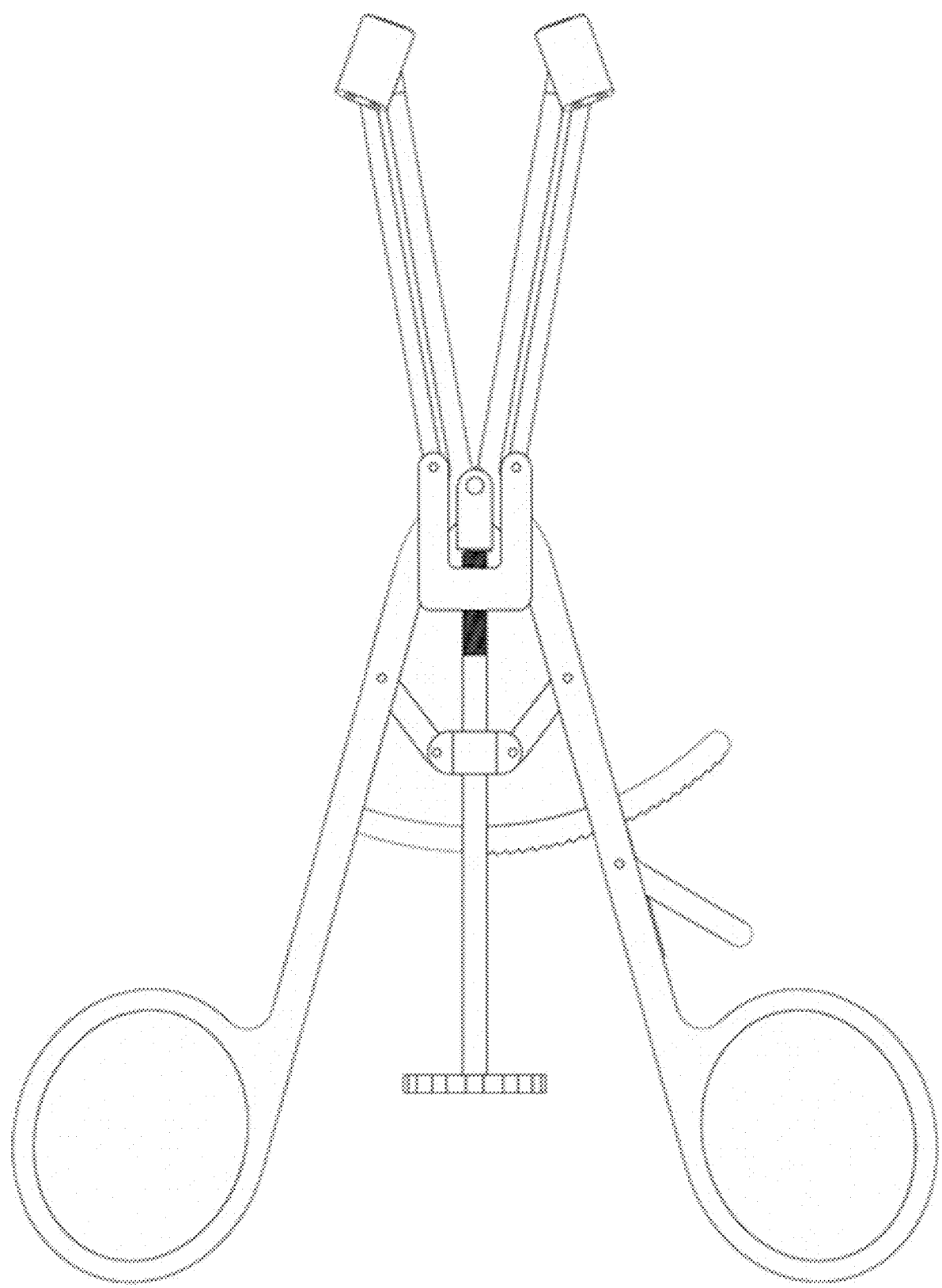
Figure 45:
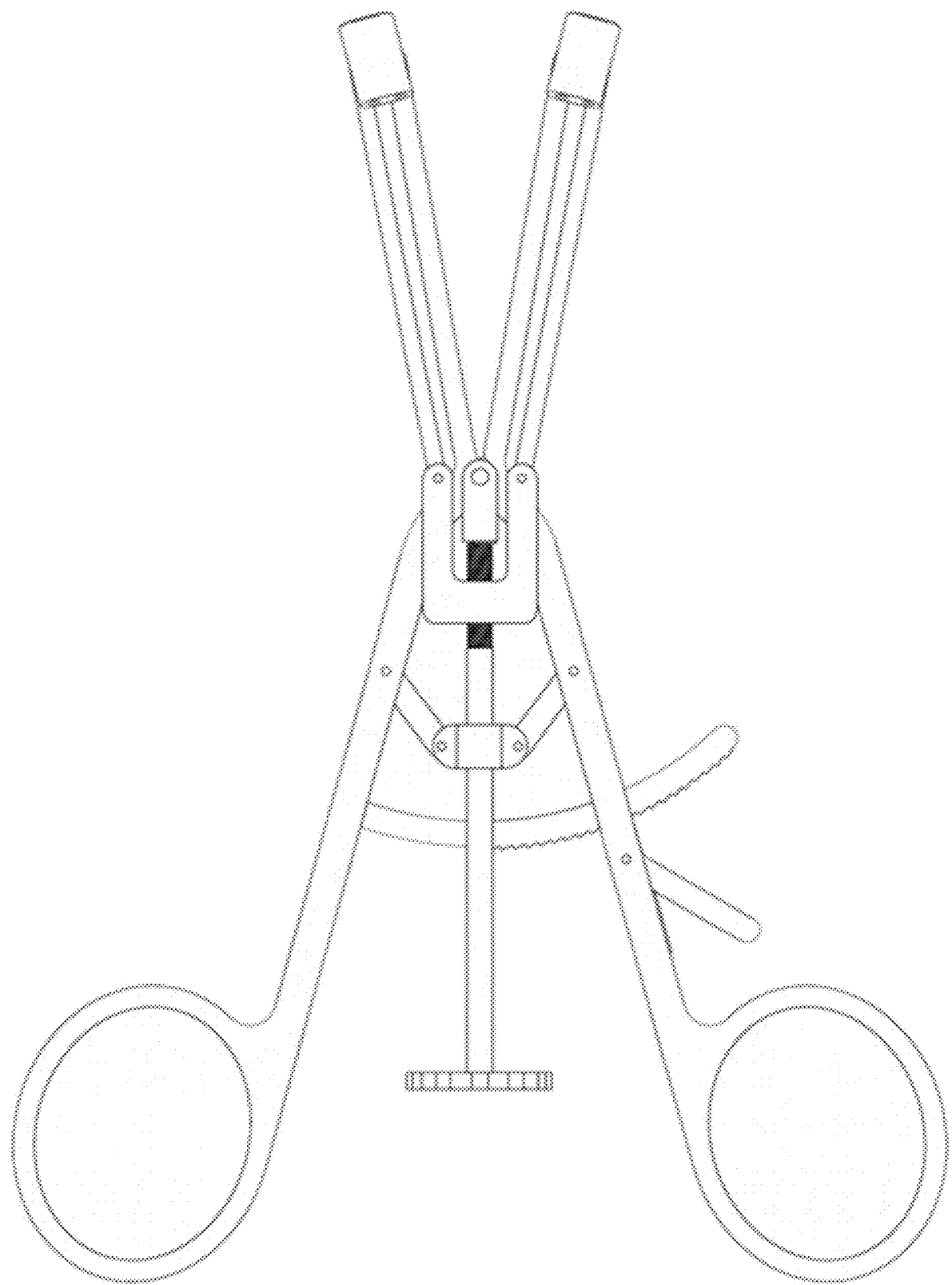
Figure 46:
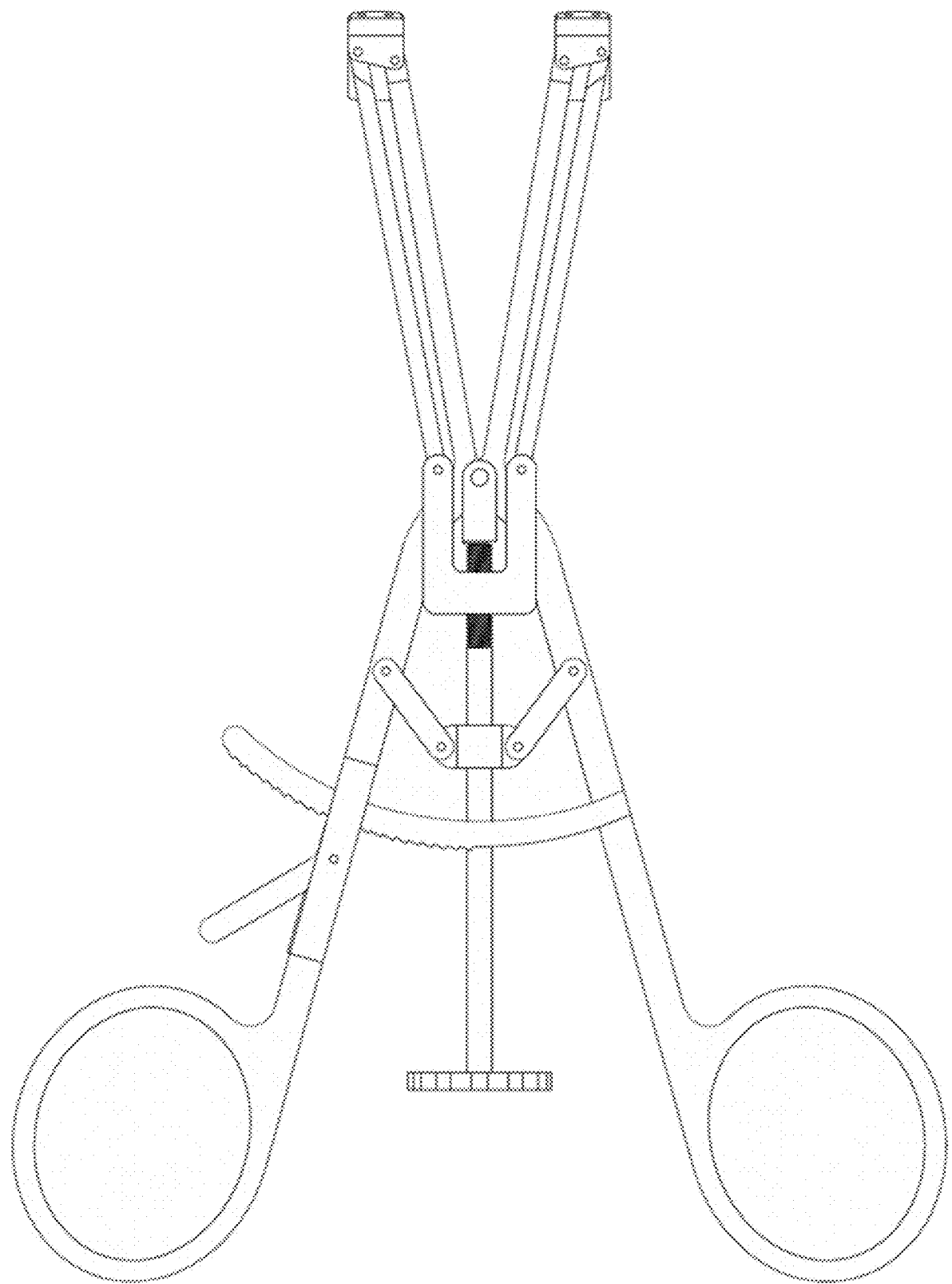
Figure 47:
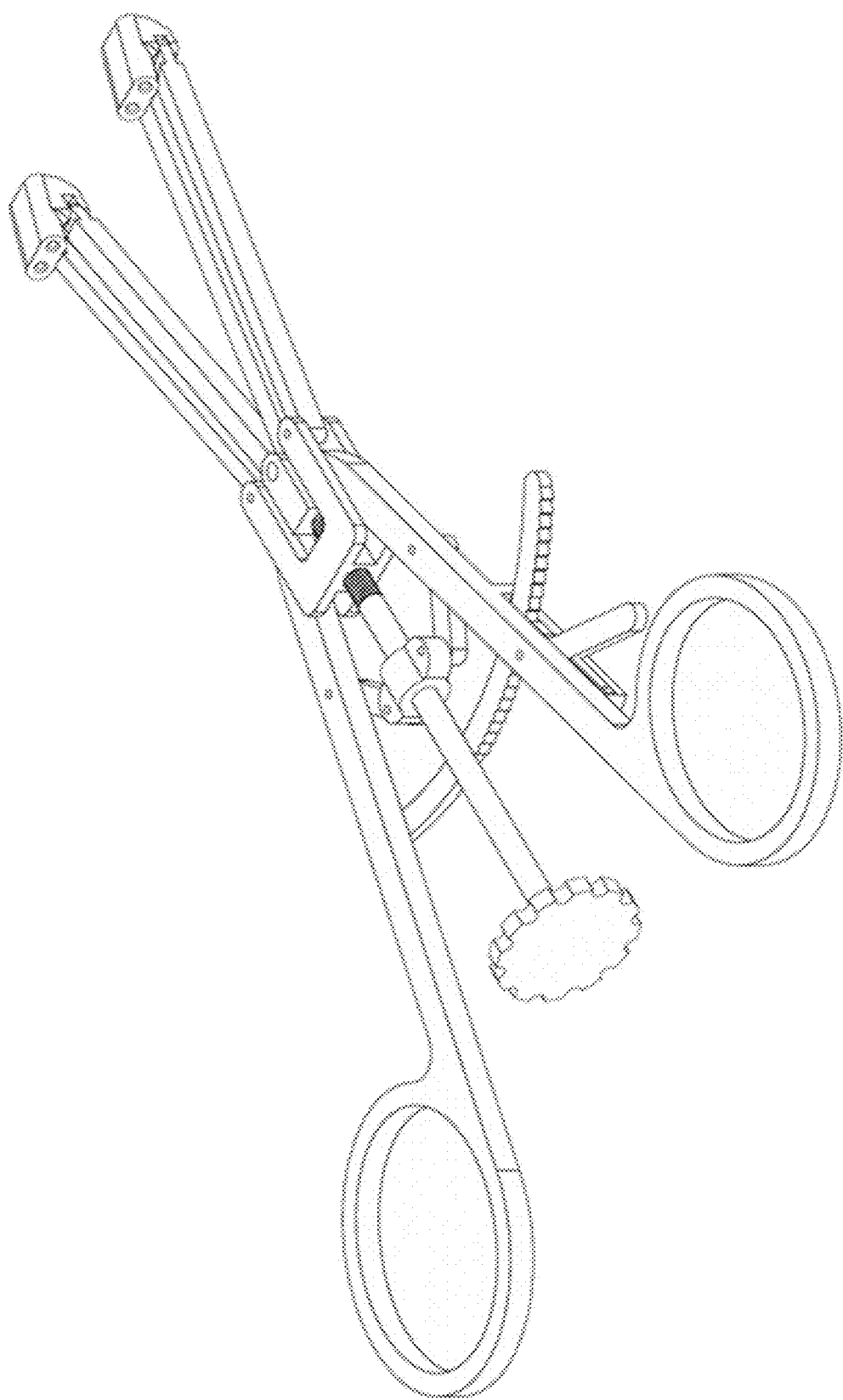
Figure 48A:
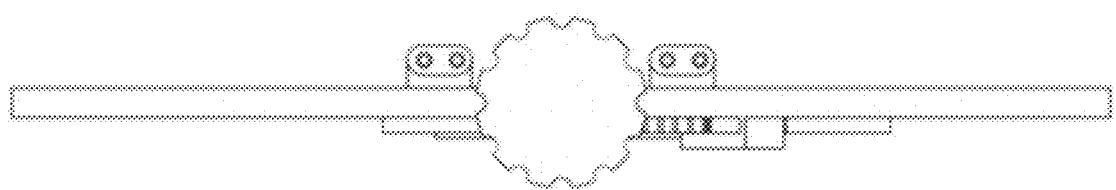
Figure 48B:
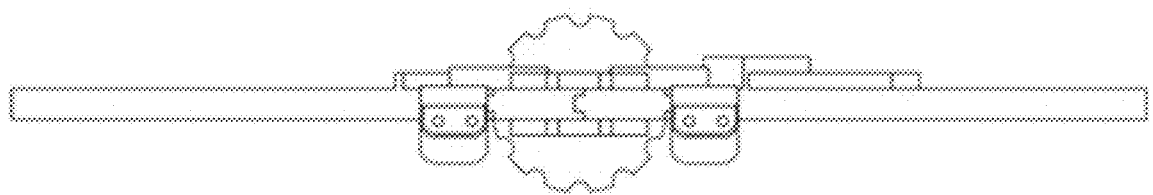
Figure 49A:
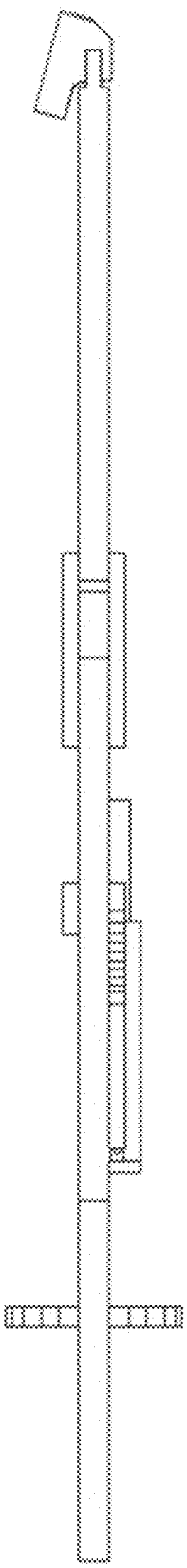
Figure 49B:
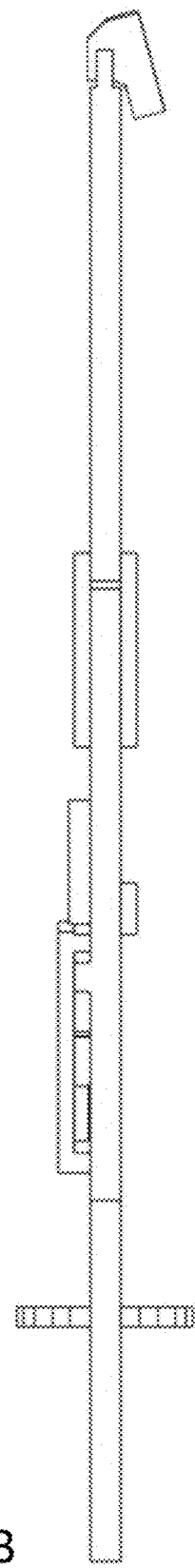
Figure 50:
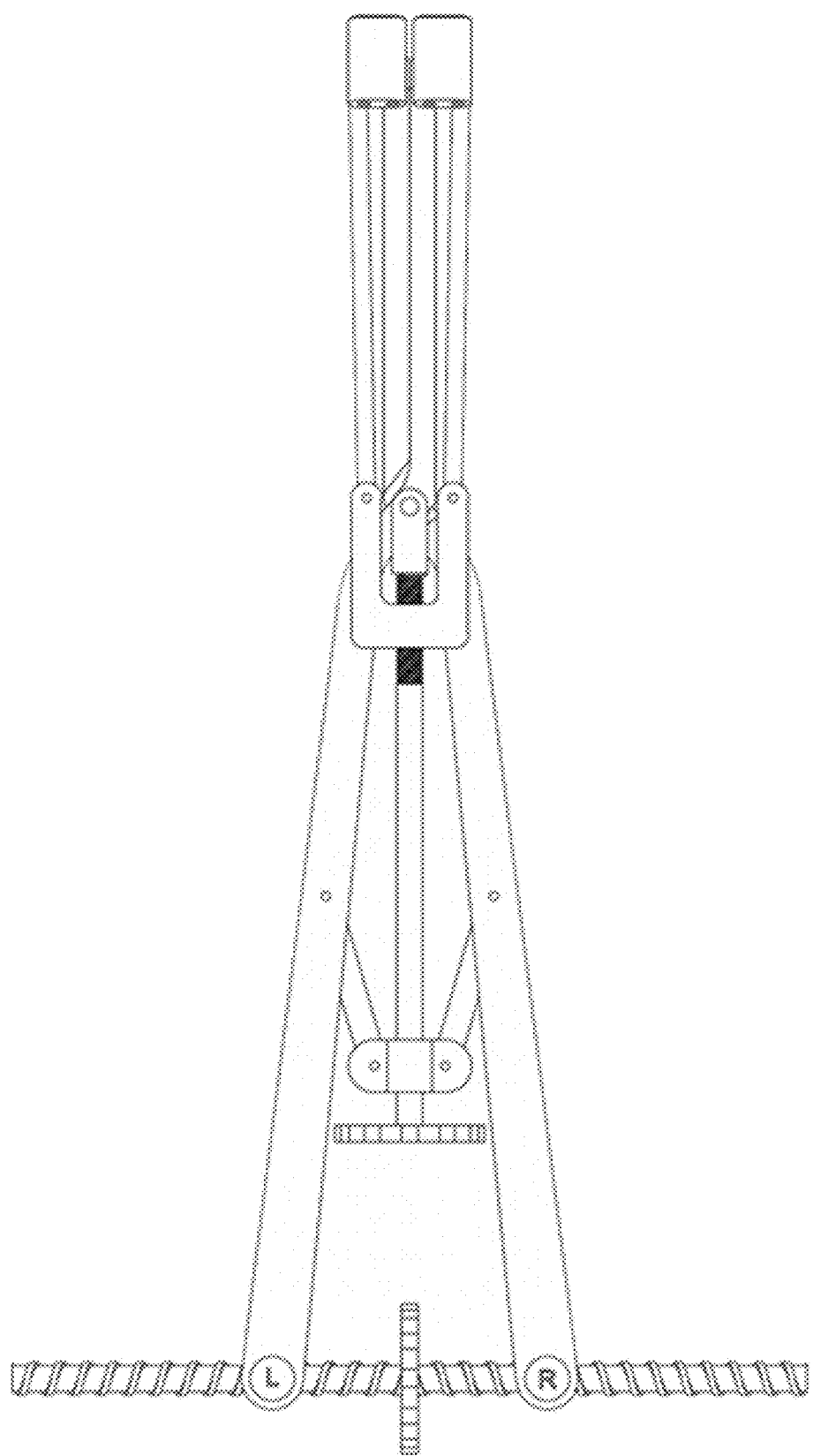
Figure 51:
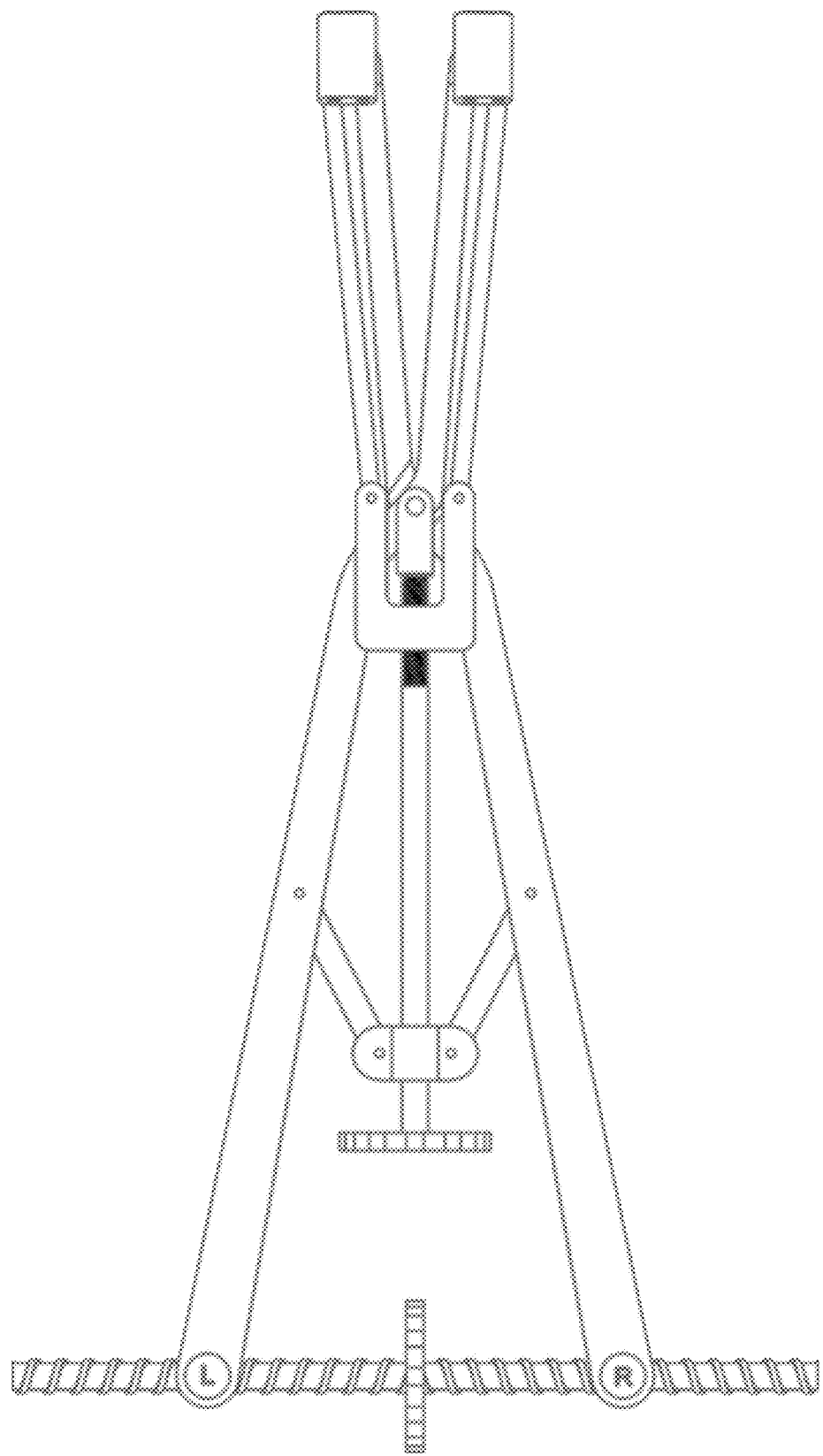
Figure 52:
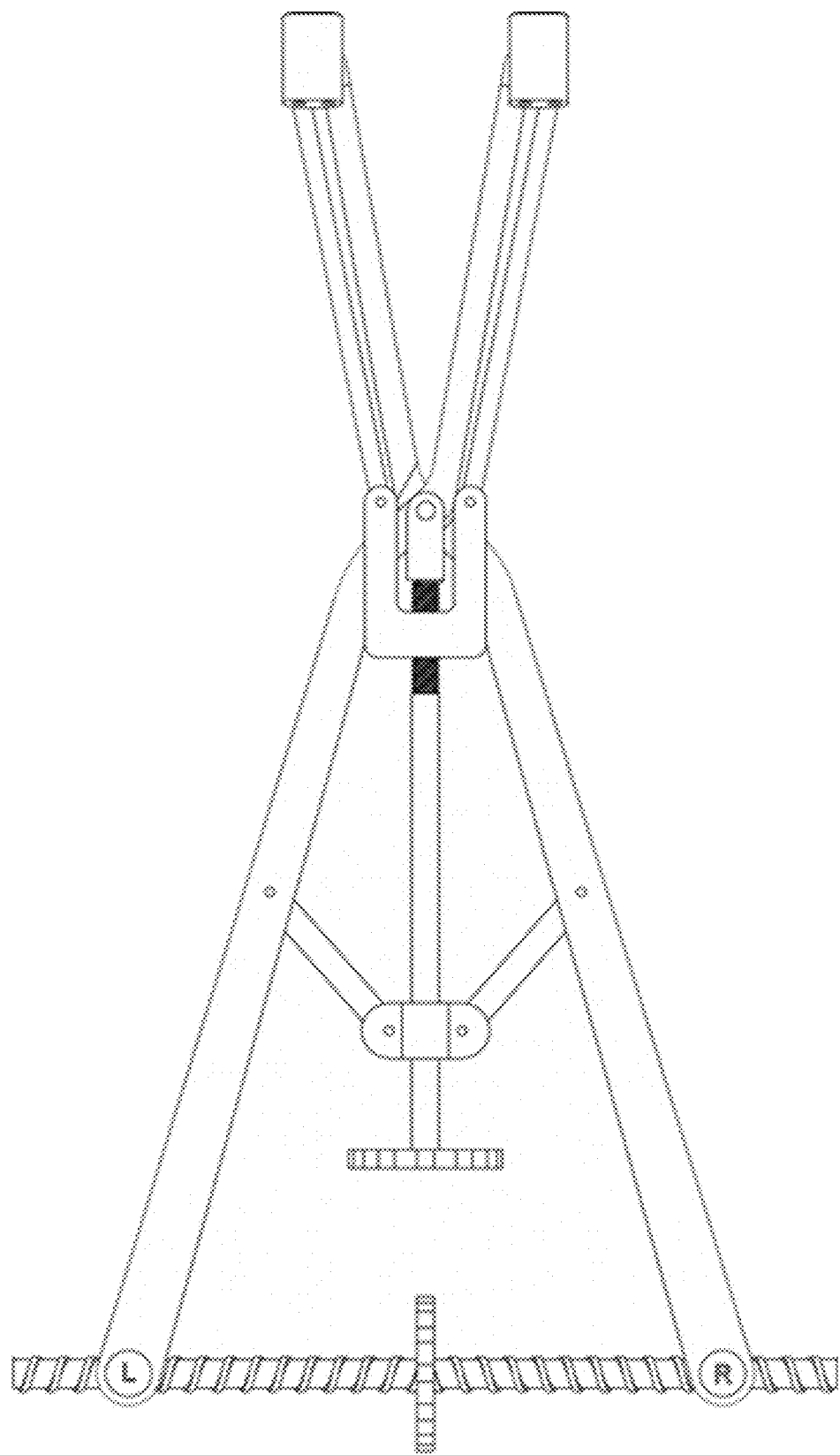
Figure 53:
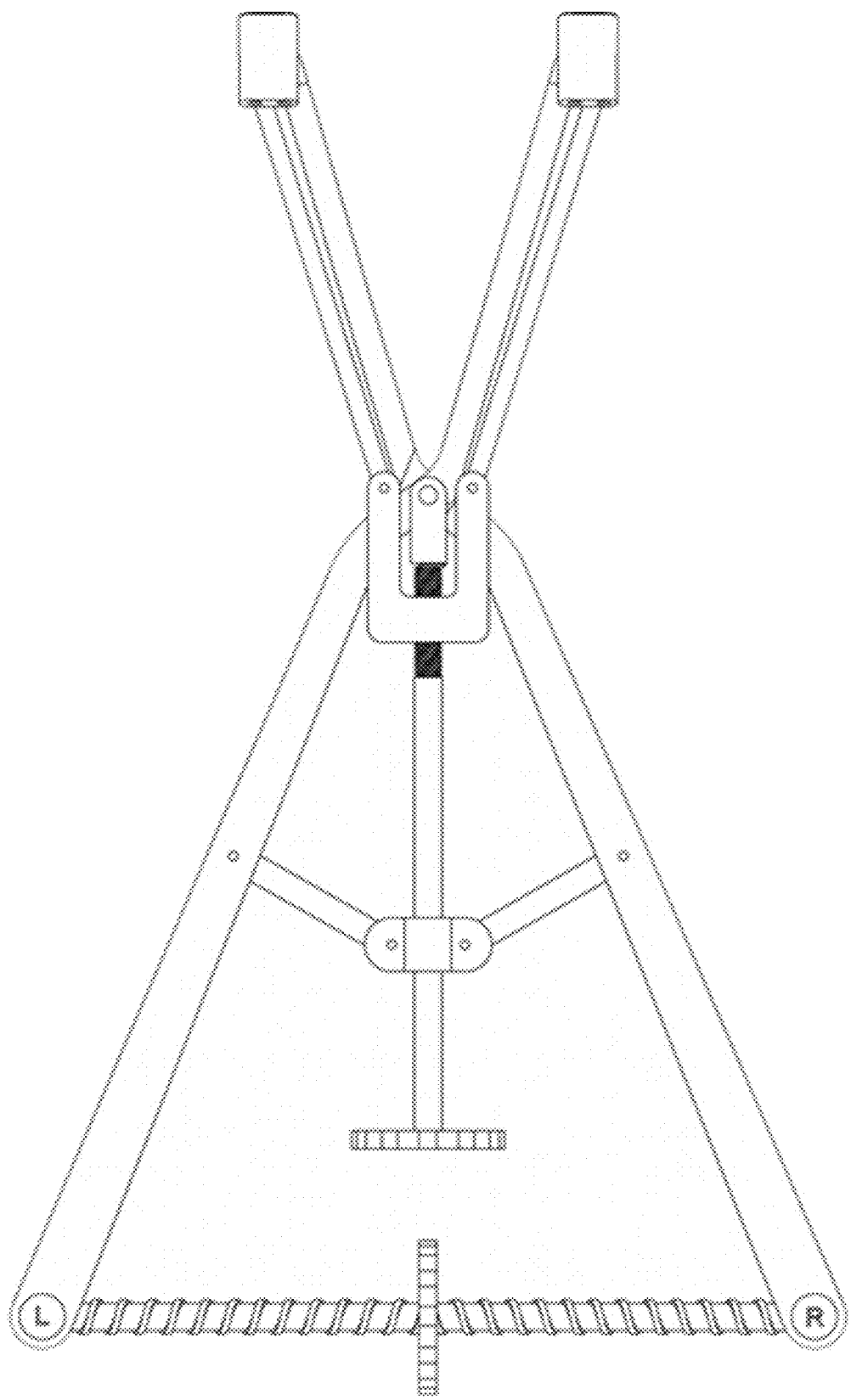
Figure 54:
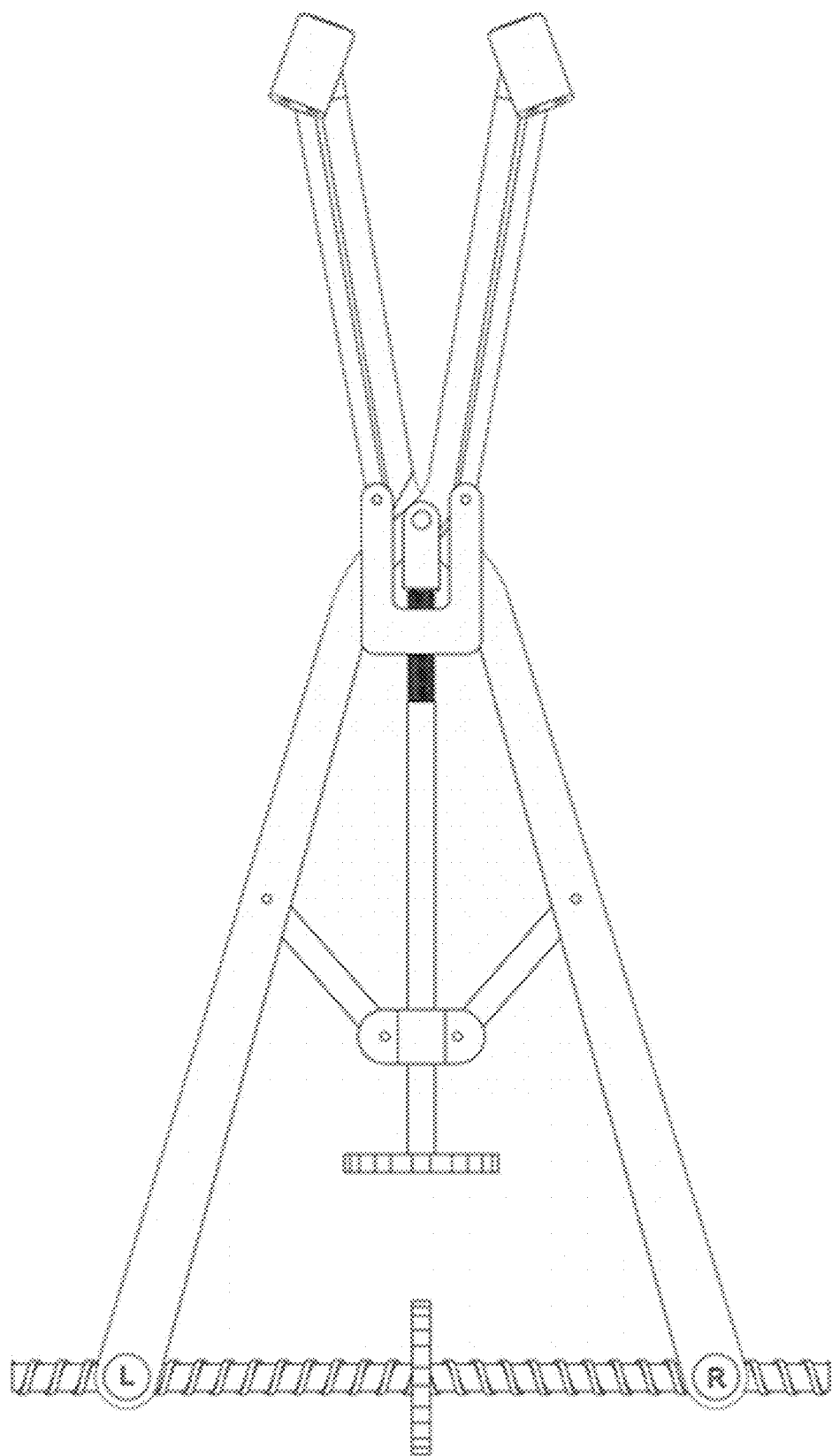
Figure 55:
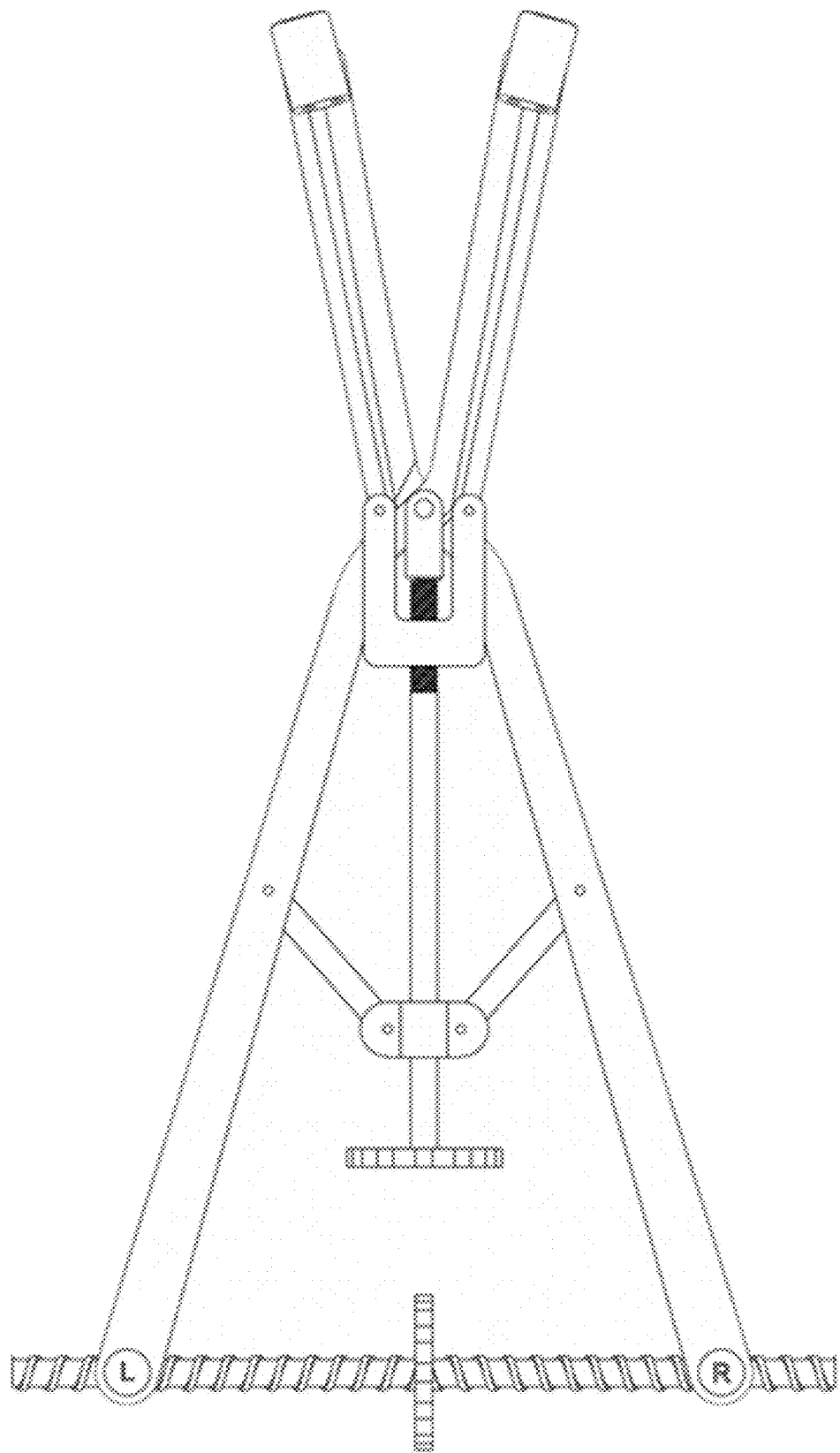
Figure 56:
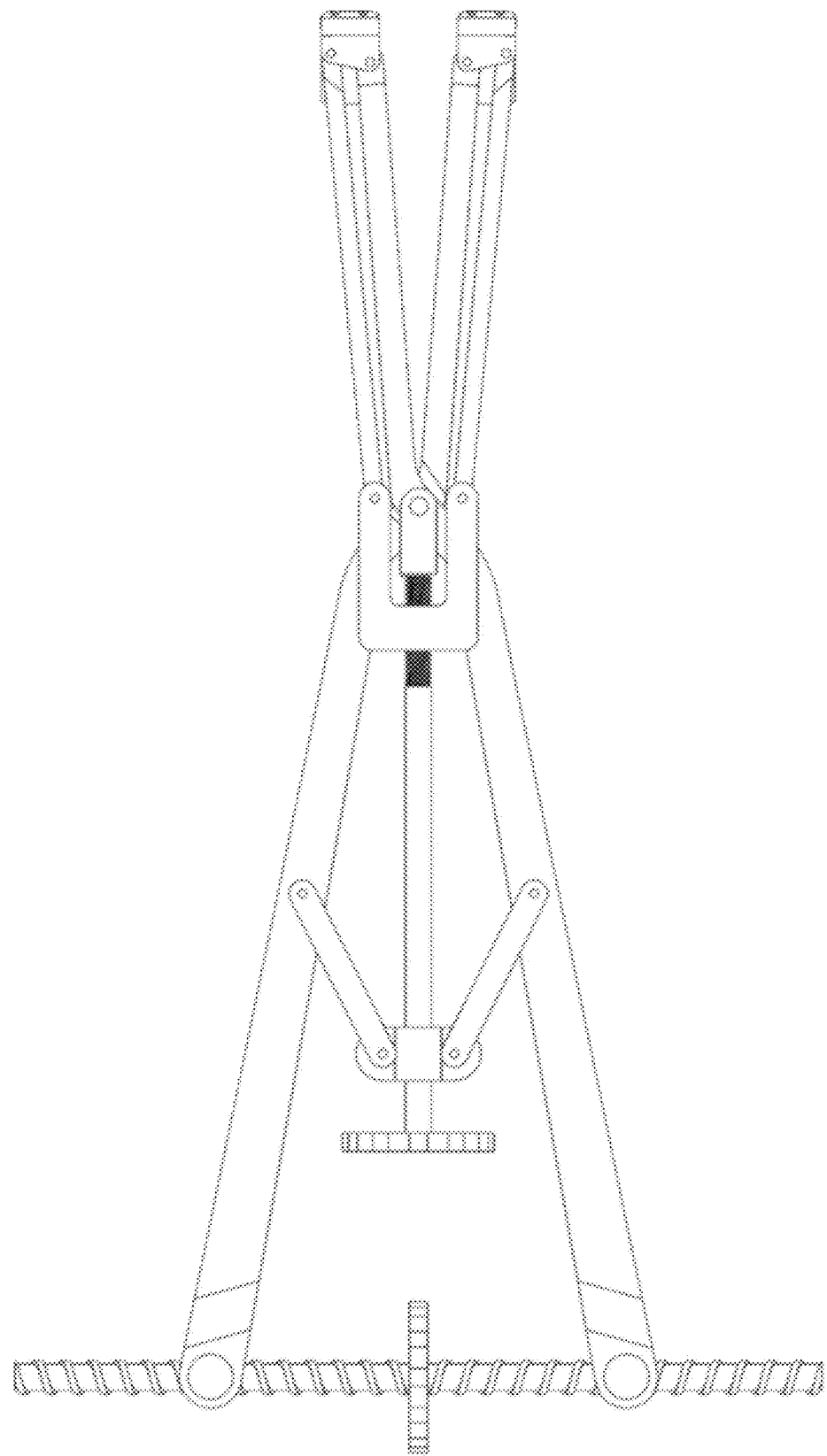
Figure 57:
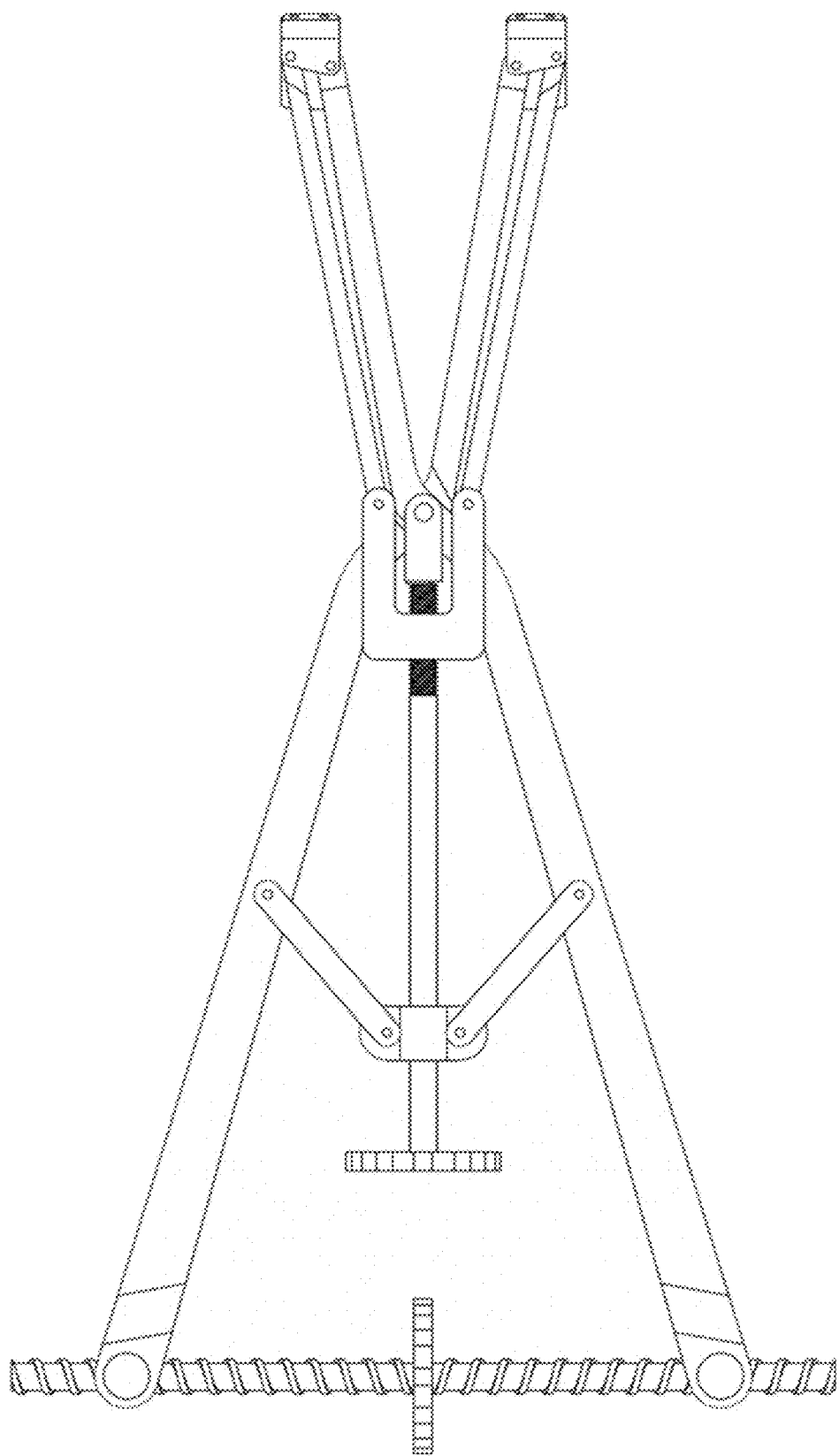
Figure 58:
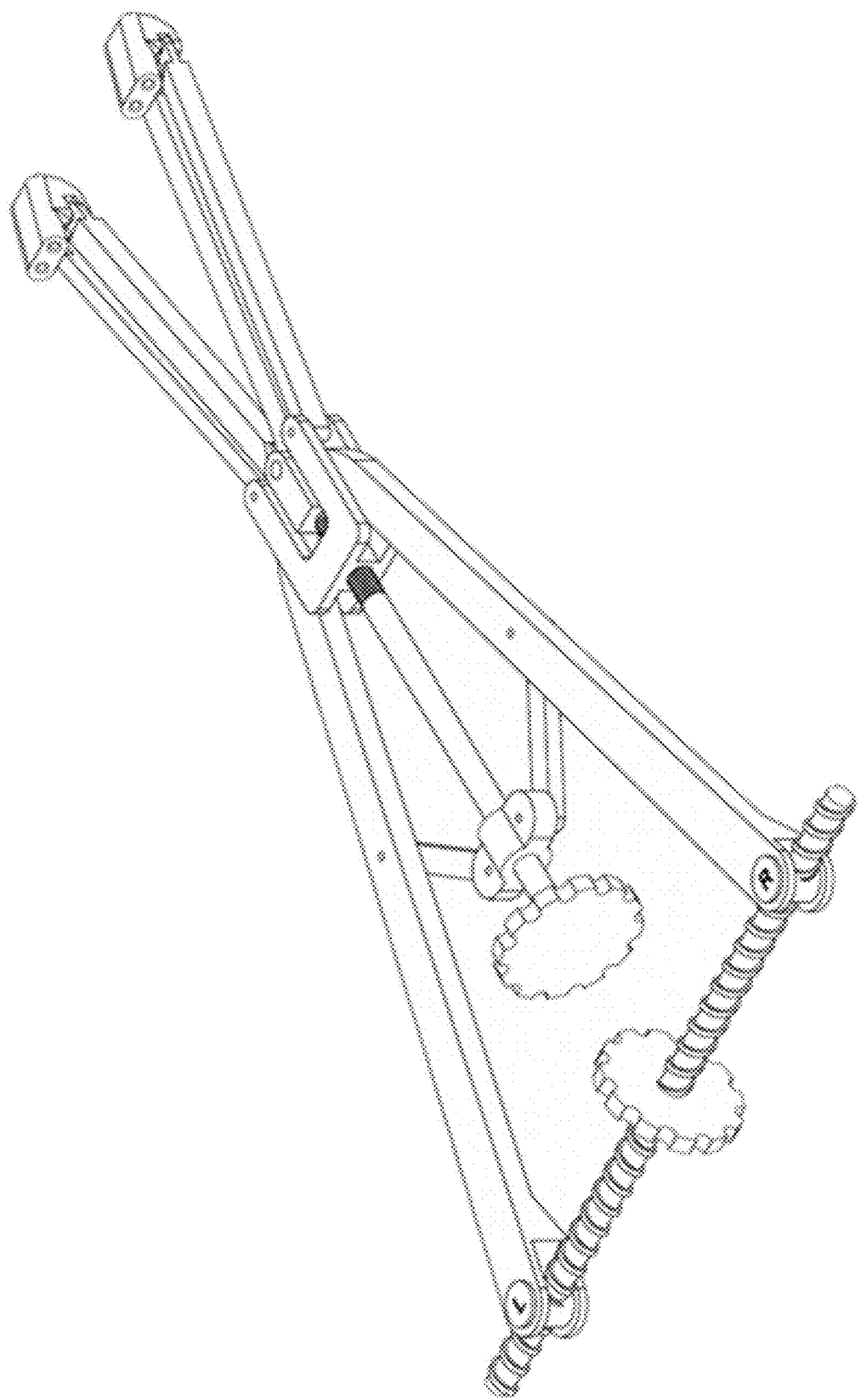
Figure 59A:
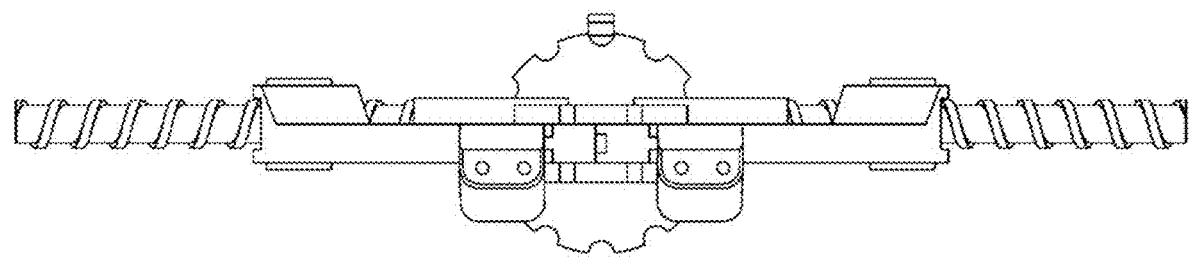
Figure 59B:
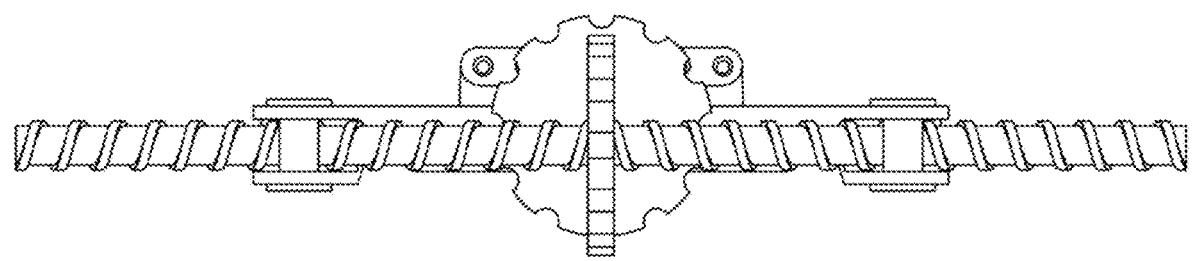
Figures 60A, 60B:
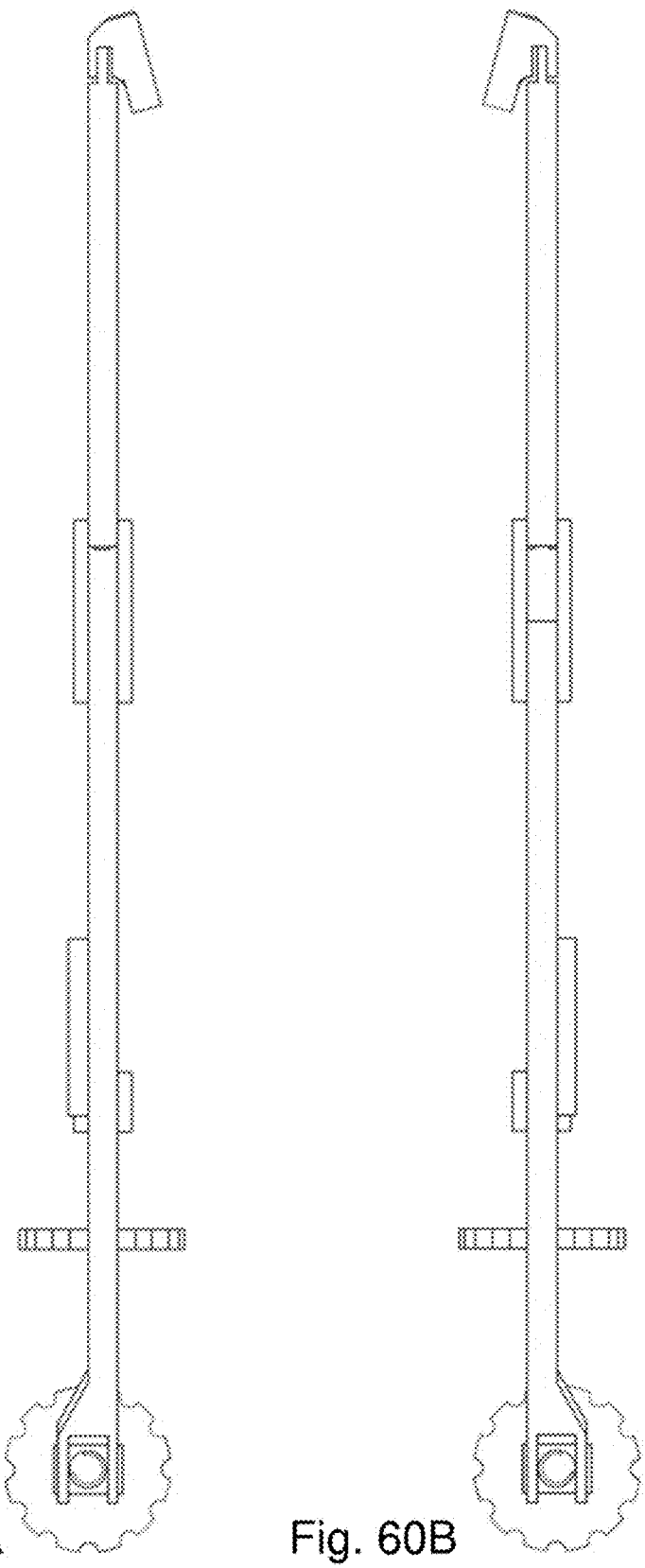

FIG. 29 shows a prior art Intech Medical parallel compressor (www.intech-medical.com/products/instruments/compressors/parallel-compressor/). FIG. 30 shows a prior art Omnia Health self-retaining parallel compressor (www.omnia-health.com/product/retractors-self-retaining-gcompressor-parallel). Note that these prior designs provide only a parallel orientation of the feet, and do not permit independent adjustment of the relative angles of the feet. FIG. 31 shows a prior art Innomed small bone compressor/distractor 4865-LS, with a switchable mechanism to provide ratcheted compression and distraction, in different modes of operation. Such a switchable mechanism may be employed in conjunction with the present designs.

FIGS. 32-60B show embodiments in which the feet are angled with respect to the pivot axis, and therefore in use the scissor mechanism is displaced from the line of sight of the surgeon. In addition, the design as shown has comparatively fewer rigid members, which may flex during use under high load. However, the loss of perfect maintained angles is counterbalanced by lighter weight, and smaller size.

FIGS. 32-40B show a compressor embodiment with feet angled with respect to the pivot axis, arms which are uncrossed, and a ratcheting mechanism to maintain separation of the feet without altering the angle of the feet. A longitudinal screw mechanism controls the relative angle of the feet.

FIGS. 41-49B show a distractor embodiment with feet angled with respect to the pivot axis, arms which are crossed, and a ratcheting mechanism to maintain separation of the feet separation without altering the angle of the feet. A longitudinal screw mechanism controls the relative angle of the feet.

FIGS. 50-60B show a compressor-distractor embodiment with feet angled with respect to the pivot axis, arms which are crossed, and a lateral helical screw mechanism to control separation of the feet without altering the angle of the feet. A longitudinal screw mechanism controls the relative angle of the feet.

Although the present system and/or approach has been described with respect to illustrative examples, many variations and modifications will become apparent to those skilled in the art upon reading the specification. It is therefore the intention that the appended claims be interpreted as broadly as possible in view of the related art to include all such variations and modifications. The device is optimized for orthopedic use, but may be used in other cases where alignment and separation are to be separately controlled, such as in carpentry.

What is claimed is:

1. An instrument for angular and displacement control, comprising:
   a pair of pivotally-connected arms, extending beyond a pivot axis of a first pivot;
   a pair of feet having a relative displacement controlled by the pair of pivotally-connected arms, at least one foot being pivotally mounted for angular displacement with respect to the pivot axis;
   an adjustment configured to control the angular displacement of the at least one foot with respect to the pivot axis; and
   a mechanism, configured to maintain the relative angle of the pair of feet independent of the relative displacement of the pair of feet controlled by the pair of pivotally-connected arms, comprising at least one quadrilateral linkage, having a linkage constraining relative angles of the pair of feet, comprising the first pivot and at least a portion of each of the pivotally-connected arms.

2. The instrument according to claim 1, wherein the pair of feet are configured for affixation to respective bones, wherein the displacement of the pair of pivotally-connected arms controls the relative displacement between the respective bones and the adjustment for control of the angular displacement of the at least one foot controls an angle of the respective bones independent of the control of the displacement between the respective bones.

3. The instrument according to claim 1, wherein the adjustment comprises a helically threaded element and the mechanism comprises a follower displaced by rotation of the helically threaded element, linked to a displaceable side of at least one of the quadrilateral linkages.

4. The instrument according to claim 1, wherein the mechanism comprises a single quadrilateral linkage, and the mechanism comprises:
   a first fitting, proximate to the first pivot, for retaining an axial element;
   a second fitting, displaced from the first fitting, wherein a manipulation of the axial element by the adjustment alters a distance between the first fitting and the second fitting;
   a second pivot on an end of a pivotally-connected arm extending beyond the first pivot;
   one of the feet being pivotally mounted by the second pivot to the end of one of the pair of pivotally-connected arms extending beyond the first pivot;
   a third pivot each linked to the second fitting, and being laterally displaced from a central plane of symmetry of the pair of pivotally-connected arms;
   a fourth pivot on the pivotally mounted foot, laterally displaced from the second pivot from the central plane of symmetry; and
   a lateral arm linking the third pivot and the fourth pivot, wherein the first pivot, second pivot, third pivot and fourth pivot define vertices of the quadrilateral linkage, and the pivotally-connected arm extending beyond the first pivot, the feet, the lateral arm, and the second fitting representing the sides of the quadrilateral linkage.

5. The instrument according to claim 4, further comprising an aperture surrounding the axial element, configured to maintain the axial element centered between the pair of pivotally-connected arms.

6. The instrument according to claim 5, further comprising a transverse screw configured to control a displacement of the pair of pivotally-connected arms, wherein the axial element is centered between the pair of pivotally-connected arms in the central plane by a sleeve.

7. The instrument according to claim 1, wherein the mechanism comprises a pair of parallelogram linkages comprising the quadrilateral linkage, and the mechanism comprises:
   a first fitting, proximate to the first pivot, for retaining an axial element;
   a second fitting, displaced from the first fitting, wherein a manipulation of the axial element by the adjustment alters a distance between the first fitting and the second fitting;
   a pair of second pivots on ends of the pair of pivotally-connected arms extending beyond the first pivot;
   the pair of feet being pivotally mounted by the pair of second pivots to the ends of the pair of pivotally-connected arms extending beyond the first pivot;
   a pair of third pivots each linked to the second fitting, and being laterally displaced from a central plane of symmetry of the pair of pivotally-connected arms;
   a pair of fourth pivots on the pair of feet, laterally displaced from the pair of second pivots from the central plane of symmetry; and
   a pair of lateral arms linking the third pivots and the fourth pivots, on the same side of the central plane of symmetry,
   wherein the first pivot, second pivots, third pivots and fourth pivots define vertices of the pair of parallelogram linkages sharing the first pivot, and the pivotally-connected arms extending beyond the first pivot, the feet, the pair of lateral arms, and the second fitting representing the sides of the pair of parallelogram linkages.

8. The instrument according to claim 1, wherein the pair of pivotally-connected arms act across the central plane through the first pivot, such that compression on one side of the first pivot causes compression on the other side of the first pivot.

9. The instrument according to claim 1, wherein the pair of pivotally-connected arms act on respective sides of the central plane through the first pivot, such that compression on one side of the first pivot causes expansion on the other side of the first pivot.

10. The instrument according to claim 1, further comprising a ratchet configured to adjust and retain unidirectional displacement of the pair of pivotally-connected arms until released.

11. The instrument according to claim 1, wherein the pair of feet each have a bore hole, angled with respect to a plane defined by the pair of pivotally-connected arms.

12. An instrument, comprising:
   a pair of pivotally-connected arms, extending beyond a pivot axis of a first pivot and defining a central plane through the first pivot;
   a pair of feet mounted to ends of the pair of pivotally-connected arms, configured to be displaced dependent on a relative angle of the pair of pivotally-connected arms, at least one foot being mounted on a respective pivotally-connected arm for angular reorientation with respect to the other foot along the pivot axis;
   a mechanism configured to change the angular reorientation of the at least one foot with respect to the other foot along the pivot axis; and
   at least one quadrilateral linkage having a member linking the pair of feet configured to maintain a relative angle between the pair of feet while the pair of pivotally-connected arms are displaced about the pivot axis.

13. The instrument according to claim 12, wherein the pair of feet are configured for affixation to respective bones, wherein the displacement of the pair of pivotally-connected arms controls the displacement between the respective bones and the mechanism controls an angle of the respective bones independent of the control of the displacement between the respective bones.

14. The instrument according to claim 12, wherein the relative angle between the pair of feet is controlled by rotation of a helically threaded cylinder.

15. The instrument according to claim 12, wherein the at least one quadrilateral linkage comprises a pair of parallelogram linkages, each having rigid arms connected by pivots, which share the first pivot as a common pivot.

16. The instrument according to claim 12, wherein the at least one quadrilateral linkage comprises a single quadrilateral linkage comprising the first pivot and a portion of one of the pivotally-connected arms.

17. An instrument for aligning bone, comprising:
   a pair of pivotally-connected arms, extending beyond a pivot axis of a first pivot and defining a central plane;
   a pair of elements mounted to ends of the pair of pivotally-connected arms affixing the pair of elements to sections of bone, having a distance between the pair of elements controlled by an angle of the pair of pivotally-connected arms;
   a mechanism configured to alter a relative angle of one element with respect to the other element about the pivot axis; and
   a quadrilateral linkage linking the pair of elements, configured to maintain a relative angle of the pair of elements about the pivot axis established by the mechanism over a range of angles of the pair of pivotally-connected arms.

18. The instrument according to claim 17, wherein the mechanism comprises a helically threaded rod and a follower, and the mechanism alters the relative angle of the pair of elements by displacement of the follower by rotation of the helically threaded rod.

19. The instrument according to claim 18, wherein each of the pair of elements comprises a foot having an aperture configured to align a bone screw for insertion into bone.

20. The instrument according to claim 18, wherein the mechanism comprises a quadrilateral linkage, comprising:
   a first fitting, proximate to the first pivot, for retaining an axial member;
   a second fitting, displaced from the first fitting, wherein a manipulation of the axial member by the adjustment alters a distance between the first fitting and the second fitting;
   a second pivot on an end of a pivotally-connected arm extending beyond the first pivot;
   one of the elements being pivotally mounted by the second pivot to the end of one of the pair of pivotally-connected arms extending beyond the first pivot;
   a third pivot each linked to the second fitting, and being laterally displaced from a central plane of symmetry of the pair of pivotally-connected arms;

a fourth pivot on the pivotally-mounted element, laterally displaced from the second pivot from the central plane of symmetry; and
a lateral arm linking the third pivot and the fourth pivot, wherein the first pivot, second pivot, third pivot and fourth pivot define vertices of the quadrilateral linkage, and the pivotally-connected arm extending beyond the first pivot, the elements, the lateral arm, and the second fitting representing the sides of the quadrilateral linkage.

* * * * *